(12) United States Patent
Chang et al.

(10) Patent No.: US 9,201,014 B2
(45) Date of Patent: Dec. 1, 2015

(54) DEVELOPMENT OF PHOTOSTABLE NEAR-IR CYANINE DYES FOR IN VIVO IMAGING

(71) Applicant: National University of Singapore, Singapore (SG)

(72) Inventors: Young-Tae Chang, Singapore (SG); Animesh Samanta, Singapore (SG); Marc Vendrell Escobar, Singapore (SG); Nam-Young Kang, Singapore (SG); Kaustabh Kumar Maiti, Singapore (SG); Kiat Seng Soh, Singapore (SG); Dinish Unnimadhava Kurup Soudamini Amma, Singapore (SG); Malini Olivo, Singapore (SG); Sung-Jin Park, Seoul (KR); Raj Kumar Das, West Bengal (IN)

(73) Assignees: National University of Singapore, Singapore (SG); Agency for Science, Technology and Research, Singapore (SG)

( * ) Notice: Subject to any disclaimer, the term of this patent is extended or adjusted under 35 U.S.C. 154(b) by 353 days.

(21) Appl. No.: 13/625,832

(22) Filed: Sep. 24, 2012

(65) Prior Publication Data
US 2013/0101517 A1 Apr. 25, 2013

Related U.S. Application Data

(63) Continuation-in-part of application No. PCT/SG2011/000117, filed on Mar. 24, 2011.

(60) Provisional application No. 61/317,109, filed on Mar. 24, 2010.

(51) Int. Cl.
| A61B 10/00 | (2006.01) |
| A61B 5/00 | (2006.01) |
| A61B 8/00 | (2006.01) |
| G01N 21/65 | (2006.01) |
| A61K 49/00 | (2006.01) |
| C09B 23/01 | (2006.01) |
| C09B 23/08 | (2006.01) |
| G01N 33/58 | (2006.01) |

(52) U.S. Cl.
CPC .......... *G01N 21/658* (2013.01); *A61K 49/0032* (2013.01); *A61K 49/0058* (2013.01); *C09B 23/0016* (2013.01); *C09B 23/0041* (2013.01); *C09B 23/0066* (2013.01); *C09B 23/086* (2013.01); *G01N 33/582* (2013.01)

(58) Field of Classification Search
CPC ....... A61K 51/00; A61K 51/04; A61K 49/00; A61K 49/01; A61K 49/0013; A61K 49/0017; A61K 49/0032; A61K 49/005; A61K 49/0058; C09B 23/0016; C09B 23/0041; C09B 23/0066; C09B 23/086; G01N 33/582; G01N 21/658

USPC ............. 424/1.11, 1.65, 1.81, 1.85, 1.89, 9.1, 424/9.2, 9.6; 548/400, 578; 8/636

See application file for complete search history.

(56) References Cited

U.S. PATENT DOCUMENTS

| 6,159,443 A * | 12/2000 | Hallahan ...................... 424/1.17 |
| 7,468,241 B1 | 12/2008 | Lynch et al. |
| 7,504,089 B2 | 3/2009 | Lugade et al. |
| 2006/0024771 A1 | 2/2006 | Kang |
| 2008/0206886 A1 | 8/2008 | Wang et al. |

FOREIGN PATENT DOCUMENTS

| CN | 101149373 | 3/2008 |
| WO | WO 96/00902 | 1/1996 |
| WO | WO 99/49082 | 9/1999 |
| WO | WO 00/31534 | 6/2000 |
| WO | WO 2006/136543 A2 | 12/2006 |
| WO | WO 2007/044866 A2 | 4/2007 |
| WO | WO 2009/080689 A1 | 7/2009 |
| WO | WO 2010/031758 A1 | 3/2010 |
| WO | WO 2011/119114 A1 | 9/2011 |

OTHER PUBLICATIONS

Kiyose et al, Chem. Eur. J, 2009, vol. 15, pp. 9191-9200.*
Bhushan, KR., et al., "Microwave-assisted synthesis of near-infrared fluorescent sphingosine derivatives", *Chemical Communications*, 7(37): 4419-4421 (2008).
International Preliminary Report on Patentability, International Application No. PCT/SG2011/000117, "Development of Photostable Near-IR Cyanine Dyes for In Vivo Imaging" Date of Issuance: Sep. 25, 2012.
Kiyose, K., "Development of a ratiometric fluorescent zinc ion probe in near-infrared region, based on tricarbocyanine chromophore", *Journal of American Chemical Society*, 128(20): 6548-6549 (2006).
Kiyose, K., "Molecular Design Strategies for Near-Infrared Ratiomet6ric Fluorescent Probes Based on the Unique Spectral Properties of Aminocyanines", *Chemistry*, 15(36): 9191-9200 (2009).

(Continued)

*Primary Examiner* — D L Jones
(74) *Attorney, Agent, or Firm* — Hamilton, Brook, Smith & Reynolds, P.C.

(57) ABSTRACT

A compound of structural formula (I):

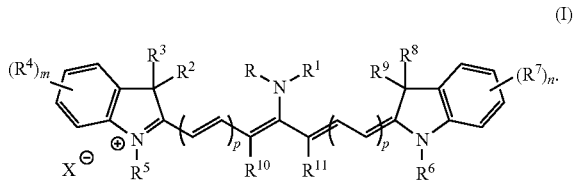

The values and alternative values are as defined herein. The invention also includes biosensors comprising nanoparticles functionalized with a compound of structural formula (I). Also described is a method for labeling a biomolecule using a compound of structural formula (I) and a method of detecting a target biomolecule using a compound of structural formula (I) or a biosensor of the invention.

6 Claims, 26 Drawing Sheets

(56) References Cited

OTHER PUBLICATIONS

Kojima, K., et al., "Development of near-infrared fluorescent probes for nitric oxide and zinc-ion", *Progress in biomedical optics and imaging*, 8: 1-12 (2007).

Lee, LG, "Near-IR dyes in three-color volumetric capillary cytometry: cell analysis with 633- and 785-nm laser excitation", *Cytometry*, 21(2): 120-128 (1995).

Samanta, A., et al., A Photostable Near-Infrared Protein Labclinc Dye for in vivo Imaging, *Chem. Asian J.*, 6: 1353-1357 (2011).

Samanta, A., Ultrasensitive Near-Infrared Raman Reporters for SERS-based in vivo Cancer Imaging, *Angew Chem. Int. Ed*, 50: 6089-6092 (2011).

Tang, B., "A sensitive and selective near-infrared fluorescent probe for mercuric ions and its biological imaging applications", *ChemBioChem*, 9(7): 1159-1164 (2008).

Tang, B., et al., "Highly sensitive and Selective Near-infrared fluorescent probe for zinc and its application to macrophage cells", *Chemical Communications*, 34 : 3609-3611 (2006).

You-Yun, T., et al., A novel near-infrared fluorescent probe for Zn2+, *Huasue Zuebao*, 65(13): 1229-1233 (2007).

Notification of Transmittal of the International Search Report and the Written Opinion of the International Searching Authority, or the Declaration for International Application No. PCT/SG2011/000117, titled: "Development of Phtostable Near-IR Cyanine Dyes for In Vivo Imaging", 18 pages, dated Jun. 17, 2011.

CAS Registry No. 1166833-02-8, Compound, 1 page, entered Jul. 22, 2009.

CAS Registry No. 1166832-96-7, Compound, 1 page, entered Jul. 22, 2009.

CAS Registry No. 1166832-91-2, Compound, 1 page, entered Jul. 22, 2009.

CAS Registry No. 917865-94-2, Compound, 1 page, entered Jan. 18, 2007.

Kiyose, K. et al., "Molecular Design Strategies for Near-Infrared Ratiometric Fluorescent Probes Based on the Unique Spectral Properties of Aminocyanines", *Chemistry Eur. J.*, vol. 15, pp. 9191-9200 (Jul. 31, 2009).

Bardhan, R. et al., "Fluorescence Enhancement by Au Nanostructures: Nanoshells and Nanorods", *ACS Nano*, 3(3): 744-752 (Feb. 20, 2009).

Samanta, A. et al., "Development of photostable near-infrared cyanine dyes", *Chem. Commun.*, vol. 46, pp. 7406-7408 (2010).

Das, R. et al., "Solid phase synthesis of ultra-photostable cyanine NIR dye library", *RSC Advances*, 1, pp. 573-575 (2011).

\* cited by examiner

Reagents and conditions: a) RNH$_2$, DIEA, CH$_3$CN, 80 °C, 10-60 minutes; b) CH$_3$COCl, DIEA, CH$_2$Cl$_2$, 0 °C, 15 minutes.

452    477    478    480    531

599    611    621    677    686

DEVELOPMENT OF PHOTOSTABLE NEAR-IR CYANINE DYES FOR IN VIVO IMAGING

RELATED APPLICATION(S)

This application is a continuation-in-part of International Application No. PCT/SG2011/000117, which designates the United States and was filed on Mar. 24, 2011, published in English, and claims the benefit of U.S. Provisional Application No. 61/317,109, filed on Mar. 24, 2010. The entire teachings of the above applications are incorporated herein by reference.

BACKGROUND OF THE INVENTION

Bioimaging research has focused considerable attention on near-infrared (NIR) dyes. Imaging in the NIR region (approximately 650 nm to approximately 1000 nm) enables deeper tissue penetration with lower auto-fluorescence background than does imaging in the visible range, and is, therefore, particularly suitable for in vivo studies. With the emerging interest in small animal in vivo imaging, there is an increasing need for novel NIR fluorescent probes that exhibit good photostability.

Surface-enhanced Raman spectroscopy (SERS) is an alternative to fluorescence-based spectroscopy in bioimaging, as it can minimize photobleaching, peak overlapping, and signal-to-noise ratios in complex biological systems. SERS probes take advantage of the $10^{14}$-$10^{16}$-fold scattering enhancement caused by the proximity of Raman-active molecules to the surface of metal nanoparticles. However, most of the commonly used Raman-active molecules are active in the ultraviolet (UV)-visible range, and thus have restricted potential for in vivo imaging. The advantages of imaging in the NIR region have increased interest in NIR SERS-active molecules. Although 3,3'-diethylthiatricarbocyanine (DTTC) is used as a standard in NIR SERS studies, it has only a moderate Raman intensity. There is, therefore, a need for ultrasensitive SERS probes for use in the NIR region.

SUMMARY OF THE INVENTION

The tricarbocyanine scaffold is NIR-active and can be chemically derivatized at the central carbon to yield compounds that exhibit high photostabilities and high molar extinction coefficients. Furthermore, upon adsorption to metal nanoparticles, amine-acetylated tricarbocyanine (CyNA) compounds have a stable, intense Raman signal that can be detected in vivo.

One embodiment of the present invention is a compound of structural formula (I), wherein the values and alternative values are as defined in the first, second or third embodiments, or aspects thereof, or in the values and alternative values described in the Detailed Description of the Invention.

Another embodiment of the present invention is a biosensor. The biosensor comprises a nanoparticle functionalized with a compound of structural formula (I), wherein the values and alternative values of the variables of the compound of structural formula (I) are as provided in the first, second or third embodiments, or aspects thereof, or in the values and alternative values described in the Detailed Description of the Invention.

Another embodiment of the present invention is a method of labeling a biomolecule. The method comprises treating a sample including a biomolecule to be labeled with a compound of structural formula (I), wherein L reacts with the biomolecule to be labeled to form L'-B, thereby labeling the biomolecule. The values and alternative values of the variables of the compound of structural formula (I) are as described in the fourth embodiment, or aspects thereof, or in the values and alternative values described in the Detailed Description of the Invention.

Yet another embodiment of the present invention is a method of detecting the presence of a target in a sample. The method comprises treating a sample with a compound of structural formula (I), and measuring a signal produced by the compound of structural formula (I), wherein the presence of the signal indicates the presence of a target in the sample, thereby determining whether the target is present in the sample. The values and alternative values for the variables of structural formula (I) are as described in the fifth embodiment, or aspects thereof, or in the values and alternative values described in the Detailed Description of the Invention.

The compounds of the present invention have several advantages. A CyNA derivative, CyNA-414, showed increased fluorescence intensity and superior photostability in phosphate-buffered saline (PBS) when compared to an NIR standard, IndoCyanine Green (ICG) (for chemical structures of CyNA-414 and ICG, see FIG. 5). A CyNA derivative functionalized with an N-hydroxysuccinimide (NHS) ester for bioconjugation, CyNE790 (also sometimes referred to as CyNA-4,4-OSu), also exhibited these advantages.

CyNE790 was also compared to ICG-sulfo-OSu, a commercially available succinimidyl ester of ICG (for chemical structures of CyNE790 and ICG-sulfo-OSu, see FIG. 8). CyNE790 overcomes several disadvantages associated with ICG-sulfo-OSu, including low quantum yield, poor photostability and the formation of aggregates in aqueous media, and quenching of fluorescence upon protein conjugation. In photobleaching experiments, CyNE790 was 15 times more stable than ICG-sulfo-OSu and had a greater fluorescence intensity [maximum relative fluorescence units (rfu) of CyNE790: 708; maximum rfu of ICG-sulfo-OSu: 136]. After conjugation to a monoclonal EGFR-IgG$_{2a}$ antibody, CyNE790 maintained its superior fluorescence intensity and photostability, enabling the detection of EGFR-producing cells in vivo with a significantly lower detection limit than ICG-sulfo-OSu.

Upon adsorption to gold nanoparticles, the compounds of the present invention exhibit intense SERS signals that, in many cases, exceed the signal of a standard NIR SERS reporter, 3,3'-diethylthiatricarbocyanine (DTTC) (see, for example, FIG. 15). The Raman signal of CyNAMLA-381 (represented as E9 in FIG. 15), a particularly promising amine-acetylated tricarbocyanine-lipoic acid (CyNAMLA) derivative, was 12-fold higher than the Raman signal of DTTC. The CyNAMLA-functionalized gold nanoparticles are stable for at least a month (see FIGS. 21A and 21B) and exhibit consistently intense SERS signals and very little aggregation under ambient conditions.

In vitro microscopy experiments confirmed the activity and the target specificity of antibody-conjugated CyNAMLA-based biosensors and revealed that the SERS signal obtained from scFv anti-HER2-conjugated biosensors was 1.5 times stronger than that obtained from full-length anti-HER2-conjugated biosensors. This observation suggests that biosensors employing truncated antibodies, such as scFv, have lower detection limits and comparable specificities to their full-length counterparts. Furthermore, the CyNAMLA-based biosensors can be used to detect specific targets in vivo.

DETAILED DESCRIPTION OF THE INVENTION

Values and Alternative Values for Variables

Figure 1:
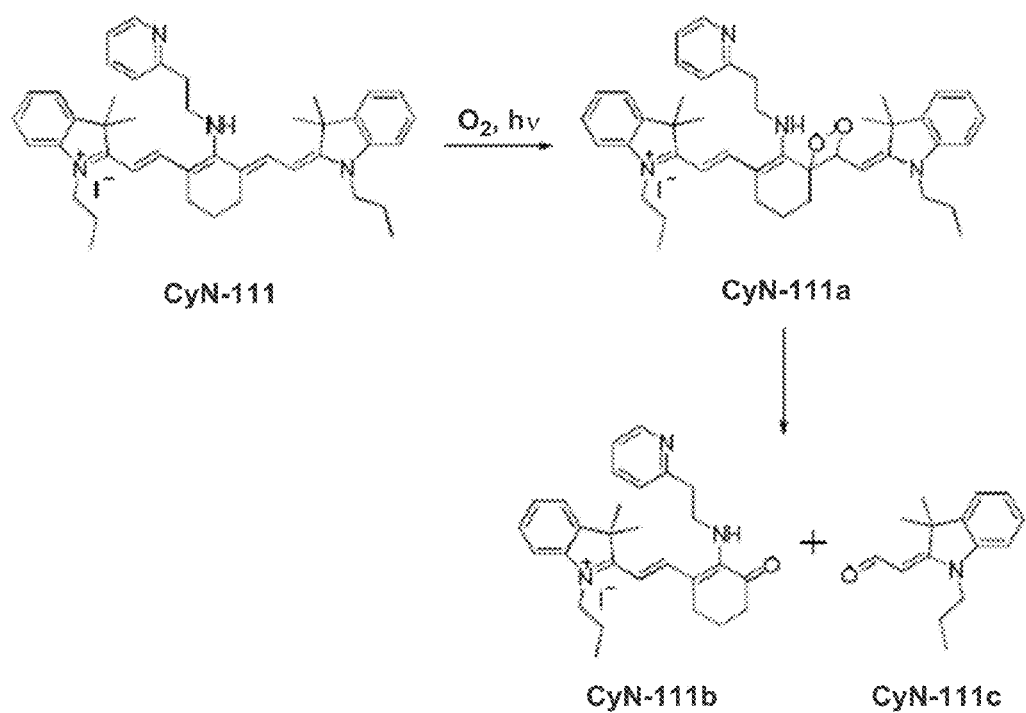
FIG. 1 shows the decomposition of CyN-111 to CyN-111b and CyN-111c upon irradiation with light.

The present invention is directed to a compound represented by structural formula (I):

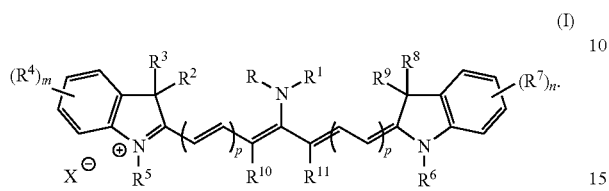

(I)

Values and alternative values for the variables in structural formula (I) and for each of the embodiments described herein are provided in the following paragraphs. It is understood that the invention encompasses all combinations of the substituent variables (i.e., R, $R^1$, $R^2$, $R^3$, etc.) defined herein.

R is ($C_1$-$C_{15}$) branched or straight-chain alkyl, ($C_3$-$C_{10}$) cycloalkyl, ($C_3$-$C_{10}$)heterocyclyl, ($C_5$-$C_{14}$)aryl, ($C_5$-$C_{14}$)hetero aryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, ($C_5$-$C_{14}$)bicycloheteroaryl($C_1$-$C_{15}$)alkyl, amino($C_1$-$C_{15}$)alkyl, ($C_1$-$C_{10}$)alkylamino($C_1$-$C_{15}$)alkyl, ($C_1$-$C_{10}$)dialkylamino($C_1$-$C_{15}$)alkyl or ($C_1$-$C_{10}$)alkylthio($C_1$-$C_{15}$)alkyl and is optionally and independently substituted with one or more substituents selected from the group consisting of halogen, ($C_1$-$C_3$)alkoxy, ($C_1$-$C_3$)alkylthio, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, nitro, cyano, sulfonato and halo($C_1$-$C_5$)alkyl.

Alternatively, R is ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, ($C_5$-$C_{14}$)bicycloheteroaryl($C_1$-$C_{15}$)alkyl, amino($C_1$-$C_{15}$)alkyl, ($C_1$-$C_{10}$)alkylamino($C_1$-$C_{15}$)alkyl or ($C_1$-$C_{10}$)dialkylamino($C_1$-$C_{15}$)alkyl.

Further, R is optionally substituted with one or more substitutents selected from the group consisting of halogen, ($C_1$-$C_3$)alkoxy, hydroxy, ($C_5$-$C_{14}$)aryl, ($C_5$-$C_{14}$)heteroaryl, ($C_1$-$C_5$)alkyl and nitro.

Alternatively, R is unsubstituted.

Further, R is ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, ($C_5$-$C_{14}$)bicycloheteroaryl($C_1$-$C_{15}$)alkyl, amino($C_1$-$C_{15}$)alkyl, ($C_1$-$C_{10}$)alkylamino($C_1$-$C_{15}$)alkyl or ($C_1$-$C_{10}$)dialkylamino($C_1$-$C_{15}$)alkyl and is optionally substituted with one or more substitutents selected from the group consisting of halogen, ($C_1$-$C_3$)alkoxy, hydroxy, ($C_5$-$C_{14}$)aryl, ($C_5$-$C_{14}$)heteroaryl, ($C_1$-$C_5$)alkyl and nitro.

R is

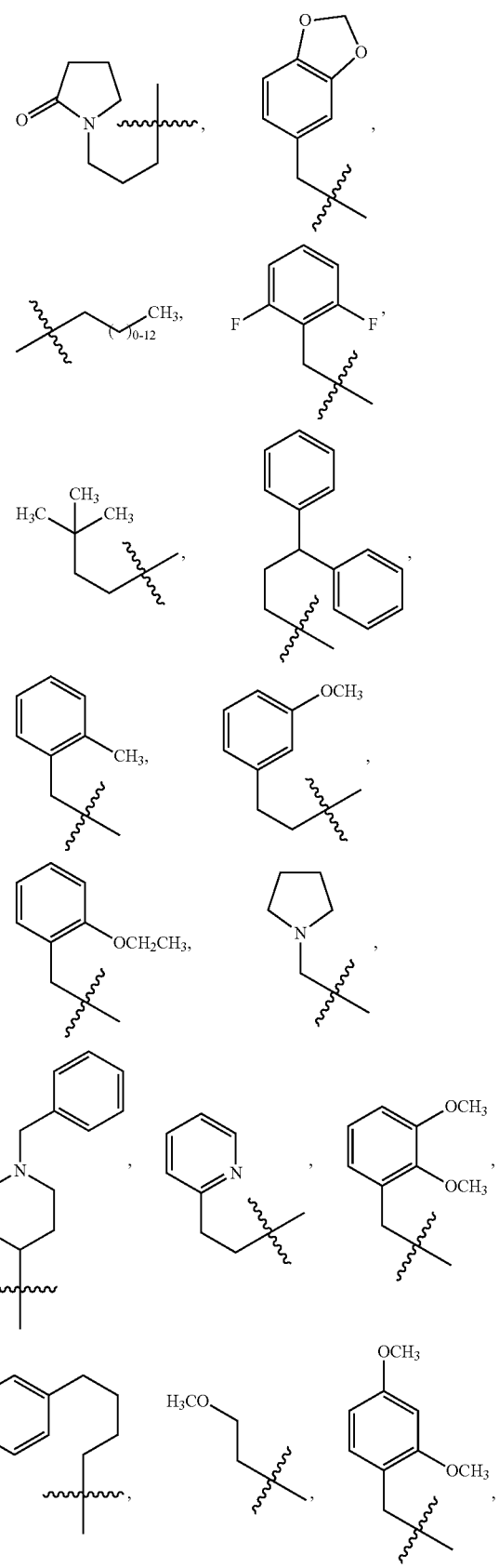

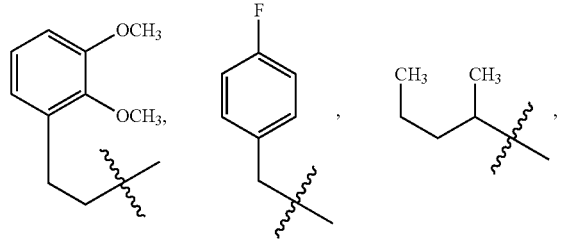
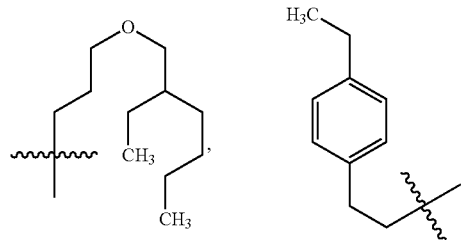
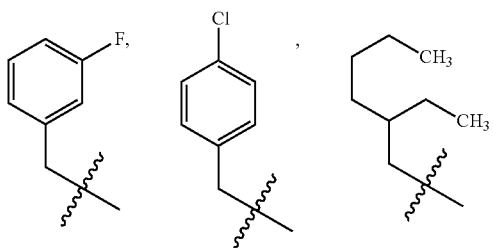
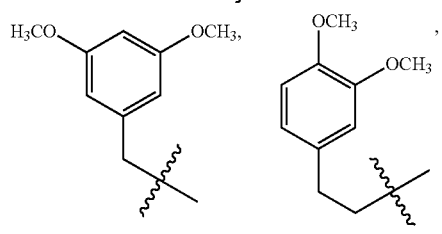
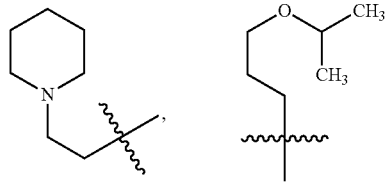
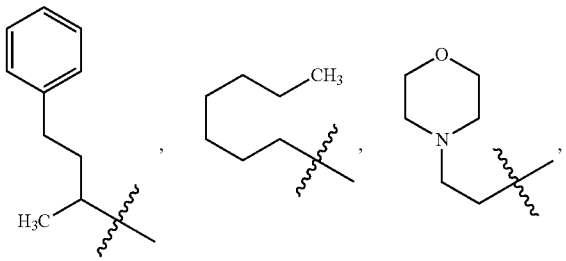
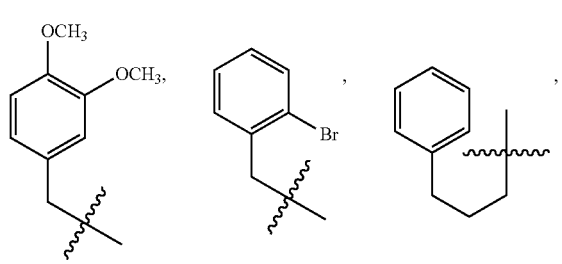
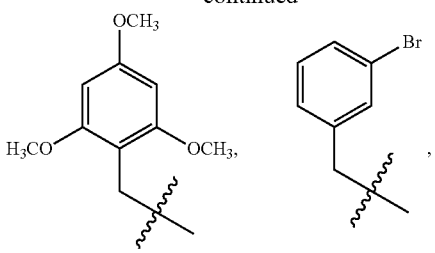
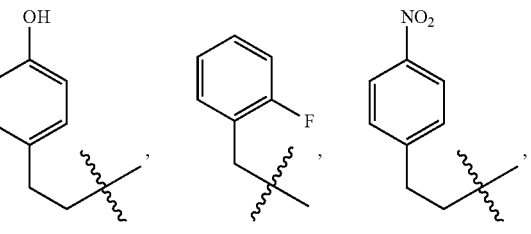
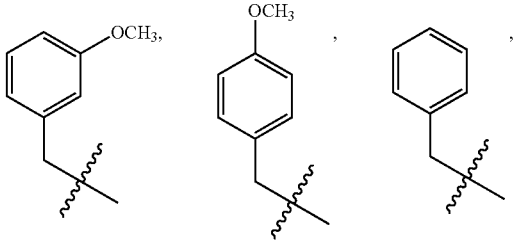
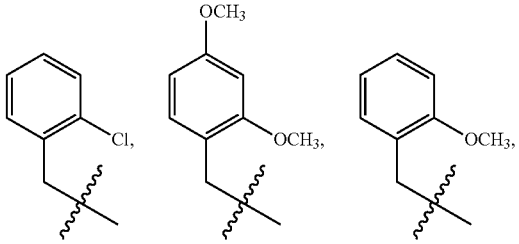
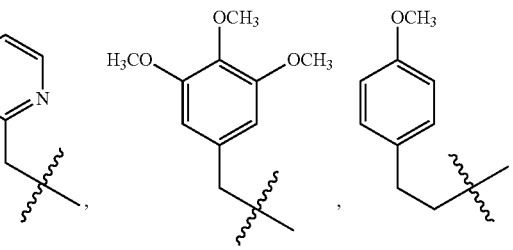
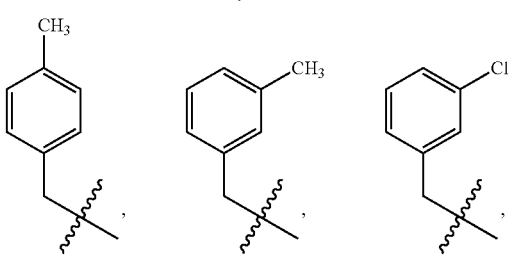
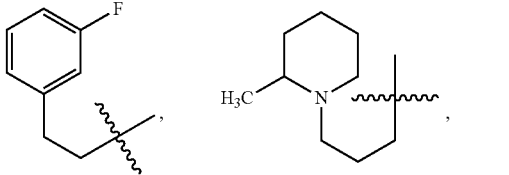

-continued
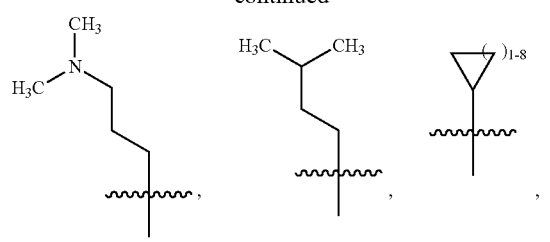
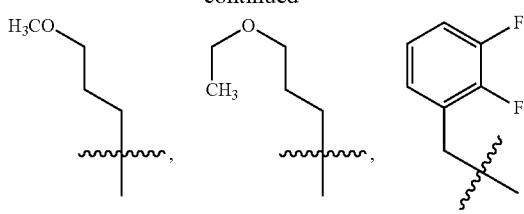
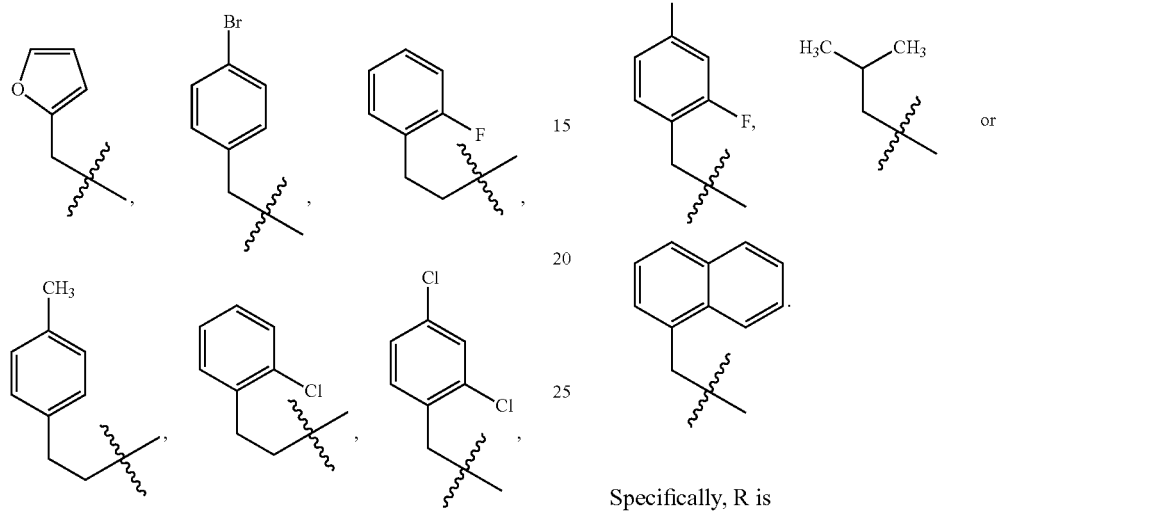
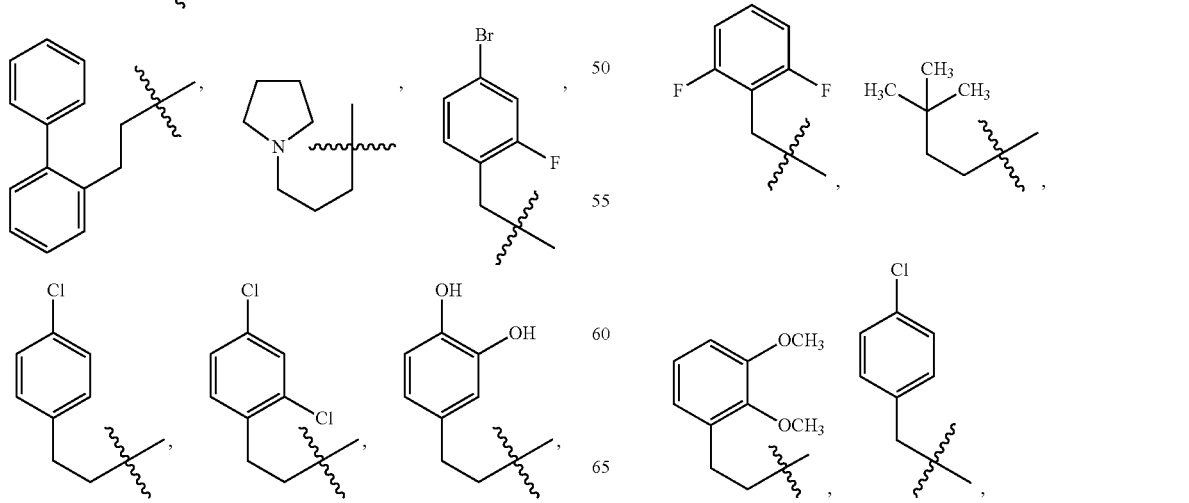
Specifically, R is
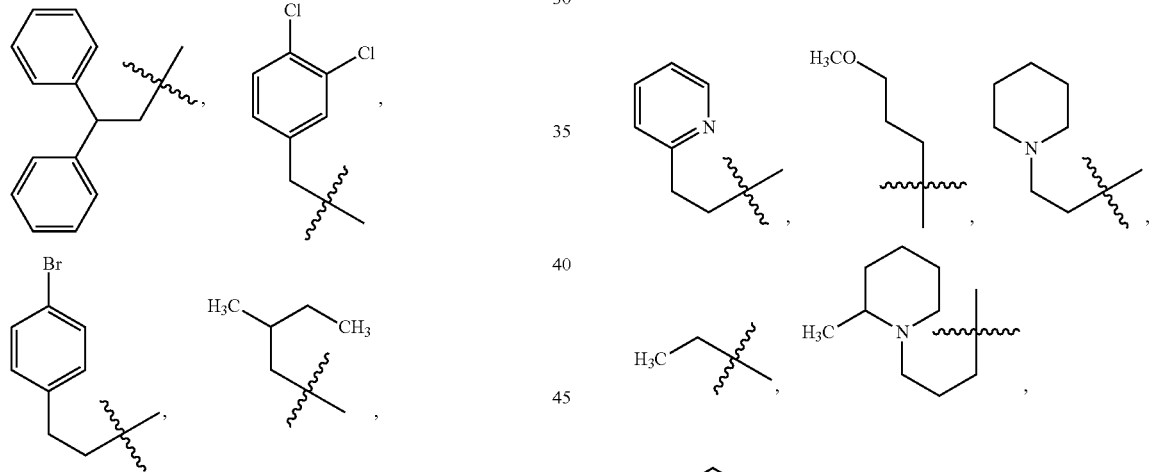

-continued

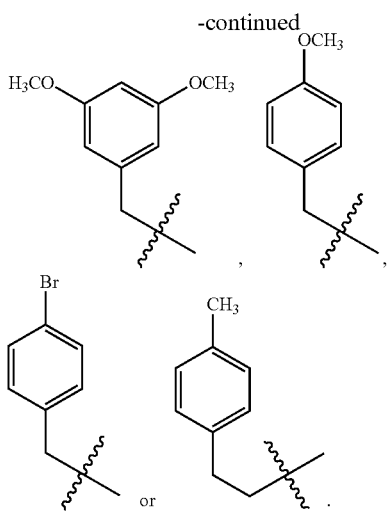

More specifically, R is

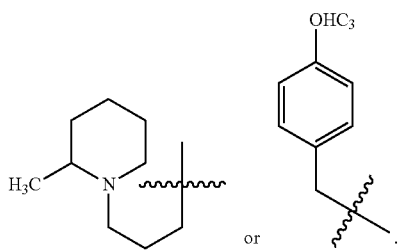

$R^1$ is —C(O)$R^{12}$, —C(O)O$R^{12}$, —C(O)N($R^{12}$)$_2$, —C(S)$R^{12}$, —C(S)O$R^{12}$, —C(O)S$R^{12}$, —C(S)S$R^{12}$ or —C(S)N($R^{12}$)$_2$, wherein each $R^{12}$ is independently hydrogen, ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —(CH$_2$)$_q$L, —(CH$_2$CH$_2$O)$_q$L, —(CH$_2$CH$_2$S)$_q$L, —(CH$_2$CH$_2$NR$^{13}$)$_q$L, —(CH$_2$)$_q$L'-B, —(CH$_2$CH$_2$O)$_q$L'-B, —(CH$_2$CH$_2$S)$_g$L'-B or —(CH$_2$CH$_2$NR$^{13}$)$_q$L'-B and is optionally and independently substituted with one or more substituents selected from the group consisting of halogen, ($C_1$-$C_3$)alkoxy, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl($C_1$-$C_5$)alkyl and halo($C_1$-$C_5$)alkyl, wherein q is an integer from 1 to 50, L and L' are each independently a linking group, each $R^{13}$ is independently hydrogen or ($C_1$-$C_5$)alkyl and B is a biomolecule. Specifically, $R^1$ is —C(O)$R^{12}$.

Alternatively, $R^1$ is —C(O)$R^{12}$, —C(O)O$R^{12}$, —C(O)N($R^{12}$)$_2$, —C(S)$R^{12}$, —C(S)O$R^{12}$, —C(O)S$R^{12}$, —C(S)S$R^{12}$ or —C(S)N($R^{12}$)$_2$, wherein each $R^{12}$ is independently hydrogen, ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —(CH$_2$)$_q$L, —(CH$_2$CH$_2$O)$_q$L, —(CH$_2$CH$_2$S)$_q$L or —(CH$_2$CH$_2$NR$^{13}$)$_q$L.

Alternatively, $R^1$ is —C(O)$R^{12}$, —C(O)O$R^{12}$, —C(O)N($R^{12}$)$_2$, —C(S)$R^{12}$, —C(S)O$R^{12}$, —C(O)S$R^{12}$, —C(S)S$R^{12}$ or —C(S)N($R^{12}$)$_2$, wherein each $R^{12}$ is independently hydrogen, ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —(CH$_2$)$_q$L'-B, —(CH$_2$CH$_2$O)$_q$L'-B, —(CH$_2$CH$_2$S)$_q$L'-B or —(CH$_2$CH$_2$NR$^{13}$)$_q$L'-B.

Further, $R^{12}$ is ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl or ($C_1$-$C_{10}$)alkylthio($C_1$-$C_{15}$)alkyl. Specifically, $R^{12}$ is ($C_1$-$C_{15}$) branched or straight-chain alkyl. More specifically, $R^{12}$ is ($C_1$-$C_5$) branched or straight-chain alkyl. Yet more specifically, $R^{12}$ is methyl.

Alternatively, $R^{12}$ is —(CH$_2$)$_q$L, —(CH$_2$CH$_2$O)$_q$L, —(CH$_2$CH$_2$S)$_q$L, —(CH$_2$CH$_2$NR$^{13}$)$_q$L, —(CH$_2$CH$_2$O)$_q$L'-B, —(CH$_2$CH$_2$S)$_q$L'-B or —(CH$_2$CH$_2$NR$^{13}$)$_q$L'-B. Specifically, $R^{12}$ is —(CH$_2$)$_q$L or —(CH$_2$)$_q$L'-B. More specifically, $R^{12}$ is —(CH$_2$)$_q$L. Alternatively, $R^{12}$ is —(CH$_2$)$_q$L'-B.

Further, q is an integer from 1 to 50. Specifically, q is an integer from 1 to 5. More specifically, q is 3.

L is amino, hydroxyl, thio, haloalkyl, N-hydroxy succinimidyl ester, sulfonato-N-hydroxy succinimidyl ester, thiocyanato, isothiocyanato, nitrophenolyl, iodoacetamidyl, maleimidyl, carboxyl, thioacetyl, sulfonato or phosphoramidityl. Specifically, L is amino, hydroxyl, thio, nitrophenolyl, N-hydroxy succinimidyl ester or sulfonato-N-hydroxy succinimidyl ester. Further, L is amino, hydroxyl or thio. Specifically, L is amino. Alternatively, L is N-hydroxy succinimidyl ester or sulfonato-N-hydroxy succinimidyl ester. Specifically, L is N-hydroxy succinimidyl ester.

L' is —NR$^{13}$—, —O—, —S—, —S(O)$_2$O—, —OP(OR$^{13}$)N(R$^{13}$)—, —OP(N(R$^{13}$)$_2$)O—, —NR$^{13}$C(O)—, —OC(O)—, —SC(O)—, —OC(S), —SC(S)—, —OC(NR$^{13}$)S—, —SC(NR$^{13}$)S—, —NR$^{13}$C(NR$^{13}$)S—, —NR$^{13}$C(O)S—, —NR$^{13}$C(S)O—, —NR$^{13}$C(S)N(R$^{13}$)—, —NR$^{13}$C(O)N(R$^{13}$)—, —OC(O)O—, —SC(O)S—, —OC(S)O—, —OC(S)S—, —SC(O)O—, —NR$^{13}$C(O)O— or —NR$^{13}$C(NR$^{13}$)N(R$^{13}$)—, wherein each $R^{13}$ is independently hydrogen or ($C_1$-$C_5$)alkyl. Specifically, L' is —NR$^{13}$C(O)—, —OC(O)— or —SC(O)—. More specifically, L' is —NR$^{13}$C(O)—.

Further, each $R^{13}$ is independently hydrogen or ($C_1$-$C_5$) alkyl. Specifically, each $R^{13}$ is hydrogen.

B is a biomolecule. Specifically, biomolecule B is a protein, a peptide, an enzyme substrate, a pharmaceutical, a ligand, a hormone, an antibody, an antigen, a hapten, a carbohydrate, an oligosaccharide, a polysaccharide, a nucleic acid, a fragment of DNA or a fragment of RNA. More specifically, biomolecule B is a protein, a ligand, an antibody, an antigen or a hapten. Yet more specifically, biomolecule B is a protein or an antibody. Alternatively, biomolecule B is a ligand.

$R^{12}$ is optionally and independently substituted with one or more substituents selected from the group consisting of halogen, ($C_1$-$C_3$)alkoxy, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl($C_1$-$C_5$)alkyl and halo($C_1$-$C_5$)alkyl. Specifically, $R^{12}$ is optionally and independently substituted with one or more substituents selected from the group consisting of halogen, $(C_1-C_3)$ alkoxy, hydroxy, amino, $(C_1-C_5)$alkylamino, $(C_1-C_5)$dialkylamino, thio, oxo, $(C_1-C_5)$alkyl, nitro, cyano and sulfonato.

Alternatively, $R^{12}$ is unsubstituted.

Alternatively, two $R^{12}$ groups, taken together with the N to which they are bound, form a $(C_3-C_{10})$heterocyclyl or $(C_5-C_{14})$heteroaryl. Specifically, two $R^{12}$ groups, taken together with the N to which they are bound, form a $(C_3-C_6)$heterocyclyl or $(C_5-C_6)$heteroaryl.

Alternatively, one $R^{12}$ group and R, taken together with the atoms to which they are bound, form a (4-10)-membered ring and the second $R^{12}$ group, if present, is as described in the preceding paragraphs. Specifically, one $R^{12}$ group and R, taken together with the atoms to which they are bound, form a (4-6)-membered ring. The values and alternative values for the second $R^{12}$ group, if present, are as described in the preceding paragraphs.

$R^2$ and $R^3$ are each independently hydrogen or $(C_1-C_{15})$alkyl, or $R^2$ and $R^3$ optionally form a (3-6)-membered ring together with the carbon atom to which they are bound. Specifically, $R^2$ and $R^3$ are each $(C_1-C_{15})$alkyl. More specifically, $R^2$ and $R^3$ are each methyl. Alternatively, $R^2$ and $R^3$ optionally form a (5-6)-membered ring together with the carbon atom to which they are bound.

$R^5$ and $R^6$ are each independently branched or straight-chain $(C_1-C_{15})$alkyl, $(C_3-C_{10})$cycloalkyl, $(C_3-C_{10})$heterocyclyl, $(C_5-C_{14})$aryl, $(C_5-C_{14})$heteroaryl, $(C_5-C_{14})$aryl$(C_1-C_{15})$alkyl, $(C_5-C_{14})$heteroaryl$(C_1-C_{15})$alkyl, $(C_1-C_{10})$alkoxy$(C_1-C_{15})$alkyl, $(C_3-C_{15})$heterocyclyl$(C_1-C_{15})$alkyl, $(C_3-C_{15})$cycloalkyl$(C_1-C_{15})$alkyl, amino$(C_1-C_{15})$alkyl, $(C_1-C_{10})$alkylthio$(C_1-C_{15})$alkyl, $-(CH_2)_qL$, $-(CH_2CH_2O)_qL$, $-(CH_2CH_2S)_qL$, $-(CH_2CH_2NR^{13})_qL$, $-(CH_2)_qL'$-B, $-(CH_2CH_2O)_qL'$-B, $-(CH_2CH_2S)_qL'$-B or $-(CH_2CH_2NR^{13})_qL'$-B, wherein each $R^5$ and $R^6$ is optionally and independently substituted with one or more substituents selected from the group consisting of halogen, $(C_1-C_3)$alkoxy, $(C_1-C_3)$alkylthio, hydroxy, $(C_5-C_{14})$aryl, $(C_5-C_{14})$heteroaryl, $(C_3-C_{15})$cyclo alkyl, $(C_3-C_{15})$heterocyclyl, amino, $(C_1-C_5)$alkylamino, $(C_1-C_5)$dialkylamino, thio, oxo, $(C_1-C_5)$alkyl, $(C_5-C_{14})$aryl$(C_1-C_5)$alkyl, $(C_5-C_{14})$heteroaryl$(C_1-C_5)$alkyl, nitro, cyano, sulfonato, hydroxyl$(C_1-C_5)$alkyl and halo$(C_1-C_5)$alkyl. The values and alternative values of L, L', $R^{13}$ and B are as described in the preceding paragraphs.

Further, $R^5$ and $R^6$ are each independently branched or straight-chain $(C_1-C_{15})$alkyl, $(C_3-C_{10})$cyclo alkyl, $(C_3-C_{10})$heterocyclyl, $(C_5-C_{14})$aryl, $(C_5-C_{14})$heteroaryl, $(C_5-C_{14})$aryl$(C_1-C_{15})$alkyl, $(C_5-C_{14})$heteroaryl$(C_1-C_{15})$alkyl, $(C_1-C_{10})$alkoxy$(C_1-C_{15})$alkyl, $(C_3-C_{15})$heterocyclyl$(C_1-C_{15})$alkyl, $(C_3-C_{15})$cycloalkyl$(C_1-C_{15})$alkyl, amino$(C_1-C_{15})$alkyl, $(C_1-C_{10})$alkylthio$(C_1-C_{15})$alkyl, $-(CH_2)_qL$, $-(CH_2CH_2O)_qL$, $-(CH_2CH_2S)_qL$, $-(CH_2CH_2NR^{13})_qL$, $-(CH_2)_qL'$-B, $-(CH_2CH_2O)_qL'$-B, $-(CH_2CH_2S)_qL'$-B or $-(CH_2CH_2NR^{13})_qL'$-B. Specifically, $R^5$ and $R^6$ are each independently branched or straight-chain $(C_1-C_{15})$alkyl, $-(CH_2)_qL$ or $-(CH_2)_qL'$-B. More specifically, one of $R^5$ and $R^6$ is branched or straight-chain $(C_1-C_{15})$alkyl and one of $R^5$ and $R^6$ is $-(CH_2)_qL$ or $-(CH_2)_qL'$-B. The values and alternative values of L, L', $R^{13}$ and B are as described in the preceding paragraphs.

Alternatively, $R^5$ and $R^6$ are each branched or straight-chain $(C_1-C_{15})$alkyl, $-(CH_2)_qL$ or $-(CH_2)_qL'$-B. More specifically, $R^5$ and $R^6$ are each branched or straight-chain $(C_1-C_{15})$alkyl. The values and alternative values of L, L' and B are described in the preceding paragraphs.

Further, $R^5$ and $R^6$ are each independently branched or straight-chain $(C_1-C_{15})$alkyl, $(C_3-C_{10})$cyclo alkyl, $(C_3-C_{10})$heterocyclyl, $(C_5-C_{14})$aryl, $(C_5-C_{14})$heteroaryl, $(C_5-C_{14})$aryl$(C_1-C_{15})$alkyl, $(C_5-C_{14})$heteroaryl$(C_1-C_{15})$alkyl, $(C_1-C_{10})$alkoxy$(C_1-C_{15})$alkyl, $(C_3-C_{15})$heterocyclyl$(C_1-C_{15})$alkyl, $(C_3-C_{15})$cycloalkyl$(C_1-C_{15})$alkyl, amino$(C_1-C_{15})$alkyl, $(C_1-C_{10})$alkylthio$(C_1-C_{15})$alkyl, $-(CH_2)_qL$, $-(CH_2CH_2O)_qL$, $-(CH_2CH_2S)_qL$ or $-(CH_2CH_2NR^{13})_qL$.

Alternatively, $R^5$ and $R^6$ are each independently branched or straight-chain $(C_1-C_{15})$alkyl, $(C_3-C_{10})$cycloalkyl, $(C_3-C_{10})$heterocyclyl, $(C_5-C_{14})$aryl, $(C_5-C_{14})$heteroaryl, $(C_5-C_{14})$aryl$(C_1-C_{15})$alkyl, $(C_5-C_{14})$heteroaryl$(C_1-C_{15})$alkyl, $(C_1-C_{10})$alkoxy$(C_1-C_{15})$alkyl, $(C_3-C_{15})$heterocyclyl$(C_1-C_{15})$alkyl, $(C_3-C_{15})$cycloalkyl$(C_1-C_{15})$alkyl, amino$(C_1-C_{15})$alkyl, $(C_1-C_{10})$alkylthio$(C_1-C_{15})$alkyl, $-(CH_2)_qL'$-B, $-(CH_2CH_2O)_qL'$-B, $-(CH_2CH_2S)_qL'$-B or $-(CH_2CH_2NR^{13})_qL'$-B.

Each $R^5$ and $R^6$ is optionally and independently substituted with one or more substituents selected from the group consisting of halogen, $(C_1-C_3)$alkoxy, $(C_1-C_3)$alkylthio, hydroxy, $(C_5-C_{14})$aryl, $(C_5-C_{14})$heteroaryl, $(C_3-C_{15})$cycloalkyl, $(C_3-C_{15})$heterocyclyl, amino, $(C_1-C_5)$alkylamino, $(C_1-C_5)$dialkylamino, thio, oxo, $(C_1-C_5)$alkyl, $(C_5-C_{14})$aryl$(C_1-C_5)$alkyl, $(C_5-C_{14})$heteroaryl$(C_1-C_5)$alkyl, nitro, cyano, sulfonato, hydroxyl$(C_1-C_5)$alkyl and halo$(C_1-C_5)$alkyl. Specifically, each $R^5$ and $R^6$ is optionally and independently substituted with halogen, $(C_1-C_3)$alkoxy, $(C_1-C_3)$alkylthio, hydroxy, amino, $(C_1-C_5)$alkylamino, $(C_1-C_5)$dialkylamino, thio, oxo, cyano or sulfonato.

Alternatively, $R^5$ and $R^6$ are each unsubstituted.

$R^8$ and $R^9$ are each independently hydrogen or $(C_1-C_{15})$alkyl, or $R^8$ and $R^9$, together with the carbon atoms to which they are bound, optionally form a (3-6)-membered ring. Specifically, $R^8$ and $R^9$ are each $(C_1-C_{15})$alkyl. More specifically, $R^8$ and $R^9$ are each methyl. Alternatively, $R^8$ and $R^9$, together with the carbon atoms to which they are bound, optionally form a (5-6)-membered ring.

Each $R^4$ and $R^7$ is independently halo, $(C_1-C_5)$alkyl, $(C_5-C_{14})$aryl, $(C_5-C_{14})$heteroaryl, $(C_3-C_{10})$cycloalkyl, $(C_3-C_{10})$heterocyclyl, hydroxy, carboxylate, nitro, cyano, amino, $(C_1-C_5)$alkylamino, $(C_1-C_5)$dialkylamino, $(C_1-C_3)$alkoxy, $(C_1-C_3)$alkylthio, thio, sulfonato or halo$(C_1-C_5)$alkyl. Specifically, each $R^4$ and $R^7$ is independently halo, hydroxy, carboxylate, nitro, cyano, amino, $(C_1-C_5)$alkylamino, $(C_1-C_5)$dialkylamino, $(C_1-C_3)$alkoxy, $(C_1-C_3)$alkylthio, thio, sulfonato or halo$(C_1-C_5)$alkyl.

Alternatively, each $R^4$ and $R^7$ is independently halo, $(C_1-C_5)$alkyl, $(C_5-C_{14})$aryl, $(C_5-C_{14})$heteroaryl, $(C_3-C_{10})$cycloalkyl, $(C_3-C_{10})$heterocyclyl, hydroxy, carboxylate, nitro, cyano, amino, $(C_1-C_5)$alkylamino, $(C_1-C_5)$dialkylamino, $(C_1-C_3)$alkoxy, $(C_1-C_3)$alkylthio, thio, sulfonato or halo$(C_1-C_5)$alkyl, wherein each of the independently selected $R^4$ groups corresponds to an $R^7$ group at the same ring position having the same value. Specifically, each $R^4$ and $R^7$ is independently halo, hydroxy, carboxylate, nitro, cyano, amino, $(C_1-C_5)$alkylamino, $(C_1-C_5)$dialkylamino, $(C_1-C_3)$alkoxy, $(C_1-C_3)$alkylthio, thio, sulfonato or halo$(C_1-C_5)$alkyl, wherein each of the independently selected $R^4$ groups corresponds to an $R^7$ group at the same ring position having the same value.

Alternatively, two $R^4$ groups or two $R^7$ groups, together with the carbon atoms to which they are bound, each independently form a $(C_4-C_{10})$cycloalkyl, $(C_4-C_{10})$heterocyclyl, $(C_5-C_{14})$aryl or $(C_5-C_{14})$heteroaryl. Specifically, two $R^4$ groups or two $R^7$ groups, together with the carbon atoms to which they are bound, each independently form a $(C_5-C_6)$cycloalkyl, $(C_5-C_6)$heterocyclyl, $(C_5-C_6)$aryl or $(C_5-C_6)$heteroaryl.

Alternatively, two $R^4$ groups and two $R^7$ groups each form a $(C_4-C_{10})$cycloalkyl, $(C_4-C_{10})$heterocyclyl, $(C_5-C_{14})$aryl or ($C_5$-$C_{14}$)heteroaryl. Specifically, two $R^4$ groups and two $R^7$ groups each form a ($C_5$-$C_6$)cycloalkyl, ($C_5$-$C_6$)heterocyclyl, ($C_5$-$C_6$)aryl or ($C_5$-$C_6$)heteroaryl.

$R^{10}$ and $R^{11}$ are each independently hydrogen, ($C_1$-$C_{15}$) alkyl, or optionally, together with the carbon atoms to which they are bound, form a 5- or 6-membered ring. Specifically, $R^{10}$ and $R^{11}$ are each hydrogen or ($C_1$-$C_5$)alkyl. Alternatively, $R^{10}$ and $R^{11}$, together with the carbon atoms to which they are bound, form a 6-membered ring. Specifically, $R^{10}$ and $R^{11}$, together with the carbon atoms to which they are bound, form a cyclohexene ring.

Further, m and n are each independently an integer from 0 to 4. Specifically, m and n are each independently 0, 1 or 2.

Alternatively, m and n are each an integer from 0 to 4. Specifically, m and n are each 0, 1 or 2. More specifically, m and n are each 0.

Further, p is an integer from 0 to 3. Specifically, p is 0, 1 or 2. More specifically, p is 1.

X is an anion. Examples of anions are halide, trifluoroacetate, acetate, benzenesulfonate, benzoate, perchlorate, sulfonate, bicarbonate, carbonate, citrate, mesylate, methylsulfate, nitrate, phosphate/diphosphate, and sulfate. Specifically, X is halide, trifluoroacetate, acetate, sulfonate or perchlorate. More specifically, X is trifluoroacetate or halide. Yet more specifically, X is chloride, bromide or iodide. Alternatively, X is trifluoroacetate.

At least one of $R^5$, $R^6$ and $R^{12}$ is —$(CH_2)_qL$, —$(CH_2CH_2O)_qL$, —$(CH_2CH_2S)_qL$, —$(CH_2CH_2NR^{13})_qL$, —$(CH_2)_qL'$-B, —$(CH_2CH_2O)_qL'$-B, —$(CH_2CH_2S)_qL'$-B or —$(CH_2CH_2NR^{13})_qL'$-B. Specifically, one of $R^5$, $R^6$ and $R^{12}$ is —$(CH_2)_qL$, —$(CH_2CH_2O)_qL$, —$(CH_2CH_2S)_qL$, —$(CH_2CH_2NR^{13})_qL$, —$(CH_2)_qL'$-B, —$(CH_2CH_2O)_qL'$-B, —$(CH_2CH_2S)_qL'$-B or —$(CH_2CH_2NR^{13})_qL'$-B. More specifically, one of $R^5$, $R^6$ and $R^{12}$ is —$(CH_2)_qL$ or —$(CH_2)_qL'$-B. Yet more specifically, $R^{12}$ is —$(CH_2)_qL$ or —$(CH_2)_qL'$-B. Alternatively, $R^5$ or $R^6$ is —$(CH_2)_qL$ or —$(CH_2)_qL'$-B. The values and alternative values for L, L' and B are as described in the preceding paragraphs.

Alternatively, at least one of $R^5$, $R^6$ and $R^{12}$ is —$(CH_2)_qL$, —$(CH_2CH_2O)_qL$, —$(CH_2CH_2S)_qL$ or —$(CH_2CH_2NR^{13})_qL$. Alternatively, at least one of $R^5$, $R^6$ and $R^{12}$ is —$(CH_2)_qL'$-B, —$(CH_2CH_2O)_qL'$-B, —$(CH_2CH_2S)_qL'$-B or —$(CH_2CH_2NR^{13})_qL'$-B. The values and alternative values for L, L' and B are as described in the preceding paragraphs.

A first embodiment of the present invention is a compound represented by structural formula (I), wherein:

R is ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, ($C_5$-$C_{14}$)bicycloheteroaryl($C_1$-$C_{15}$)alkyl, amino($C_1$-$C_{15}$)alkyl, ($C_1$-$C_{10}$)alkylamino($C_1$-$C_{15}$)alkyl, ($C_1$-$C_{10}$)dialkylamino($C_1$-$C_{15}$)alkyl or ($C_1$-$C_{10}$)alkylthio($C_1$-$C_{15}$)alkyl and is optionally and independently substituted with one or more substituents selected from the group consisting of halogen, ($C_1$-$C_3$)alkoxy, ($C_1$-$C_3$)alkylthio, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, nitro, cyano, sulfonato and halo($C_1$-$C_5$)alkyl;

$R^1$ is —$C(O)R^{12}$—$C(O)N(R^{12})_2$, —$C(S)R^{12}$, —$C(S)OR^{12}$, —$C(O)SR^{12}$, —$C(S)SR^{12}$ or —$C(S)N(R^{12})_2$, wherein each $R^{12}$ is independently hydrogen, ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —$(CH_2)_qL$, —$(CH_2CH_2O)_qL$, —$(CH_2CH_2S)_qL$, —$(CH_2CH_2NR^{13})_qL$, —$(CH_2)_qL'$-B, —$(CH_2CH_2O)_qL'$-B, —$(CH_2CH_2S)_qL'$-B or —$(CH_2CH_2NR^{13})_qL'$-B and is optionally and independently substituted with one or more substituents selected from the group consisting of halogen, ($C_1$-$C_3$)alkoxy, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl($C_1$-$C_5$)alkyl and halo($C_1$-$C_5$)alkyl, wherein q is an integer from 1 to 50, L and L' are each independently a linking group, each $R^{13}$ is independently hydrogen or ($C_1$-$C_5$)alkyl and B is a biomolecule;

or two $R^{12}$ groups, taken together with the N to which they are bound, form a ($C_3$-$C_{10}$)heterocyclyl or ($C_5$-$C_{14}$)heteroaryl;

or one $R^{12}$ group and R, taken together with the atoms to which they are bound, form a (4-10)-membered ring and the second $R^{12}$ group, if present, is as defined above;

$R^2$ and $R^3$ are each independently hydrogen or ($C_1$-$C_{15}$) alkyl, or $R^2$ and $R^3$ optionally form a (3-6)-membered ring together with the carbon atom to which they are bound;

$R^5$ and $R^6$ are each independently branched or straight-chain ($C_1$-$C_{15}$)alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{15}$)heterocyclyl($C_1$-$C_{15}$)alkyl, ($C_3$-$C_{15}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —$(CH_2)_qL$, —$(CH_2CH_2O)_qL$, —$(CH_2CH_2S)_qL$, —$(CH_2CH_2NR^{13})_qL$, —$(CH_2)_qL'$-B, —$(CH_2CH_2O)_qL'$-B, —$(CH_2CH_2S)_qL'$-B or —$(CH_2CH_2NR^{13})_qL'$-B, wherein each $R^5$ and $R^6$ is optionally and independently substituted with one or more substituents selected from the group consisting of halogen, ($C_1$-$C_3$) alkoxy, ($C_1$-$C_3$)alkylthio, hydroxy, ($C_5$-$C_{14}$)aryl, ($C_5$-$C_{14}$)heteroaryl, ($C_3$-$C_{15}$)cycloalkyl, ($C_3$-$C_{15}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl ($C_1$-$C_5$)alkyl, nitro, cyano, sulfonato, hydroxyl($C_1$-$C_5$)alkyl and halo($C_1$-$C_5$)alkyl;

$R^8$ and $R^9$ are each independently hydrogen or ($C_1$-$C_{15}$) alkyl, or $R^8$ and $R^9$ optionally form a (3-6)-membered ring together with the carbon atom to which they are bound;

$R^4$ and $R^7$ are each independently halo, ($C_1$-$C_5$)alkyl, ($C_5$-$C_{14}$)aryl, ($C_5$-$C_{14}$)heteroaryl, ($C_3$-$C_{10}$)cycloalkyl, ($C_3$-$C_{10}$)heterocyclyl, hydroxy, carboxylate, nitro, cyano, amino, ($C_1$-$C_5$)alkylamino, ($C_1$-$C_5$)dialkylamino, ($C_1$-$C_3$)alkoxy, ($C_1$-$C_3$)alkylthio, thio, sulfonato or halo($C_1$-$C_5$)alkyl, or two $R^4$ or two $R^7$ together with the carbon atoms to which they are bound, form a ($C_4$-$C_{10}$)cycloalkyl, ($C_4$-$C_{10}$)heterocyclyl, ($C_5$-$C_{14}$)aryl or ($C_5$-$C_{14}$)heteroaryl;

$R^{10}$ and $R^{11}$ are each independently hydrogen, ($C_1$-$C_{15}$) alkyl, or optionally, together with the carbon atoms to which they are bound, form a 5- or 6-membered ring;

m and n are each independently an integer from 0 to 4;

p is an integer from 0 to 3; and

X is an anion, wherein at least one of $R^5$, $R^6$ and $R^{12}$ is —$(CH_2)_qL$, —$(CH_2CH_2O)_qL$, —$(CH_2CH_2S)_qL$, —$(CH_2CH_2NR^{13})_qL$, —$(CH_2CH_2O)_qL'$-B, —$(CH_2CH_2S)_gL'$-B or —$(CH_2CH_2NR^{13})_qL'$-B.

In one aspect of the first embodiment, R is ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-

$C_{14}$)aryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$) alkyl, ($C_5$-$C_{14}$)bicycloheteroaryl($C_1$-$C_{15}$)alkyl, amino($C_1$-$C_{15}$)alkyl, ($C_1$-$C_{10}$)alkylamino($C_1$-$C_{15}$)alkyl or ($C_1$-$C_{10}$) dialkylamino($C_1$-$C_{15}$)alkyl, wherein the values and alternative values for the remaining variables are as defined in the first embodiment or in the values and alternative values described above.

In a second aspect of the first embodiment, R is substituted with one or more substitutents selected from the group consisting of halogen, ($C_1$-$C_3$)alkoxy, hydroxy, ($C_5$-$C_{14}$)aryl, ($C_5$-$C_{14}$)heteroaryl, ($C_1$-$C_5$)alkyl and nitro, wherein the values and alternative values for the remaining variables are as defined in the first embodiment or in the values and alternative values described above.

In a third aspect of the first embodiment, R is unsubstituted, wherein the values and alternative values for the remaining variables are as defined in the first embodiment or in the values and alternative values described above.

In a fourth aspect of the first embodiment, R is ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$) alkyl, ($C_5$-$C_{14}$)bicycloheteroaryl($C_1$-$C_{15}$)alkyl, amino($C_1$-$C_{15}$)alkyl, ($C_1$-$C_{10}$)alkylamino($C_1$-$C_{15}$)alkyl or ($C_1$-$C_{10}$) dialkylamino($C_1$-$C_{15}$)alkyl and is optionally substituted with one or more substitutents selected from the group consisting of halogen, ($C_1$-$C_3$)alkoxy, hydroxy, ($C_5$-$C_{14}$)aryl, ($C_5$-$C_{14}$) heteroaryl, ($C_1$-$C_5$)alkyl and nitro, wherein the values and alternative values for the remaining variables are as defined in the first embodiment or in the values and alternative values described above.

In a fifth aspect of the first embodiment, R is

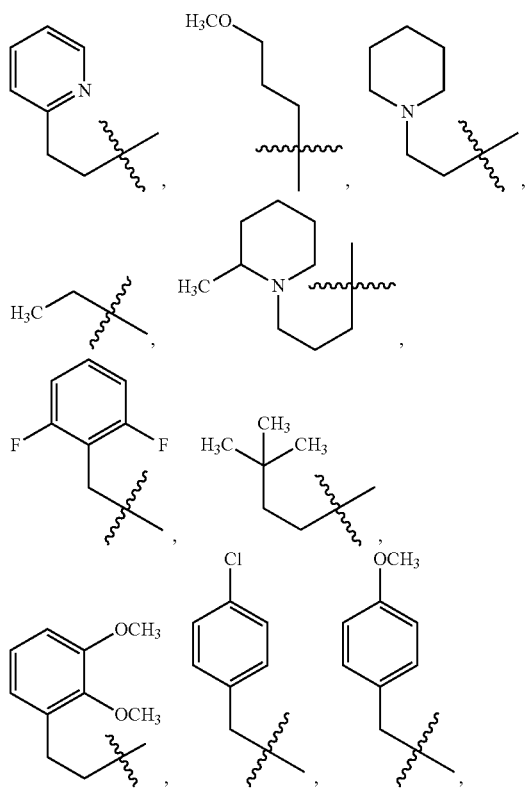

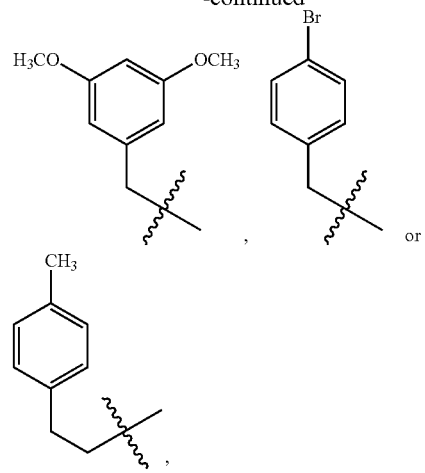

wherein the values and alternative values for the remaining variables are as defined in the first embodiment or in the values and alternative values described above.

In a sixth aspect of the first embodiment, $R^1$ is —C(O)$R^{12}$ and p is 1, wherein the values and alternative values for the remaining variables are as defined in the first embodiment or in the values and alternative values described above.

In a seventh aspect of the first embodiment, $R^5$, $R^6$ or $R^{12}$ is —(CH$_2$)$_q$L or —(CH$_2$)$_q$L'-B, wherein the values and alternative values for the remaining variables are as defined in the first embodiment or in the values and alternative values described above.

In an eighth aspect of the first embodiment, L is amino, N-hydroxy succinimidyl ester or sulfonato-N-hydroxy succinimidyl ester, wherein the values and alternative values for the remaining variables are as defined in the first embodiment or in the values and alternative values described above.

In a ninth aspect of the first embodiment, L' is —NR$^{13}$C (O)—, —OC(O)— or —SC(O)—, wherein the values and alternative values for the remaining variables are as defined in the first embodiment or in the values and alternative values described above.

In a tenth aspect of the first embodiment, each $R^4$ and $R^7$ is independently halo, hydroxy, carboxylate, nitro, cyano, amino, ($C_1$-$C_5$)alkylamino, ($C_1$-$C_5$)dialkylamino, ($C_1$-$C_3$) alkoxy, ($C_1$-$C_3$)alkylthio, thio, sulfonato or halo($C_1$-$C_5$)alkyl, wherein each of the independently selected $R^4$ groups corresponds to an $R^7$ group at the same ring position having the same value and wherein the values and alternative values for the remaining variables are as defined in the first embodiment or in the values and alternative values described above.

In an eleventh aspect of the first embodiment, $R^2$, $R^3$, $R^8$ and $R^9$ are each methyl, wherein the values and alternative values for the remaining variables are as defined in the first embodiment or in the values and alternative values described above.

In a twelfth aspect of the first embodiment, $R^{10}$ and $R^{11}$ are each hydrogen or ($C_1$-$C_5$)alkyl or, together with the carbon atoms to which they are bound, form a cyclohexene ring, wherein the values and alternative values for the remaining variables are as defined in the first embodiment or in the values and alternative values described above.

In a thirteenth aspect of the first embodiment, $R^1$ is —C(O) $R^{12}$ and $R^{12}$ is —(CH$_2$)$_q$L or —(CH$_2$)$_q$L'-B, wherein the values and alternative values for the remaining variables are as defined in the first embodiment or in the values and alternative values described above.

In a fourteenth aspect of the first embodiment, $R^1$ is —C(O)$R^{12}$, —C(O)O$R^{12}$, —C(O)N($R^{12}$)$_2$, —C(S)$R^{12}$, —C(S)O$R^{12}$, —C(O)S$R^{12}$, —C(S)S$R^{12}$ or —C(S)N($R^{12}$)$_2$, wherein each $R^{12}$ is independently hydrogen, ($C_1$-$C_{15}$) branched or straight-chain alkyl, ($C_3$-$C_{10}$)cyclo alkyl, ($C_3$-$C_{10}$)heterocyclyl, ($C_1$-$C_{14}$)aryl, ($C_5$-$C_{14}$)heteroaryl, ($C_5$-$C_{14}$)aryl($C_1$-$C_{15}$)alkyl, ($C_5$-$C_{14}$)hetero aryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —(CH$_2$)$_q$L, —(CH$_2$CH$_2$O)$_q$L, —(CH$_2$CH$_2$S)$_q$L or —(CH$_2$CH$_2$NR$^{13}$)$_q$L and is optionally and independently substituted with one or more substituents selected from the group consisting of halogen, ($C_1$-$C_3$) alkoxy, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl($C_1$-$C_5$)alkyl and halo($C_1$-$C_5$)alkyl, wherein q is an integer from 1 to 50, L is a linking group, and each $R^{13}$ is independently hydrogen or ($C_1$-$C_5$) alkyl; and $R^5$ and $R^6$ are each independently branched or straight-chain ($C_1$-$C_{15}$)alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{15}$)heterocyclyl($C_1$-$C_{15}$)alkyl, ($C_3$-$C_{15}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —(CH$_2$)$_q$L, —(CH$_2$CH$_2$O)$_q$L, —(CH$_2$CH$_2$S)$_q$L or —(CH$_2$CH$_2$NR$^{13}$)$_q$L, wherein each $R^5$ and $R^6$ is optionally and independently substituted with one or more substituents selected from the group consisting of halogen, ($C_1$-$C_3$)alkoxy, ($C_1$-$C_3$)alkylthio, hydroxy, ($C_5$-$C_{14}$)aryl, ($C_5$-$C_{14}$)heteroaryl, ($C_3$-$C_{15}$)cycloalkyl, ($C_3$-$C_{15}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl ($C_1$-$C_5$)alkyl and halo($C_1$-$C_5$)alkyl, wherein at least one of $R^5$, $R^6$ and $R^{12}$ is —(CH$_2$)$_q$L, —(CH$_2$CH$_2$O)$_q$L, —(CH$_2$CH$_2$S)$_q$L or —(CH$_2$CH$_2$NR$^{13}$)$_q$L and wherein the values and alternative values for the remaining variables are as defined in the first embodiment or in the values and alternative values described above.

In a fifteenth aspect of the first embodiment, $R^1$ is —C(O)$R^{12}$, —C(O)O$R^{12}$, —C(O)N($R^{12}$)$_2$, —C(S)$R^{12}$, —C(S)O$R^{12}$, —C(O)S$R^{12}$, —C(S)S$R^{12}$ or —C(S)N($R^{12}$)$_2$, wherein each $R^{12}$ is independently hydrogen, ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$) alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —(CH$_2$)$_q$L'-B, —(CH$_2$CH$_2$O)$_q$L'-B, —(CH$_2$CH$_2$S)$_q$L'-B or —(CH$_2$CH$_2$NR$^{13}$)$_q$L'-B and is optionally and independently substituted with one or more substituents selected from the group consisting of halogen, ($C_1$-$C_3$)alkoxy, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl($C_1$-$C_5$)alkyl and halo($C_1$-$C_5$)alkyl, wherein q is an integer from 1 to 50, L' is a linking group, each $R^{13}$ is independently hydrogen or ($C_1$-$C_5$)alkyl and B is a biomolecule; and $R^5$ and $R^6$ are each independently branched or straight-chain ($C_1$-$C_{15}$)alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{15}$)heterocyclyl($C_1$-$C_{15}$)alkyl, ($C_3$-$C_{15}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —(CH$_2$)$_q$L'-B, —(CH$_2$CH$_2$O)$_q$L'-B, —(CH$_2$CH$_2$S)$_q$L'-B or —(CH$_2$CH$_2$NR$^{13}$)$_q$L'-B, wherein each $R^5$ and $R^6$ is optionally and independently substituted with one or more substituents selected from the group consisting of halogen, ($C_1$-$C_3$) alkoxy, ($C_1$-$C_3$)alkylthio, hydroxy, ($C_5$-$C_{14}$)aryl, ($C_5$-$C_{14}$)heteroaryl, ($C_3$-$C_{15}$)cycloalkyl, ($C_3$-$C_{15}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl ($C_1$-$C_5$)alkyl, nitro, cyano, sulfonato, hydroxyl($C_1$-$C_5$)alkyl and halo($C_1$-$C_5$)alkyl, wherein at least one of $R^5$, $R^6$ and $R^{12}$ is —(CH$_2$)$_q$L'-B, —(CH$_2$CH$_2$O)$_q$L'-B, —(CH$_2$CH$_2$S)$_q$L'-B or —(CH$_2$CH$_2$NR$^{13}$)$_q$L'-B and wherein the values and alternative values for the remaining variables are as defined in the first embodiment or in the values and alternative values described above.

A second embodiment of the present invention is a compound represented by the following structural formula:

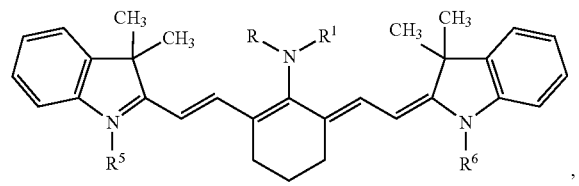

wherein the values and alternative values for the remaining variables are as defined in the first embodiment or in the values and alternative values described above.

In a first aspect of the second embodiment, $R^5$ and $R^6$ are each branched or straight-chain ($C_1$-$C_5$)alkyl, wherein the values and alternative values for the remaining variables are as defined in the first embodiment, or aspects thereof, in the second embodiment or in the values and alternative values described above.

In a second aspect of the second embodiment, $R^1$ is —C(O)$R^{12}$ and $R^{12}$ is —(CH$_2$)$_q$L or —(CH$_2$)$_q$L'-B, wherein the values and alternative values for the remaining variables are as defined in the first embodiment, or aspects thereof, in the second embodiment or in the values and alternative values described above.

In a third aspect of the second embodiment, $R^1$ is —C(O)$R^{12}$, $R^{12}$ is —(CH$_2$)$_q$L or —(CH$_2$)$_q$L'-B and $R^5$ and $R^6$ are each branched or straight-chain ($C_1$-$C_5$)alkyl, wherein the values and alternative values for the remaining variables are as defined in the first embodiment, or aspects thereof, in the second embodiment or in the values and alternative values described above.

In a fourth aspect of the second embodiment, $R^1$ is —C(O)$R^{12}$, $R^{12}$ is

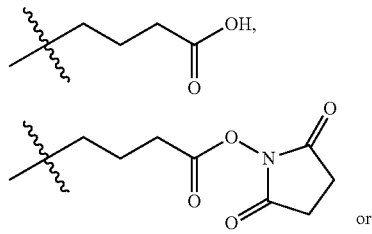

or

-continued

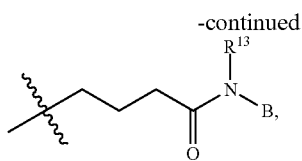

wherein the values and alternative values for the remaining variables are as defined in the first embodiment, or aspects thereof, in the second embodiment or in the values and alternative values described above.

A third embodiment of the present invention is a compound of the following structural formula:

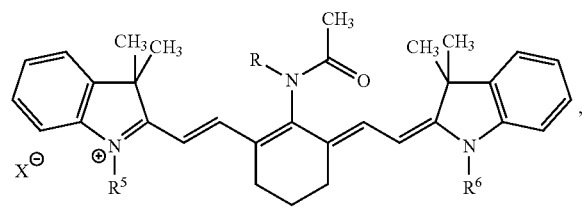

wherein the values and alternative values for the remaining variables are as defined in the first or second embodiments, or aspects thereof, or in the values and alternative values described above.

In a first aspect of the third embodiment, $R^5$ is branched or straight-chain $(C_1-C_5)$alkyl and $R^6$ is —$(CH_2)_qL$ or —$(CH_2)_qL'$-B, or $R^6$ is branched or straight-chain $(C_1-C_5)$ alkyl and $R^5$ is —$(CH_2)_qL$ or —$(CH_2)_qL'$-B, wherein the values and alternative values for the remaining variables are as defined in the first or second embodiments, or aspects thereof, in the third embodiment or in the values and alternative values described above.

In a second aspect of the third embodiment, $R^5$ is

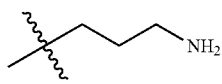 [SMILES: *CCCN]

and $R^6$ is n-propyl or $R^6$ is

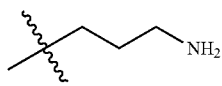

and $R^5$ is n-propyl, wherein the values and alternative values for the remaining variables are as defined in the first or second embodiments, or aspects thereof, in the third embodiment or in the values and alternative values described above.

In a third aspect of the third embodiment, $R^5$ is

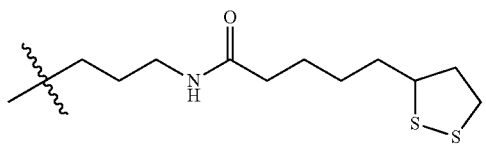 [SMILES: *CCCNC(=O)CCCCC1CCSS1]

and $R^6$ is n-propyl or $R^6$ is

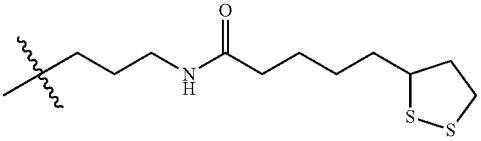 [SMILES: *CCCNC(=O)CCCCC1CCSS1]

and $R^5$ is n-propyl, wherein the values and alternative values for the remaining variables are as defined in the first or second embodiments, or aspects thereof, in the third embodiment or in the values and alternative values described above.

DEFINITIONS

As used in the description of this invention, the terms set forth below have the following definitions.

As used herein, the singular forms "a," "an" and "the" include plural referents unless the context clearly dictates otherwise. Thus, for example, reference to "a biomolecule" can include a plurality of biomolecules. Further, the plurality can comprise more than one of the same biomolecule or a plurality of different biomolecules.

"Alkyl" means an optionally substituted saturated aliphatic branched or straight-chain monovalent hydrocarbon radical having the specified number of carbon atoms. Thus, "$(C_1-C_6)$ alkyl" means a radical having from 1-6 carbon atoms in a linear or branched arrangement. "$(C_1-C_6)$alkyl" includes, for example, methyl, ethyl, propyl, isopropyl, n-butyl, tert-butyl, pentyl and hexyl.

"Alkylene" means an optionally substituted saturated aliphatic branched or straight-chain divalent hydrocarbon radical having the specified number of carbon atoms. Thus, "$(C_1-C_6)$alkylene" means a divalent saturated aliphatic radical having from 1-6 carbon atoms in a linear arrangement, e.g., —$[(CH_2)_n]$—, where n is an integer from 1 to 6. "$(C_1-C_6)$ alkylene" includes methylene, ethylene, propylene, butylene, pentylene and hexylene. Alternatively, "$(C_1-C_6)$alkylene" means a divalent saturated radical having from 1-6 carbon atoms in a branched arrangement, for example: —$[(CH_2CH_2CH_2CH_2CH(CH_3)]$—, —$[(CH_2CH_2CH_2CH_2C(CH_3)_2]$—, —$[(CH_2C(CH_3)_2CH(CH_3))]$—, and the like.

Each alkyl or alkylene in structural formula (I) is optionally and independently substituted with one or more substituents independently selected from halogen, $(C_1-C_3)$alkoxy, hydroxy, $(C_5-C_{14})$aryl, $(C_5-C_{14})$heteroaryl, $(C_3-C_{10})$cycloalkyl, $(C_3-C_{10})$heterocyclyl, amino, $(C_1-C_5)$alkylamino, $(C_1-C_5)$dialkylamino, thio, oxo, $(C_1-C_5)$alkyl, $(C_5-C_{14})$aryl $(C_1-C_5)$alkyl, $(C_5-C_{14})$heteroaryl$(C_1-C_5)$alkyl, nitro, cyano, sulfonato, hydroxyl$(C_1-C_5)$alkyl and halo$(C_1-C_5)$alkyl.

"Aryl" or "aromatic" means an aromatic monocyclic or polycyclic (e.g., bicyclic or tricyclic) carbocyclic ring system. Thus, "$(C_5-C_{14})$aryl" is a (5-14)-membered monocyclic or bicyclic system. Aryl systems include, but are not limited to, phenyl, naphthalenyl, fluorenyl, indenyl, azulenyl, and anthracenyl.

"Cycloalkyl" means a saturated aliphatic cyclic hydrocarbon ring. Thus, "$(C_3-C_{10})$cycloalkyl" means a hydrocarbon radical of a (3-10)-membered saturated aliphatic cyclic hydrocarbon ring. "$(C_3-C_{10})$cycloalkyl" includes, but is not limited to, cyclopropyl, cyclobutyl, cyclopentyl, cyclohexyl and cycloheptyl.

"Hetero" refers to the replacement of at least one carbon atom in a ring system with at least one heteroatom selected from N, S and a "Hetero" also refers to the replacement of at least one carbon atom in an acyclic system. A hetero ring system or a hetero acyclic system may have, for example, 1, 2 or 3 carbon atoms replaced by a heteroatom.

"Heterocyclyl" means a cyclic saturated or unsaturated aliphatic or aromatic ring containing 1, 2, 3, 4 or 5 heteroatoms independently selected from N, O or S. Thus, $(C_3-C_{10})$ heterocyclyl refers to a (3-10)-membered ring system, wherein at least one carbon atom has been replaced with at least one heteroatom selected from N, S and O. When one heteroatom is S, it can be optionally mono- or di-oxygenated (i.e., —S(O)— or —S(O)$_2$—). In some embodiments of the invention, the heterocyclyl is a saturated heterocyclyl (i.e., an aliphatic heterocyclyl group without any degree of unsaturation, such as a double bond or a triple bond). Examples of monocyclic saturated heterocyclyls include, but are not limited to, azetidine, pyrrolidine, piperidine, piperazine, azepane, hexahydropyrimidine, tetrahydrofuran, tetrahydropyran, morpholine, thiomorpholine, dioxolane and dioxane.

"Heteroaryl" means a monovalent heteroaromatic monocyclic or polycyclic (e.g., bicyclic or tricyclic) ring radical. A heteroaryl contains 1, 2, 3 or 4 heteroatoms independently selected from N, O and S. Thus, "$(C_5-C_{14})$heteroaryl" refers to a (5-14)-membered ring system, wherein at least one carbon atom has been replaced with at least one heteroatom selected from N, S and O. Heteroaryls include, but are not limited to furan, oxazole, thiophene, 1,2,3-triazole, 1,2,4-triazine, 1,2,4-triazole, 1,2,5-thiadiazole 1,1-dioxide, 1,2,5-thiadiazole 1-oxide, 1,2,5-thiadiazole, 1,3,4-oxadiazole, 1,3,4-thiadiazole, 1,3,5-triazine, imidazole, isothiazole, isoxazole, pyrazole, pyridazine, pyridine, pyridine-N-oxide, pyrazine, pyrimidine, pyrrole, tetrazole, and thiazole.

"Bicycloheteroaryl," as used herein, refers to bicyclic heteroaryl rings, such ase bicyclo[4.4.0] and bicyclo[4.3.0] fused ring systems containing at least one aromatic ring and 1 to 4 heteroatoms independently selected from N, O and S. In some embodiments of the invention, the first ring is a monocyclic heterocyclyl (such as dioxolane) and the second ring is a monocyclic aryl (such as phenyl) or a monocyclic heteroaryl (such as pyridine). Examples of bicyclic heteroaryl rings include, but are not limited to, indole, quinoline, quinazoline, benzothiophene, benzofuran, 2,3-dihydrobenzofuran, benzodioxole, benzimidazole, indazole, benzisoxazole, benzoxazole and benzothiazole.

Each cycloalkyl, heterocyclyl, aryl and heteroaryl is optionally and independently substituted. Exemplary substituents include halogen, $(C_1-C_3)$alkoxy, $(C_1-C_3)$alkylthio, hydroxy, $(C_5-C_{14})$aryl, $(C_5-C_{14})$heteroaryl, $(C_3-C_{15})$cycloalkyl, $(C_3-C_{15})$heterocyclyl, amino, $(C_1-C_5)$alkylamino, $(C_1-C_5)$dialkylamino, thio, oxo, $(C_1-C_5)$alkyl, $(C_5-C_{14})$aryl $(C_1-C_5)$alkyl, $(C_5-C_{14})$heteroaryl$(C_1-C_5)$alkyl, nitro, cyano, sulfonato, hydroxyl$(C_1-C_5)$alkyl and halo$(C_1-C_5)$alkyl.

As used herein, "halogen" refers to fluorine, chlorine, bromine or iodine. "Halogen" and "halo" are used interchangeably herein.

As used herein, "halo$(C_1-C_5)$alkyl" means a $(C_1-C_5)$alkyl substituted with one or more halo groups. Haloalkyl includes mono, poly, and perhaloalkyl groups, wherein each halogen is independently selected from fluorine, chlorine, bromine and iodine.

"Alkoxy" means an alkyl radical attached through an oxygen linking atom. "$(C_1-C_3)$alkoxy" includes methoxy, ethoxy and propoxy.

"Alkylthio" means an alkyl radical attached through a sulfur linking atom.

"Alkylamino" means an alkyl radical attached through an —NH— linkage.

"Dialkylamino" means two alkyl radical attached through a nitrogen linking atom. In some embodiments, the two alkyl radicals are the same (e.g., N,N-dimethylamino). In some embodiments, the two alkyl radicals are different (e.g., N-ethyl-N-methylamino).

"Anion," as used herein, refers to a negatively charged ion. Examples of anions include, but are not limited to, halide, trifluoroacetate, acetate, benzenesulfonate, benzoate, perchlorate, sulfonate, bicarbonate, carbonate, citrate, mesylate, methylsulfate, nitrate, phosphate/diphosphate, and sulfate.

"Linking group," as used herein, refers to a functional group or chemical moiety attached to a compound of structural formula (I) capable of reacting with a complementary functional group of a biomolecule, thereby forming a covalent bond between the compound of structural formula (I) and the biomolecule. For examples of commonly used linking groups, see Hermanson, Greg T. *Bioconjugate Techniques*, Second Edition, Academic Press, Inc. (2008).

"L," used herein, denotes said functional group or chemical moiety prior to formation of the covalent bond. "L'," used herein, denotes said functional group or chemical moiety after formation of the covalent bond. For example, if "L" is an N-hydroxysuccinimide ester, and the complementary functional group of the biomolecule is —NH$_2$, then "L'" is —NR$^{13}$C(O)—, wherein R$^{13}$ is hydrogen. When a chemical formula denoting L' is used, it should be read to include all possible modes of linkage. Thus, "—NR$^{13}$C(O)—" denotes both —NR$^{13}$C(O)— and —C(O)NR$^{13}$—. If, in the previous example, the functional groups are reversed, such that "L" is —NH$_2$ and the complementary functional group of the biomolecule is an N-hydroxysuccinimide ester, then "L'" is again —NR$^{13}$C(O)—, wherein R$^{13}$ is hydrogen.

"Biomolecule," as used herein, refers to a natural or synthetic molecule for use in biological systems. Examples of biomolecules include, but are not limited to, proteins, peptides, enzyme substrates, pharmaceuticals, ligands, hormones, antibodies, antigens, haptens, carbohydrates, oligosaccharides, polysaccharides, nucleic acids, fragments of DNA and fragments of RNA.

"Ligand," as used herein, refers to a molecule that specifically binds to a biomolecule, such as a target, or to a metal. Examples of ligands include, but are not limited to, biotin and lipoic acid.

"Target," as used herein, refers to a biomolecule that specifically binds to another biomolecule. Examples of targets include, but are not limited to, a protein, a peptide, an enzyme, an oligosaccharide, a polysaccharide, a fragment of DNA and a fragment of RNA. In some embodiments of the invention, target proteins (e.g., avidin/streptavidin) bind ligands (e.g., biotin). In some embodiments of the invention, target proteins [e.g., human epidermal growth factor receptor 2 (HER2), epidermal growth factor receptor (EGFR)] bind antibodies (e.g., anti-HER2, anti-EGFR).

Another embodiment of the present invention is a biosensor. The biosensors of the present invention comprise a nanoparticle functionalized with a compound of structural formula (I). As used herein, "nanoparticle" refers to a particle with a diameter of approximately 1 nm to approximately 100 nm. In some embodiments of the invention, the nanoparticle is a metal nanoparticle, for example, a gold or silver nanoparticle.

As used herein, "functionalized" refers both to (1) the covalent attachment of a compound of structural formula (I) to a nanoparticle, as might be achieved, for example, by chemical reaction, and to (2) the noncovalent attachment of a compound of structural formula (I) to a nanoparticle, as might be achieved, for example, by surface adsorption or through a dative metal-ligand bond. Non-covalent functionalization of a nanoparticle with a compound of structural formula (I) can be achieved, for example, by mixing an aqueous solution of a lipoic acid-containing compound of structural formula (I) with a colloid of gold in aqueous sodium citrate.

In some embodiments, the biosensors of the present invention further include a second biomolecule that at least partially encapsulates the nanoparticle functionalized with the compound of structural formula (I). Examples of the second biomolecule include, but are not limited to, proteins (e.g., albumins) and water-soluble polymers (e.g., polyethylene glycol, and derivatives thereof). Encapsulation can be achieved, for example, by incubating a colloid of nanoparticles [e.g., gold nanoparticles functionalized with a lipoic acid-containing compound of structural formula (I)] with a second biomolecule [e.g., bovine serum albumin (BSA)]. Encapsulation can optionally be carried out in the presence of a cross-linking reagent, such as glutaraldehyde. Encapsulation with a second biomolecule can increase the stability of the colloid by preventing aggregation of the nanoparticles and/or desorption of the compound of structural formula (I).

In some embodiments, the biosensors of the present invention further include a third biomolecule in contact with the second biomolecule. Examples of the third biomolecule include, but are not limited to, a protein, a peptide, an enzyme substrate, a pharmaceutical, a ligand, a hormone, an antibody, an antigen, a hapten, a carbohydrate, an oligosaccharide, a polysaccharide, a nucleic acid, a fragment of DNA or a fragment of RNA. Functionalization of the biosensor with a third biomolecule can be achieved, for example, by cross-linking. For example, a BSA-encapsulated biosensor can be treated with an activating reagent, such as N-(3-(dimethylamino)-propyl)-N'-ethylcarbodiimide (EDC), and N-hydroxysuccinimide to produce activated particles. The activated particles can then be incubated with an antibody, such as anti-HER2 or scFv anti-HER2, to produce biosensors functionalized with a third biomolecule.

In one embodiment of a biosensor of the present invention, gold nanoparticles are functionalized with a reporter, such as a compound of structural formula (I), encapsulated with BSA and further functionalized with an antibody, such as anti-HER2 or scFv anti-HER 2. The resulting biosensor is a SERS-active nanoparticle equipped to specifically detect HER2 in cells and animals.

A fourth embodiment of the present invention is a method of labeling a biomolecule. The method comprises treating a sample including a biomolecule to be labeled with a compound of structural formula (I), wherein R is $(C_1-C_{15})$ branched or straight-chain alkyl, $(C_3-C_{10})$cycloalkyl, $(C_3-C_{10})$heterocyclyl, $(C_5-C_{14})$aryl, $(C_5-C_{14})$heteroaryl, $(C_5-C_{14})$aryl$(C_1-C_{15})$alkyl, $(C_5-C_{14})$heteroaryl$(C_1-C_{15})$alkyl, $(C_1-C_{10})$alkoxy$(C_1-C_{15})$alkyl, $(C_3-C_{10})$heterocyclyl$(C_1-C_{15})$alkyl, $(C_3-C_{10})$cyclo alkyl$(C_1-C_{15})$alkyl, $(C_5-C_{14})$bicycloheteroaryl$(C_1-C_{15})$alkyl, amino$(C_1-C_{15})$alkyl, $(C_1-C_{10})$alkylamino$(C_1-C_{15})$alkyl, $(C_1-C_{10})$dialkylamino$(C_1-C_{15})$alkyl or $(C_1-C_{10})$alkylthio$(C_1-C_{15})$alkyl and is optionally and independently substituted with one or more substituents selected from the group consisting of halogen, $(C_1-C_3)$alkoxy, $(C_1-C_3)$alkylthio, hydroxy, $(C_5-C_{14})$aryl, $(C_5-C_{14})$heteroaryl, $(C_3-C_{10})$cycloalkyl, $(C_3-C_{10})$heterocyclyl, amino, $(C_1-C_5)$alkylamino, $(C_1-C_5)$dialkylamino, thio, oxo, $(C_1-C_5)$alkyl, $(C_5-C_{14})$aryl$(C_1-C_5)$alkyl, nitro, cyano, sulfonato and halo$(C_1-C_5)$alkyl;

$R^1$ is $-C(O)R^{12}$, $-C(O)OR^{12}$, $-C(O)N(R^{12})_2$, $-C(S)R^{12}$, $-C(S)OR^{12}$, $-C(O)SR^{12}$, $-C(S)SR^{12}$ or $-C(S)N(R^{12})_2$, wherein each $R^{12}$ is independently hydrogen, $(C_1-C_{15})$ branched or straight-chain alkyl, $(C_3-C_{10})$cycloalkyl, $(C_3-C_{10})$heterocyclyl, $(C_5-C_{14})$aryl, $(C_5-C_{14})$heteroaryl, $(C_5-C_{14})$aryl$(C_1-C_{15})$alkyl, $(C_5-C_{14})$heteroaryl$(C_1-C_{15})$alkyl, $(C_1-C_{10})$alkoxy$(C_1-C_{15})$alkyl, $(C_3-C_{10})$heterocyclyl$(C_1-C_{15})$alkyl, $(C_3-C_{10})$cycloalkyl$(C_1-C_{15})$alkyl, amino$(C_1-C_{15})$alkyl, $(C_1-C_{10})$alkylthio$(C_1-C_{15})$alkyl, $-(CH_2)_qL$, $-(CH_2CH_2O)_qL$, $-(CH_2CH_2S)_qL$ or $-(CH_2CH_2NR^{13})_qL$, and is optionally and independently substituted with one or more substituents selected from the group consisting of halogen, $(C_1-C_3)$alkoxy, hydroxy, $(C_5-C_{14})$aryl, $(C_5-C_{14})$heteroaryl, $(C_3-C_{10})$cycloalkyl, $(C_3-C_{10})$heterocyclyl, amino, $(C_1-C_5)$alkylamino, $(C_1-C_5)$dialkylamino, thio, oxo, $(C_1-C_5)$alkyl, $(C_5-C_{14})$aryl$(C_1-C_5)$alkyl, $(C_5-C_{14})$heteroaryl$(C_1-C_5)$alkyl, nitro, cyano, sulfonato, hydroxyl$(C_1-C_5)$alkyl and halo$(C_1-C_5)$alkyl, wherein q is an integer from 1 to 50, L is a linking group and each $R^{13}$ is independently hydrogen or $(C_1-C_5)$alkyl;

or two $R^{12}$ groups, taken together with the N to which they are bound, form a $(C_3-C_{10})$heterocyclyl or $(C_5-C_{14})$heteroaryl;

or one $R^{12}$ group and R, taken together with the atoms to which they are bound, form a (4-10)-membered ring and the second $R^{12}$ group, if present, is as defined above;

$R^2$ and $R^3$ are each independently hydrogen or $(C_1-C_{15})$ alkyl, or $R^2$ and $R^3$ optionally form a (3-6)-membered ring together with the carbon atom to which they are bound;

$R^5$ and $R^6$ are each independently branched or straight-chain $(C_1-C_{15})$alkyl, $(C_3-C_{10})$cycloalkyl, $(C_3-C_{10})$heterocyclyl, $(C_5-C_{14})$aryl, $(C_5-C_{14})$heteroaryl, $(C_5-C_{14})$aryl$(C_1-C_{15})$alkyl, $(C_5-C_{14})$heteroaryl$(C_1-C_{15})$alkyl, $(C_1-C_{10})$alkoxy$(C_1-C_{15})$alkyl, $(C_3-C_{15})$heterocyclyl$(C_1-C_{15})$alkyl, $(C_3-C_{15})$cycloalkyl$(C_1-C_{15})$alkyl, amino$(C_1-C_{15})$alkyl, $(C_1-C_{10})$alkylthio$(C_1-C_{15})$alkyl, $-(CH_2)_qL$, $-(CH_2CH_2O)_qL$, $-(CH_2CH_2S)_qL$ or $-(CH_2CH_2NR^{13})_qL$, wherein each $R^5$ and $R^6$ is optionally and independently substituted with one or more substituents selected from the group consisting of halogen, $(C_1-C_3)$alkoxy, $(C_1-C_3)$alkylthio, hydroxy, $(C_5-C_{14})$aryl, $(C_5-C_{14})$hetero aryl, $(C_3-C_{15})$cycloalkyl, $(C_3-C_{15})$heterocyclyl, amino, $(C_1-C_5)$alkylamino, $(C_1-C_5)$dialkylamino, thio, oxo, $(C_1-C_5)$alkyl, $(C_5-C_{14})$aryl$(C_1-C_5)$alkyl, $(C_5-C_{14})$heteroaryl$(C_1-C_5)$alkyl, nitro, cyano, sulfonato, hydroxyl$(C_1-C_5)$alkyl and halo$(C_1-C_5)$alkyl;

$R^8$ and $R^9$ are each independently hydrogen or $(C_1-C_{15})$ alkyl, or $R^8$ and $R^9$ optionally form a (3-6)-membered ring together with the carbon atom to which they are bound;

each $R^4$ and $R^7$ is independently halo, $(C_1-C_5)$alkyl, $(C_5-C_{14})$aryl, $(C_5-C_{14})$heteroaryl, $(C_3-C_{10})$cycloalkyl, $(C_3-C_{10})$heterocyclyl, hydroxy, carboxylate, nitro, cyano, amino, $(C_1-C_5)$alkylamino, $(C_1-C_5)$dialkylamino, $(C_1-C_3)$alkoxy, $(C_1-C_3)$alkylthio, thio, sulfonato or halo$(C_1-C_5)$alkyl, or two $R^4$ or two $R^7$ together with the carbon atoms to which they are bound, each independently form a $(C_4-C_{10})$cycloalkyl, $(C_4-C_{10})$heterocyclyl, $(C_5-C_{14})$aryl or $(C_5-C_{14})$heteroaryl;

$R^{10}$ and $R^{11}$ are each independently hydrogen, $(C_1-C_{15})$ alkyl, or optionally, together with the carbon atoms to which they are bound, form a 5- or 6-membered ring;

m and n are each independently an integer from 0 to 4;

p is an integer from 0 to 3; and

X is an anion, wherein at least one of $R^5$, $R^6$ and $R^{12}$ is $-(CH_2)_qL$, $-(CH_2CH_2O)_qL$, $-(CH_2CH_2S)_qL$ or $-(CH_2CH_2NR^{13})_qL$;

wherein L reacts with the biomolecule to form L'-B, wherein L' is a linking group and B is the biomolecule to be labeled, thereby labeling the biomolecule.

In a first aspect of the fourth embodiment, the biomolecule is a protein, a peptide, an enzyme substrate, a pharmaceutical, a ligand, a hormone, an antibody, an antigen, a hapten, a carbohydrate, an oligosaccharide, a polysaccharide, a nucleic acid, a fragment of DNA or a fragment of RNA, wherein the values and alternative values for the remaining variables are as defined in the first, second or third embodiments, or aspects thereof, in the fourth embodiment or in the values and alternative values described above.

In a second aspect of the fourth embodiment, L is amino, hydroxyl, thio, haloalkyl, N-hydroxy succinimidyl ester, sulfonato-N-hydroxy succinimidyl ester, thiocyanato, isothiocyanato, nitrophenolyl, iodoacetamidyl, maleimidyl, carboxyl, thioacetyl, sulfonato or phosphoramidityl; and L' is —$NR^{13}$—, —O—, —S—, —$S(O)_2O$—, —$OP(OR^{13})N(R^{13})$—, —$OP(N(R^{13})_2)O$—, —$NR^{13}C(O)$—, —$OC(O)$—, —$SC(O)$—, —$OC(S)$—, —$SC(S)$—, —$OC(NR^{13})S$—, —$SC(NR^{13})S$—, —$NR^{13}C(NR^{13})S$—, —$NR^{13}C(O)S$—, —$NR^{13}C(S)O$—, —$NR^{13}C(S)N(R^{13})$—, —$NR^{13}C(O)N(R^{13})$—, —$OC(O)O$—, —$SC(O)S$—, —$OC(S)O$—, —$OC(S)S$—, —$SC(O)O$—, —$NR^{13}C(O)O$— or —$NR^{13}C(NR^{13})N(R^{13})$—, wherein each $R^{13}$ is independently hydrogen or ($C_1$-$C_5$)alkyl and wherein the values and alternative values for the remaining variables are as defined in the first, second or third embodiments, or aspects thereof, in the fourth embodiment or in the values and alternative values described above.

A fifth embodiment of the present invention is a method of detecting the presence of a target in a sample. The method comprises treating a sample with a compound of structural formula (I), wherein:

R is ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, ($C_5$-$C_{14}$)bicycloheteroaryl($C_1$-$C_{15}$)alkyl, amino($C_1$-$C_{15}$)alkyl, ($C_1$-$C_{10}$)alkylamino($C_1$-$C_{15}$)alkyl, ($C_1$-$C_{10}$)dialkylamino($C_1$-$C_{15}$)alkyl or ($C_1$-$C_{10}$)alkylthio($C_1$-$C_{15}$)alkyl and is optionally and independently substituted with one or more substituents selected from the group consisting of halogen, ($C_1$-$C_3$)alkoxy, ($C_1$-$C_3$)alkylthio, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, nitro, cyano, sulfonato and halo($C_1$-$C_5$)alkyl;

$R^1$ is —$C(O)R^{12}$, —$C(O)OR^{12}$, —$C(O)N(R^{12})_2$, —$C(S)R^{12}$, —$C(S)OR^{12}$, —$C(O)SR^{12}$, —$C(S)SR^{12}$ or —$C(S)N(R^{12})_2$, wherein each $R^{12}$ is independently hydrogen, ($C_1$-$C_{15}$) branched or straight-chain alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{10}$)heterocyclyl($C_1$-$C_{15}$)alkyl, ($C_3$-$C_{10}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —$(CH_2)_qL'$-B, —$(CH_2CH_2O)_qL'$-B, —$(CH_2CH_2S)_qL'$-B or —$(CH_2CH_2NR^{13})_qL'$-B and is optionally and independently substituted with one or more substituents selected from the group consisting of halogen, ($C_1$-$C_3$)alkoxy, hydroxy, ($C_5$-$C_{14}$)aryl, ($C_5$-$C_{14}$)heteroaryl, ($C_3$-$C_{10}$)cycloalkyl, ($C_3$-$C_{10}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl($C_1$-$C_5$)alkyl and halo($C_1$-$C_5$)alkyl, wherein q is an integer from 1 to 50, L' is a linking group, each $R^{13}$ is independently hydrogen or ($C_1$-$C_5$)alkyl and B is a biomolecule; or two $R^{12}$ groups, taken together with the N to which they are bound, form a ($C_3$-$C_{10}$)heterocyclyl or ($C_5$-$C_{14}$)heteroaryl; or one $R^{12}$ group and R, taken together with the atoms to which they are bound, form a (4-10)-membered ring and the second $R^{12}$ group, if present, is as defined above;

$R^2$ and $R^3$ are each independently hydrogen or ($C_1$-$C_{15}$) alkyl, or $R^2$ and $R^3$ optionally form a (3-6)-membered ring together with the carbon atom to which they are bound;

$R^5$ and $R^6$ are each independently branched or straight-chain ($C_1$-$C_{15}$)alkyl, ($C_3$-$C_{10}$)cycloalkyl, ($C_3$-$C_{10}$)heterocyclyl, ($C_5$-$C_{14}$)aryl, ($C_5$-$C_{14}$)heteroaryl, ($C_5$-$C_{14}$)aryl($C_1$-$C_{15}$)alkyl, ($C_5$-$C_{14}$)heteroaryl($C_1$-$C_{15}$)alkyl, ($C_1$-$C_{10}$)alkoxy($C_1$-$C_{15}$)alkyl, ($C_3$-$C_{15}$)heterocyclyl($C_1$-$C_{15}$)alkyl, ($C_3$-$C_{15}$)cycloalkyl($C_1$-$C_{15}$)alkyl, amino($C_1$-$C_{15}$)alkyl, ($C_1$-$C_{10}$)alkylthio($C_1$-$C_{15}$)alkyl, —$(CH_2)_qL'$-B, —$(CH_2CH_2O)_qL'$-B, —$(CH_2CH_2S)_qL'$-B or —$(CH_2CH_2NR^{13})_qL'$-B, wherein each $R^5$ and $R^6$ is optionally and independently substituted with one or more substituents selected from the group consisting of halogen, ($C_1$-$C_3$)alkoxy, ($C_1$-$C_3$)alkylthio, hydroxy, ($C_5$-$C_{14}$)aryl, ($C_5$-$C_{14}$)heteroaryl, ($C_3$-$C_{15}$)cycloalkyl, ($C_3$-$C_{15}$)heterocyclyl, amino, ($C_1$-$C_5$)alkylamino, ($C_1$-$C_5$)dialkylamino, thio, oxo, ($C_1$-$C_5$)alkyl, ($C_5$-$C_{14}$)aryl($C_1$-$C_5$)alkyl, ($C_5$-$C_{14}$)heteroaryl($C_1$-$C_5$)alkyl, nitro, cyano, sulfonato, hydroxyl($C_1$-$C_5$)alkyl and halo($C_1$-$C_5$)alkyl;

$R^8$ and $R^9$ are each independently hydrogen or ($C_1$-$C_{15}$) alkyl, or $R^8$ and $R^9$ optionally form a (3-6)-membered ring together with the carbon atom to which they are bound;

each $R^4$ and $R^7$ is independently halo, ($C_1$-$C_5$)alkyl, ($C_5$-$C_4$)aryl, ($C_5$-$C_{14}$)heteroaryl, ($C_3$-$C_{10}$)cycloalkyl, ($C_3$-$C_{10}$)heterocyclyl, hydroxy, carboxylate, nitro, cyano, amino, ($C_1$-$C_5$)alkylamino, ($C_1$-$C_5$)dialkylamino, ($C_1$-$C_3$)alkoxy, ($C_1$-$C_3$)alkylthio, thio, sulfonato or halo($C_1$-$C_5$)alkyl, or two $R^4$ or two $R^7$ together with the carbon atoms to which they are bound, each independently form a ($C_4$-$C_{10}$)cycloalkyl, ($C_4$-$C_{10}$)heterocyclyl, ($C_5$-$C_{14}$)aryl or ($C_5$-$C_{14}$)heteroaryl;

$R^{10}$ and $R^{11}$ are each independently hydrogen, ($C_1$-$C_{15}$) alkyl, or optionally, together with the carbon atoms to which they are bound, form a 5- or 6-membered ring;

m and n are each independently an integer from 0 to 4;

p is an integer from 0 to 3; and

X is an anion, wherein at least one of $R^5$, $R^6$ and $R^{12}$ is —$(CH_2)_qL'$-B, —$(CH_2CH_2O)_gL'$-B, —$(CH_2CH_2S)_qL'$-B or —$(CH_2CH_2NR^{13})_qL'$-B; and measuring a signal produced by the compound of structural formula (I), wherein the presence of the signal indicates the presence of a target in the sample, thereby determining whether the target is present in the sample.

In a first aspect of the fifth embodiment, the sample is treated with a biosensor of the present invention, said biosensor comprising a compound of structural formula (I), wherein the values and alternative values for the remaining variables are as defined in the first, second, third or fourth embodiments, or aspects thereof, in the fifth embodiment or in the values and alternative values described above.

In a second aspect of the fifth embodiment, the signal is fluorescence or a Raman signal, wherein the values and alternative values for the remaining variables are as defined in the first, second, third or fourth embodiments, or aspects thereof, in the fifth embodiment or in the values and alternative values described above.

In some embodiments, the presence of the signal indicates binding of the compound of structural formula (I) to the target. For example, when B is a monoclonal antibody to EGFR, the presence of a signal indicates binding of the anti-EGFR-labeled compound of structural formula (I) to EGFR. In some embodiments, the presence of the signal indicates binding of a biosensor of the invention to the target. For example, a BSA-encapsulated gold nanoparticle functionalized with a compound of structural formula (I) can be further functionalized with an antibody to HER2. In this case, the presence of the signal indicates binding of the anti-HER2-functionalized nanoparticle to HER2. Thus, the presence of the signal indicates the presence of the target.

The step of measuring the signal can include collecting dark-field microscopy images using, for example, a dark-field illumination system attached to a microscope, collecting fluorescence spectra using, for example, a spectrophotometer, collecting NIR-fluorescence images using, for example a microscope attached to a Ti:sapphire oscillator, collecting SERS signals using, for example, a Raman scanner or a Renishaw Raman microscope, or collecting fluorescence images using, for example, an IVIS Spectrum imaging system (for in vivo images) or a gel imaging system (for images of gels).

A sixth embodiment is a compound represented by Structural Formula (II):

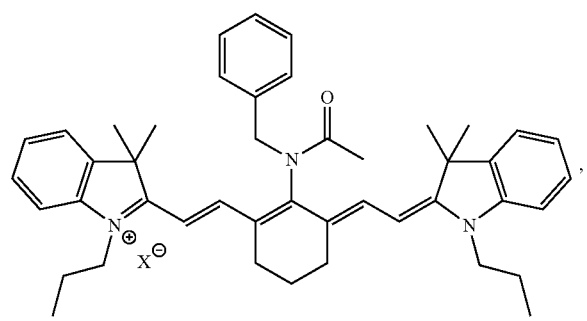

(II)

wherein X is an anion.

In a first aspect of the sixth embodiment, X is iodo (CyNA-374).

Another embodiment is a method of detecting activated macrophage cells in an animal, comprising treating the animal with a compound of Structural Formula (II); and measuring a signal produced by the compound of Structural Formula (II), wherein the presence of the signal indicates the presence of activated macrophage cells, thereby detecting activated macrophage cells in an animal. The animal can be a live animal.

Another embodiment is a method of detecting inflammation in an animal, comprising treating the animal with a compound of Structural Formula (II); and measuring a signal produced by the compound of Structural Formula (II), wherein the presence of the signal indicates inflammation, thereby detecting inflammation in an animal. The animal can be a live animal.

EXEMPLIFICATION

A description of example embodiments of the invention follows:

Example 1

Development of Photostable Near-Infrared (NIR) Cyanine Dyes

With the emerging interest in optical in vivo imaging, there is an increasing demand for photostable NIR dyes, such as CyNA-414. CyNA-414 is a fluorescent NIR dye with stronger emission intensity and higher photostability than the NIR standard, IndoCyanine Green (ICG).

While the amine tricarbocyanine (CyN) structure has been described as a promising NIR scaffold for broad chemical derivatization, its low photostability in aqueous media has hampered its biological application. In order to examine the decomposition mechanism of tricarbocyanine dyes, the photodecomposition reaction of one amine tricarbocyanine derivative, CyN-111, was analyzed using HPLC, LCMS, IR spectroscopy and NMR spectroscopy.

Upon light irradiation, CyN-111 quickly underwent the incorporation of a reactive singlet oxygen species to render CyN-111a. An LCMS spectrum taken after 2 hours showed the absence of a peak with a mass and retention time corresponding to CyN-111 and the presence of a new peak with a shorter retention time. The mass corresponding to the new peak correlated well with the calculated mass of CyN-111a. An LCMS spectrum taken after 6 hours lacked a peak corresponding to the mass and retention time of CyN-111, as expected. A peak corresponding to the mass and retention time of CyN-111a remained, but was accompanied by a third peak with a shorter retention time than both CyN-111 and CyN-111a. The mass corresponding to the third peak correlated well with the calculated mass of CyN-111b. An IR spectrum taken after 6 hours showed two strong peaks in the carbonyl region at 1708 and 1607 $cm^{-1}$ that were not present in the IR spectrum of CyN-111 taken before irradiation. These two peaks correspond to the ketone and aldehyde functional groups present in CyN-111b and CyN-111c, respectively. CyN-111c was isolated from the reaction and further characterized by $^1$H NMR. The fragmentation of CyN-111 into the non-fluorescent CyN-111b and CyN-111c is depicted in FIG. 1.

Figure 2:
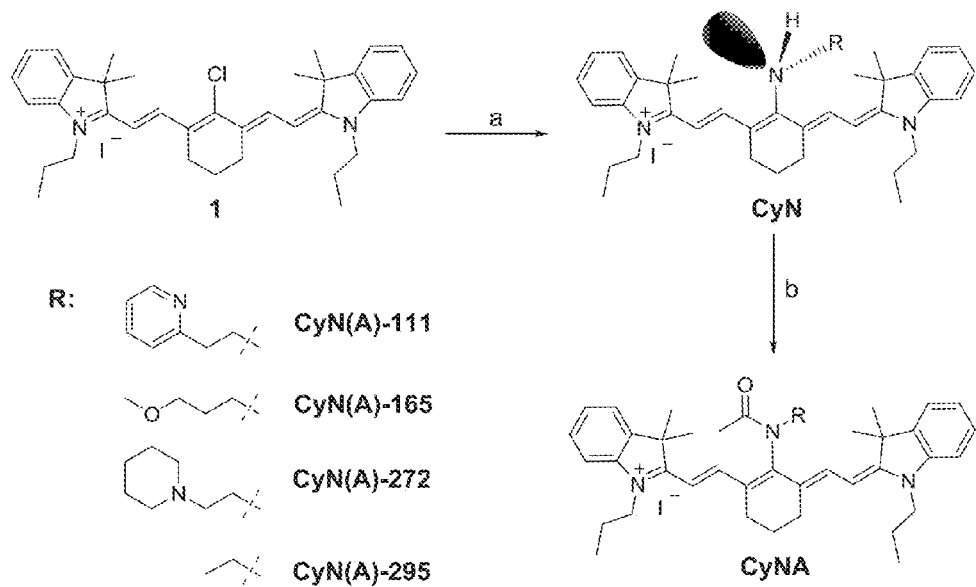
FIG. 2 shows a synthetic route to four amine tricarbocyanine (CyN) derivatives and to the corresponding acetylated amine tricarbocyanine (CyNA) derivatives.

To disfavor this decomposition mechanism, the central nitrogen atom of the CyN core was derivatized with an electron-withdrawing group. Although not wishing to be bound by any particular theory, it is believed that introduction of an electron-withdrawing group destabilizes the iminium intermediate that facilitates the incorporation of the reactive oxygen species and leads to formation of CyN-111a. To investigate this hypothesis, four structurally diverse CyN compounds were acetylated using acetyl chloride to afford the CyNA compounds depicted in FIG. 2.

Figure 3:
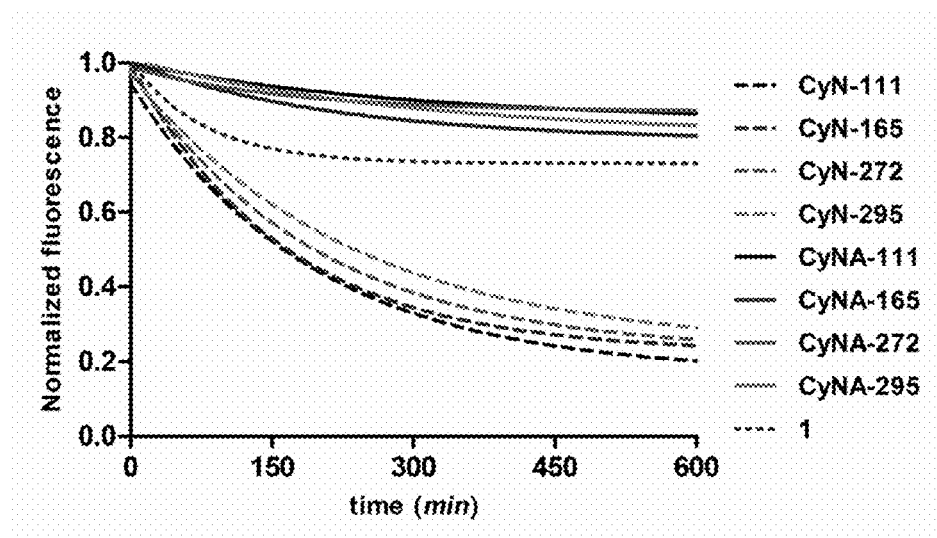
FIG. 3 is a graph of the normalized fluorescence of 10-μM solutions of 1, CyN and CyNA derivatives in HEPES buffer (10 mM, pH 7.4) containing 1% dimethylsulfoxide (DMSO) at room temperature under a xenon flash lamp over a time period of 600 min.

The photostabilities of CyN-111, CyN-165, CyN-272, CyN-295, and their CyNA counterparts were evaluated by time-course fluorescence measurements in HEPES buffer, and compared to the photostability of starting material 1. FIG. 3 is a graph of the normalized fluorescence intensities of 10-µM solutions of 1 and the CyN and CyNA compounds, and shows the improvement in the photostability of the CyN structure upon acetylation to form a CyNA compound. The photostabilities of the CyNA compounds even exceeded that of starting material 1. Calculation of the pseudo-first order rate constants (k) of the photobleaching of the CyN(A) compounds revealed that the rates of photobleaching of the CyN derivatives were 8- to 13-fold faster than the rate constants of the photobleaching of the corresponding CyNA derivatives (see Table 1). Both analyses attest to the significantly improved photostability of the CyNA scaffold compared to the CyN scaffold.

TABLE 1

Rates of Photobleaching of CyN and CyNA derivatives in aqueous media.

| compound | $k(s^{-1})$ | $k_{CyN}/k_{CyNA}$ |
|---|---|---|
| CyN-111 | $40.4 \cdot 10^{-6}$ | — |
| CyNA-111 | $3.41 \cdot 10^{-6}$ | 12 |
| CyN-165 | $34.9 \cdot 10^{-6}$ | — |
| CyNA-165 | $4.53 \cdot 10^{-6}$ | 8 |
| CyN-272 | $35.2 \cdot 10^{-6}$ | — |

TABLE 1-continued

Rates of Photobleaching of CyN and CyNA derivatives in aqueous media.

| compound | k(s$^{-1}$) | k$_{CyN}$/k$_{CyNA}$ |
|---|---|---|
| CyNA-272 | 2.67 · 10$^{-6}$ | 13 |
| CyN-295 | 31.3 · 10$^{-6}$ | — |
| CyNA-295 | 3.81 · 10$^{-6}$ | 8 |

Figure 4A:
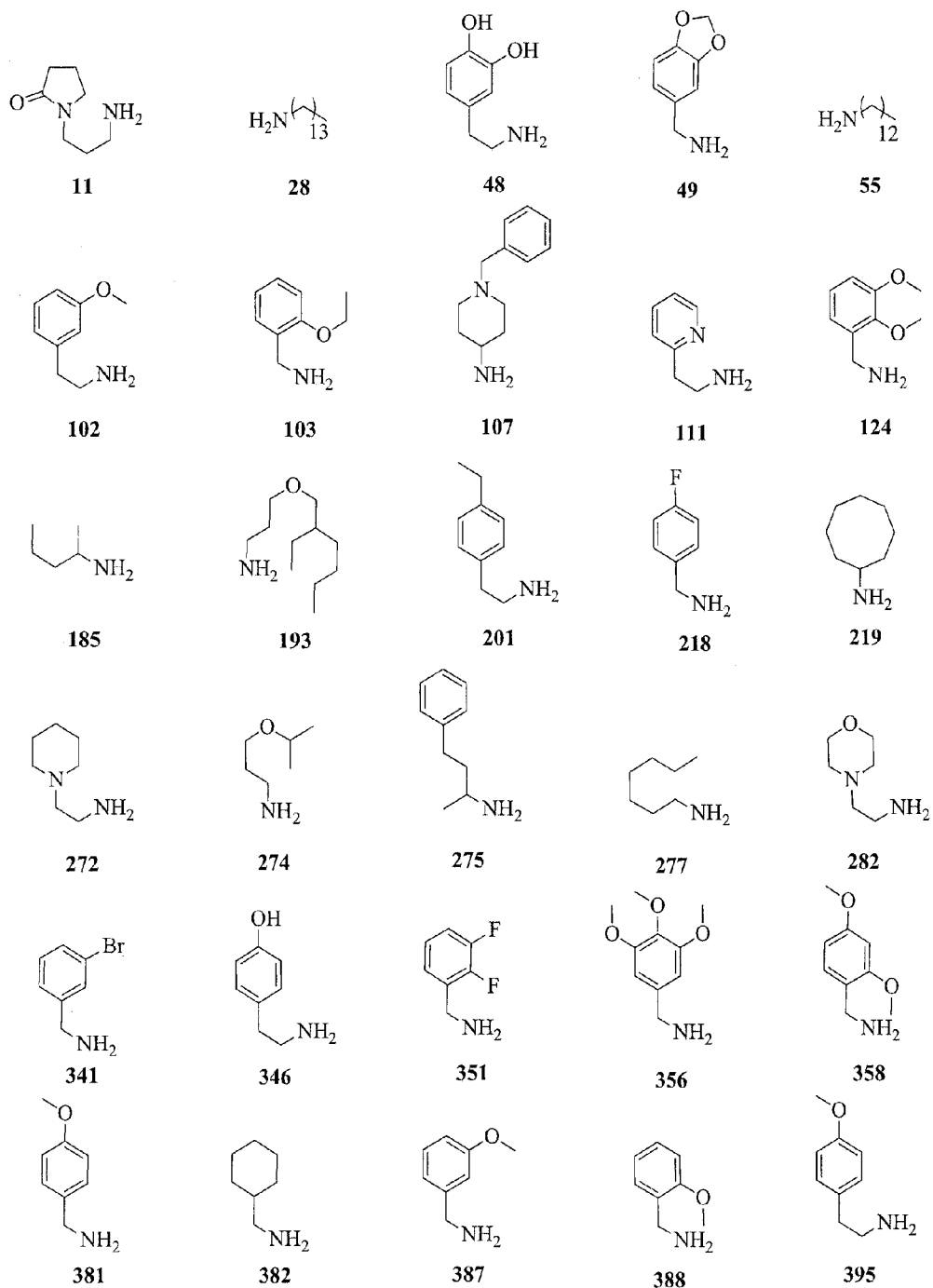
FIGS. 4A-4C show the chemical structures of the amine building blocks used to construct the CyNA library.
Figure 4B:
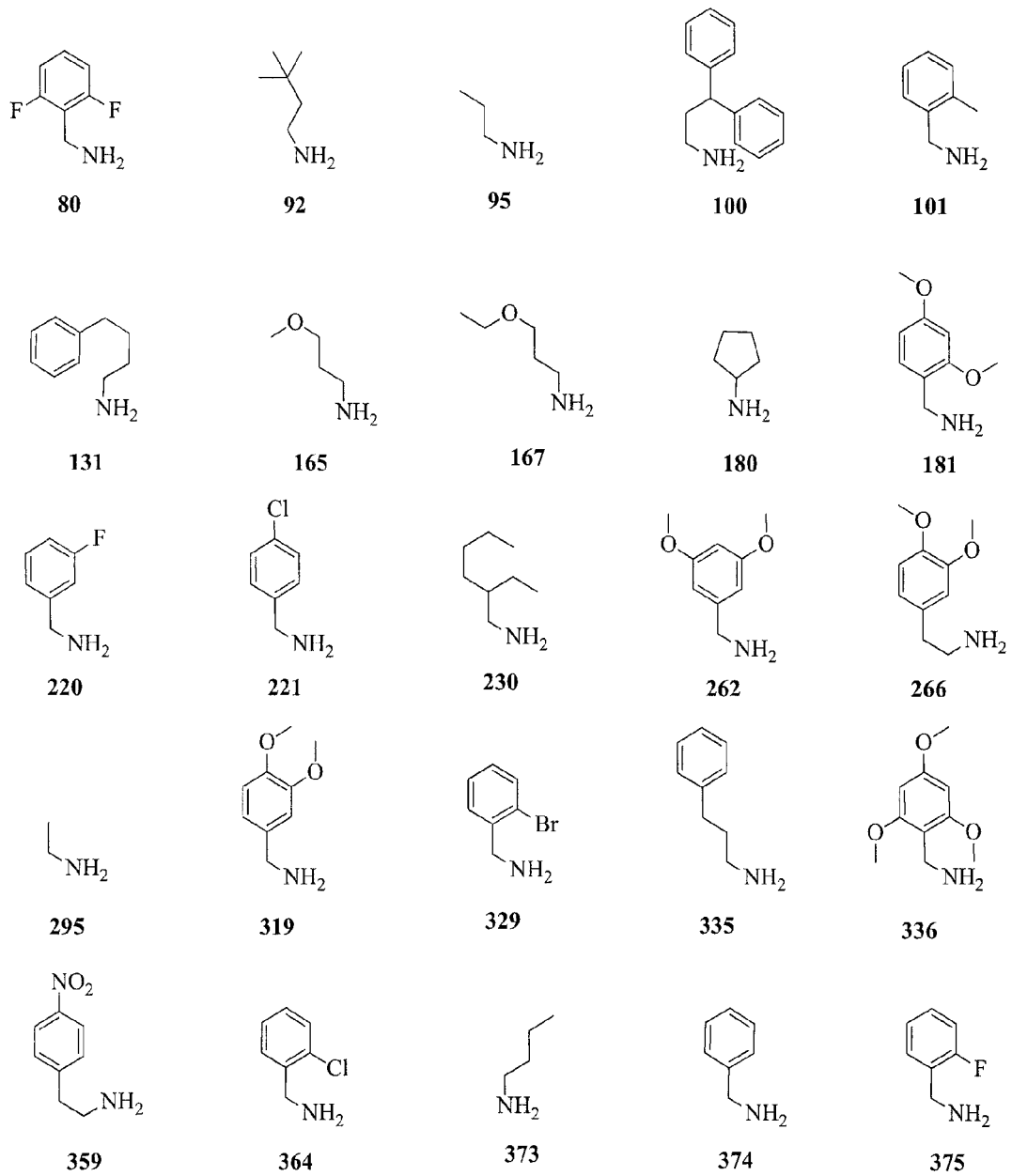
Figure 4C:
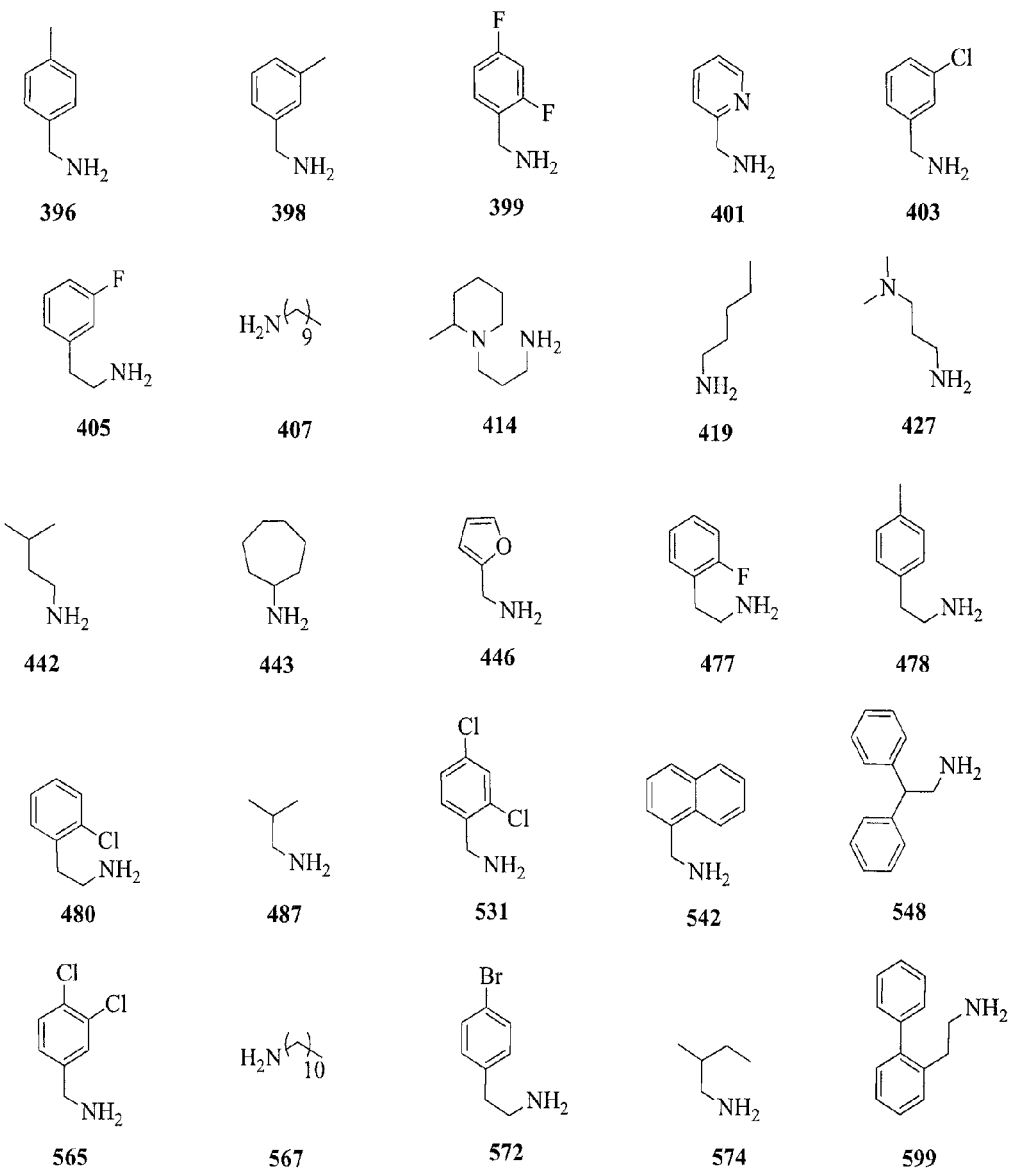

Since the k values of the different CyNA compounds indicated some dependency on the chemical structure of the amine, the CyNA scaffold was derivatized with a broad range of primary amines (FIGS. 4A-4C). The fluorescence properties of the 80-member CyNA library were measured. The absorption maximum wavelengths ranged from 802 nm to 806 nm, emission maximum wavelengths ranged from 817 nm to 823 nm, and the average quantum yield was approximately 0.10 (Table 2).

TABLE 2

Absorbance ($\lambda_{abs}$) and ($\lambda_{em}$) fluorescence maximum wavelengths, quantum yields, LCMS data, condensation reaction times, and primary evaluation of the photostability of members of the CyNA library.

| compound | tR (min) | M$^+$ (calc.) | M$^+$ (exp.) | $\lambda_{abs}$ (nm) | $\lambda_{em}$ (nm) | $\phi^1$ | purity$^2$ | reaction time (min) | max RFU | F/F$_o^3$ |
|---|---|---|---|---|---|---|---|---|---|---|
| CyNA-11 | 2.61 | 687.4 | 687.1 | 802 | 820 | 0.11 | 95.3 | 20 | 1250.1 | 90 |
| CyNA-28 | 3.42 | 758.6 | 758.2 | 804 | 818 | 0.05 | 93.2 | 20 | 23.9 | 87 |
| CyNA-48$^4$ | 2.77 | 783.4 | 783.0 | 804 | 819 | 0.06 | 94.6 | 15 | 620.9 | 45 |
| CyNA-49 | 2.82 | 696.4 | 696.1 | 804 | 818 | 0.10 | 95.3 | 30 | 851.3 | 95 |
| CyNA-55 | 3.24 | 744.5 | 744.2 | 804 | 819 | 0.13 | 97.1 | 15 | 162.3 | 100 |
| CyNA-80 | 3.00 | 688.4 | 688.2 | 804 | 817 | 0.08 | 96.1 | 50 | 734.9 | 93 |
| CyNA-92 | 2.82 | 646.4 | 646.1 | 805 | 821 | 0.09 | 96.3 | 15 | 420.2 | 64 |
| CyNA-95 | 2.8 | 604.4 | 604.2 | 806 | 818 | 0.09 | 95.6 | 10 | 1027.9 | 91 |
| CyNA-100 | 2.94 | 756.4 | 756.1 | 804 | 819 | 0.08 | 94.4 | 15 | 333.8 | 63 |
| CyNA-101 | 2.94 | 666.4 | 666.1 | 806 | 822 | 0.08 | 94.6 | 25 | 693.9 | 86 |
| CyNA-102 | 2.90 | 696.4 | 696.1 | 805 | 822 | 0.14 | 97.1 | 15 | 998.9 | 63 |
| CyNA-103 | 2.88 | 696.4 | 696.2 | 804 | 821 | 0.14 | 96.9 | 20 | 1106.6 | 92 |
| CyNA-107 | 2.35 | 735.5 | 735.1 | 803 | 820 | 0.07 | 93.4 | 30 | 275.3 | 50 |
| CyNA-111 | 2.68 | 667.4 | 667.1 | 804 | 818 | 0.11 | 98.2 | 25 | 565.6 | 96 |
| CyNA-124 | 2.86 | 712.4 | 712.1 | 803 | 820 | 0.15 | 98.1 | 30 | 1334.2 | 100 |
| CyNA-131 | 2.93 | 694.4 | 694.1 | 804 | 819 | 0.13 | 97.3 | 15 | 259.8 | n.d |
| CyNA-165 | 2.78 | 634.4 | 634.1 | 806 | 821 | 0.09 | 98.1 | 15 | 775.1 | 94 |
| CyNA-167 | 2.82 | 648.4 | 648.1 | 804 | 818 | 0.10 | 94.8 | 25 | 1031.8 | 92 |
| CyNA-180 | 2.89 | 630.4 | 630.1 | 805 | 821 | 0.14 | 97.5 | 10 | 991.3 | 91 |
| CyNA-181 | 2.8 | 712.4 | 712.1 | 805 | 821 | 0.14 | 96.5 | 30 | 996.8 | 66 |
| CyNA-185 | 2.95 | 632.4 | 632.1 | 804 | 820 | 0.15 | 97.4 | 30 | 1209.7 | 91 |
| CyNA-193 | 3.16 | 732.5 | 732.2 | 806 | 822 | 0.12 | 96.2 | 15 | 58.7 | n.d |
| CyNA-201 | 3.00 | 694.4 | 694.1 | 803 | 820 | 0.08 | 93.2 | 15 | 52.6 | 33 |
| CyNA-218 | 2.89 | 670.4 | 670.1 | 802 | 823 | 0.08 | 94.2 | 20 | 549.9 | 85 |
| CyNA-219 | 3.01 | 672.4 | 672.1 | 804 | 822 | 0.14 | 96.4 | 45 | 902.7 | 65 |
| CyNA-220 | 2.89 | 686.3 | 686.1 | 804 | 823 | 0.12 | 95.3 | 50 | 848.2 | 100 |
| CyNA-221 | 2.94 | 687.4 | 687.1 | 803 | 820 | 0.07 | 93.2 | 45 | 382.6 | 86 |
| CyNA-230 | 3.10 | 674.5 | 674.2 | 805 | 822 | 0.09 | 94.3 | 25 | 77.7 | 80 |
| CyNA-262 | 2.88 | 712.4 | 712.1 | 803 | 822 | 0.10 | 95.1 | 20 | 816.5 | 81 |
| CyNA-266 | 2.81 | 726.4 | 726.1 | 804 | 823 | 0.08 | 93.5 | 20 | 541.8 | 99 |
| CyNA-272 | 2.31 | 673.4 | 673.1 | 804 | 820 | 0.10 | 93.8 | 25 | 662.1 | 98 |
| CyNA-274 | 2.89 | 662.4 | 662.1 | 805 | 820 | 0.12 | 95.6 | 10 | 1209.5 | 99 |
| CyNA-275 | 2.97 | 694.4 | 694. | 804 | 817 | 0.14 | 96.8 | 45 | 679.8 | 62 |
| CyNA-277 | 3.09 | 660.4 | 660. | 804 | 817 | 0.11 | 93.7 | 15 | 120.8 | n.d |
| CyNA-282 | 2.31 | 675.4 | 675. | 805 | 819 | 0.09 | 93.5 | 20 | 820.1 | 90 |
| CyNA-295 | 2.85 | 590.4 | 590. | 806 | 820 | 0.11 | 96.4 | 15 | 698.6 | 100 |
| CyNA-319 | 2.80 | 712.4 | 712. | 805 | 820 | 0.06 | 92.1 | 25 | 578.6 | 67 |
| CyNA-329 | 2.97 | 732.3 | 731.9 | 806 | 821 | 0.10 | 94.5 | 60 | 348.8 | 99 |
| CyNA-335 | 2.93 | 680.4 | 680.1 | 804 | 821 | 0.06 | 93.2 | 15 | 167.9 | 50 |
| CyNA-336 | 2.82 | 742.4 | 742.1 | 804 | 820 | 0.11 | 94.5 | 25 | 827.7 | 85 |
| CyNA-341 | 3.51 | 732.4 | 732.1 | 805 | 822 | 0.10 | 93.7 | 45 | 259.2 | 100 |
| CyNA-346$^5$ | 4.58 | 724.4 | 724.1 | 804 | 822 | 0.07 | 92.7 | 25 | 434.2 | 69 |
| CyNA-351 | 4.86 | 688.4 | 688.1 | 805 | 818 | 0.10 | 95.8 | 35 | 555.4 | 52 |
| CyNA-356 | 4.44 | 742.4 | 742.1 | 804 | 820 | 0.12 | 96.9 | 20 | 892.3 | 83 |
| CyNA-358 | 4.79 | 712.4 | 712.0 | 805 | 819 | 0.14 | 98.2 | 30 | 487.4 | 100 |
| CyNA-359 | 4.76 | 711.4 | 711.1 | 805 | 821 | 0.11 | 95.6 | 20 | 527.6 | 85 |
| CyNA-364 | 5.01 | 686.3 | 686.0 | 804 | 821 | 0.05 | 92.1 | 60 | 264.8 | 98 |
| CyNA-373 | 4.90 | 618.4 | 618.1 | 805 | 820 | 0.07 | 93.6 | 15 | 567.2 | 76 |
| CyNA-374 | 4.81 | 652.4 | 652.1 | 806 | 821 | 0.14 | 97.3 | 15 | 1224.6 | 94 |
| CyNA-375 | 4.84 | 670.4 | 670.1 | 804 | 821 | 0.07 | 93.3 | 20 | 533.7 | 98 |
| CyNA-381 | 5.12 | 668.3 | 668.0 | 805 | 821 | 0.14 | 96.5 | 15 | 1259.2 | 93 |
| CyNA-382 | 5.29 | 658.4 | 658.1 | 804 | 820 | 0.08 | 93.4 | 20 | 294.6 | 85 |
| CyNA-387 | 4.71 | 682.4 | 682.1 | 804 | 820 | 0.07 | 92.9 | 30 | 739.9 | 75 |
| CyNA-388 | 4.89 | 682.4 | 682.0 | 803 | 819 | 0.14 | 97.8 | 25 | 1398.5 | 97 |
| CyNA-395 | 4.83 | 696.4 | 696.1 | 804 | 820 | 0.07 | 95.1 | 20 | 234.3 | 95 |
| CyNA-396 | 5.06 | 666.4 | 666.1 | 804 | 820 | 0.09 | 94.7 | 30 | 736.1 | 96 |
| CyNA-398 | 5.01 | 666.4 | 666.1 | 804 | 819 | 0.07 | 93.4 | 25 | 540.2 | 99 |
| CyNA-399 | 4.97 | 688.4 | 688.1 | 804 | 819 | 0.10 | 95.8 | 60 | 775.5 | 95 |

TABLE 2-continued

Absorbance ($\lambda_{abs}$) and ($\lambda_{em}$) fluorescence maximum wavelengths, quantum yields, LCMS data, condensation reaction times, and primary evaluation of the photostability of members of the CyNA library.

| compound | tR (min) | M+ (calc.) | M+ (exp.) | $\lambda_{abs}$ (nm) | $\lambda_{em}$ (nm) | $\phi^1$ | purity[2] | reaction time (min) | max RFU | F/F$_o$[3] |
|---|---|---|---|---|---|---|---|---|---|---|
| CyNA-401 | 5.03 | 653.4 | 653.1 | 805 | 820 | 0.10 | 94.9 | 35 | 856.5 | 91 |
| CyNA-403 | 4.63 | 686.3 | 686.0 | 805 | 819 | 0.05 | 93.5 | 30 | 261.6 | 45 |
| CyNA-405 | 4.99 | 684.3 | 684.0 | 806 | 820 | 0.06 | 94.5 | 20 | 138.5 | 83 |
| CyNA-407 | 5.64 | 702.3 | 702.1 | 805 | 820 | 0.08 | 96.1 | 20 | 22.5 | n.d. |
| CyNA-414 | 3.38 | 701.5 | 701.2 | 804 | 819 | 0.13 | 95.9 | 30 | 925.5 | 100 |
| CyNA-419 | 5.53 | 632.4 | 632.0 | 804 | 820 | 0.13 | 97.4 | 10 | 835.2 | 91 |
| CyNA-427 | 3.51 | 647.3 | 647.0 | 805 | 821 | 0.14 | 96.7 | 45 | 1247.4 | 100 |
| CyNA-442 | 4.97 | 632.4 | 632.1 | 806 | 822 | 0.07 | 94.3 | 25 | 424.2 | 54 |
| CyNA-443 | 5.11 | 630.4 | 630.0 | 806 | 821 | 0.09 | 95.6 | 30 | 583.5 | 75 |
| CyNA-446 | 4.79 | 642.4 | 642.1 | 804 | 821 | 0.08 | 94.2 | 25 | 709.2 | 85 |
| CyNA-477 | 4.91 | 684.9 | 684.1 | 805 | 819 | 0.09 | 93.7 | 20 | 169.8 | n.d. |
| CyNA-478 | 5.03 | 680.4 | 680.1 | 805 | 821 | 0.09 | 95.4 | 20 | 121.6 | 64 |
| CyNA-480 | 5.01 | 700.4 | 700.1 | 803 | 817 | 0.06 | 92.1 | 20 | 154.8 | 51 |
| CyNA-487 | 4.98 | 618.4 | 618.1 | 806 | 823 | 0.04 | 91.6 | 25 | 45.3 | 30 |
| CyNA-531 | 5.21 | 720.3 | 720.1 | 804 | 820 | 0.08 | 97.3 | 50 | 187.5 | 100 |
| CyNA-542 | 5.01 | 702.4 | 702.1 | 805 | 821 | 0.08 | 94.5 | 45 | 442.7 | 74 |
| CyNA-548 | 5.01 | 742.4 | 742.1 | 804 | 820 | 0.04 | 92.9 | 35 | 67.6 | n.d. |
| CyNA-565 | 5.20 | 720.3 | 720.1 | 805 | 821 | 0.09 | 95.3 | 40 | 335.5 | 96 |
| CyNA-567 | 5.69 | 716.5 | 716.2 | 805 | 820 | 0.14 | 98.3 | 20 | 279.2 | 100 |
| CyNA-572 | 5.21 | 684.4 | 684.1 | 805 | 818 | 0.05 | 93.2 | 25 | 58.9 | n.d. |
| CyNA-574 | 5.01 | 632.4 | 632.1 | 803 | 818 | 0.06 | 93.8 | 35 | 321.1 | 38 |
| CyNA-599 | 5.20 | 742.5 | 742.1 | 805 | 819 | 0.07 | 97.6 | 25 | 105.9 | n.d. |

[1]Quantum yields were measured in DMSO, using Cardiogreen as a standard ($\phi$: 0.13, in DMSO).
[2]Purities were determined according to UV absorption at 365 nm.
[3]Quotients of fluorescent intensities at 8 hours vs. fluorescent intensities at 0 hours, in a time-course fluorescence measurement using 10 μM solutions in HEPES buffer (100 mM, pH 7.4) containing 2% DMSO.
[4]Triacetylated derivative was isolated as the main product.
[5]Diacetylated derivative was isolated as the main product.
Max RFU: maximum relative fluorescence units; n.d.: value not determined due to fluctuation of the experimental data.

As a primary evaluation of photo stability, the decrease in fluorescence intensity of the 80 CyNA compounds was measured (see Table 2). The average decrease in fluorescence intensity after 8 hours of irradiation by a xenon lamp was approximately 18%. A subset of the most photostable compounds (i.e., F/F$_o$ reported in Table 2 was greater than or equal to 95) was examined under stronger irradiation in various buffers. Of these, CyNA-414 had the best photostability, the highest fluorescence quantum yield and the lowest rate of photobleaching ($2.5 \cdot 10^{-6}$ s$^{-1}$) and was, therefore, selected for further examination.

Figure 5:
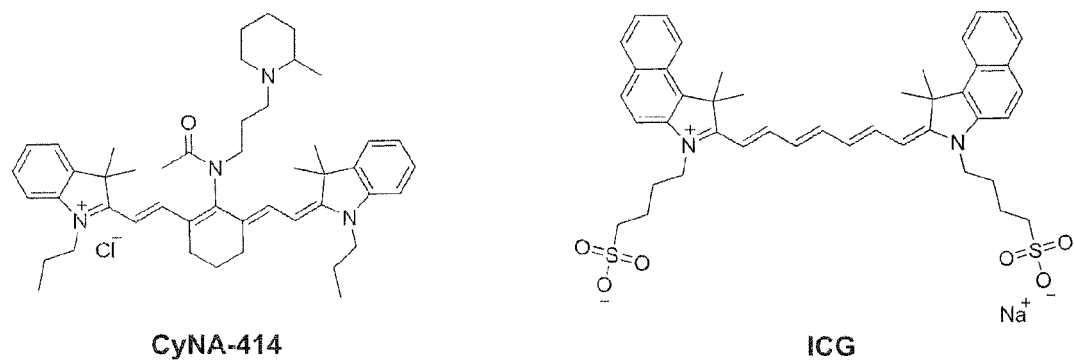
FIG. 5 shows the chemical structures of CyNA-414 and ICG.
Figure 6:
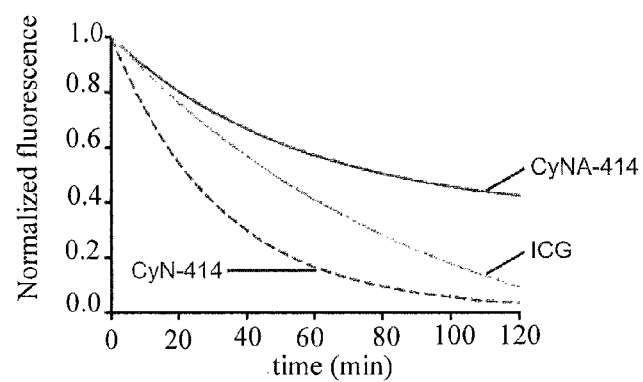
FIG. 6 is a graph of the normalized fluorescence of 10-μM solutions of CyN-414, CyNA-414 and ICG in PBS (pH 7.3) containing 1% DMSO as a function of time of irradiation, and shows the photostabilities of CyN-414, CyNA-414 and ICG.

Since CyNA-414 exhibited outstanding properties as an NIR dye, it was compared to the NIR standard, ICG (FIG. 5). ICG is the only NIR dye clinically approved to date, and has a very similar spectral profile to CyNA-414 (absorption-emission: 790-810 nm). However, ICG has a low quantum yield and poor stability in aqueous media, which has hampered its use in many bioimaging applications. A comparison of the photostabilities of CyNA-414 and ICG is shown in FIG. 6, and indicates that CyNA-414 is more photostable than ICG in aqueous media.

Synthetic Materials and Methods

All the chemicals (building block amines plus others) and solvents were purchased from Sigma Aldrich, Alfa Aesar, Fluka, MERCK or Acros, and used without further purification. $^1$H-NMR and $^{13}$C-NMR spectra were recorded on Bruker Avance 300 NMR and 500 NMR spectrometers, and chemical shifts are expressed in parts per million (ppm). High-resolution mass spectrometry (HRMS) data was recorded on a Micromass VG 7035. Photobleaching experiments were performed using a UVP Blak-Ray® B-100AP high intensity UV lamp (100 W, 365 nm) Spectroscopic and quantum yield data were measured on a SpectraMax M2 spectrophotometer (Molecular Devices), and the data analysis was performed using GraphPrism 5.0. Photobleaching measurements were performed using an Eclipse Ti-U Nikon microscope (filter cube: 750/800) attached to Ti:sappire oscillator that operated in continuous wave mode, and the data was processed using the software NIS-Elements 3.10. In vivo images were taken in an IVIS Spectrum imaging system (Caliper Life Sciences).

Analytical characterization was performed on a HPLC-MS (Agilent-1200 series) with a DAD detector and a single quadrupole mass spectrometer (6130 series) with an ESI probe. Analytical method for CyN and CyNA compounds, unless otherwise indicated: eluent A: H$_2$O (0.1% HCOOH), eluent B: acetonitrile (ACN, 0.1% HCOOH), gradient from 5 to 95% B in 6 minutes; C$_{18}$(2) Luna column (4.6×50 mm$^2$, 5-μm particle size). Analytical method for CyNAMLA compounds, unless otherwise indicated: eluent A: H$_2$O (0.1% HCOOH), eluent B: acetonitrile (ACN, 0.1% HCOOH), gradient from 5 to 100% B in 6 minutes; C$_{18}$(2) Luna column (4.6×50 mm$^2$, 5-μm particle size).

Normal-phase chromatography was carried out using Merck Silica Gel 60 (particle size: 0.040-0.063 mm, 230-400 mesh). Normal-phase purifications of CyN and CyNA compounds were performed using a 10-mL column, eluting with dichloromethane (DCM)-methanol (MeOH) ranging from 100:0 to 97:3.

ICG-sulfo-OSu was purchased from Dojindo Laboratories and anti-EGFR-IgG$_{2a}$ (sc-120) and anti-HER2 (sc-71667, Neu 0.N.211) were supplied by Santa Cruz Biotechnology, Inc. For the preparation of ScFv(anti-HER2) antibody, the V$_H$ and V$_L$ genes of anti-HER2 antibody were amplified and cloned into pComb3X vector containing HA tag. The recombinant plasmid was transformed into E. coli BL21 DE3.

Transformed *E. coli* were grown in SB medium on a shaker at 230 rpm until the optical density (OD) at 600 nm reached 1.0, then induced with 1 mM isopropyl-β-D-thiogalactopyranoside (IPTG) and incubated overnight at 30° C. Soluble scFv was purified via anti-HA antibody-conjugated protein A column.

Surface plasmon absorption spectra were measured on a SpectraMax M2 spectrophotometer (Molecular Devices), and the data analysis was performed using GraphPad Prism 5.0 and Origin 6. SERS measurements were carried out in a Renishaw InVia Raman (UK) microscope with a laser beam directed to the sample through 50× and 20× objective lens and a Peltier cooled CCD detector. Samples were excited with a 785 nm excitation wavelength laser and Stokes shifted Raman spectra were collected in the range of 400 to 2000 cm$^{-1}$ with 1 cm$^{-1}$ resolution. Prior to every measurement, a calibration with a silicon standard (Raman peak centered at 520 cm$^{-1}$) was performed. WiRE 3.0 software package was used for data acquisition.

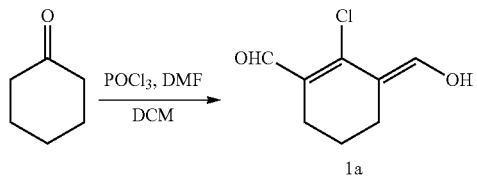 [SMILES: O=C1CCCCC1 ; O=CC1=C(Cl)/C(=C/O)CCC1]

1a

To an ice-cooled solution of N,N-dimethylformamide (DMF) (20 mL, 273 mmol, 5.4 equiv) in 20 mL CH$_2$Cl$_2$ under N$_2$ atmosphere, was added dropwise POCl$_3$ (17.5 ml, 115 mmol, 2.3 equiv) in DCM. After 30 minutes, cyclohexanone (5 g, 50 mmol, 1 equiv) was added, and the resulting mixture was refluxed with vigorous stirring for 3 hours at 80° C., poured into ice-cold water, and kept overnight to obtain 1a as a yellow solid (8.0 g, 92%). $^1$H-NMR (300 MHz, CDCl$_3$): δ=1.57 (m, 2H), 2.35 (t, 4H, J=6.3 Hz), 2.5 (s, 1H), 10.10 (s, 1H). tR: 4.30 min, ESI m/z (C8H9ClO2): calc: 172.0. found: 173.1.

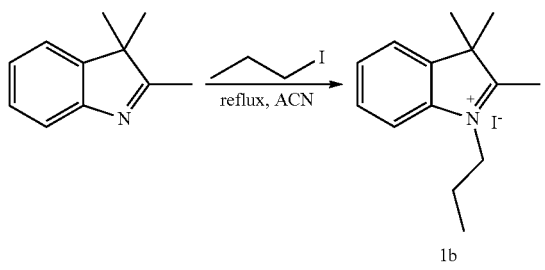

1b

To a solution of 2,3,3-trimethyl-3H-indole (2 g, 12.5 mmol, 1 equiv) in ACN was added 1-iodopropane (10.6 mL, 62 mmol, 5 equiv). The resulting solution was refluxed with continuous stirring for 15 hours. The mixture was dried under high vacuum and washed with Et$_2$O. The resulting solid was recrystallized in acetone to obtain 1b as a white solid (3.9 g, 95%). $^1$H-NMR (300 MHz, DMSO-d$_6$): δ=1.04 (t, 3H, J=7.2), 1.64 (s, 6H), 2.67 (s, 3H), 1.34 (m, 2H), 4.17 (t, 2H, J=7.8 Hz), 7.63 (d, 2H), 7.82 (m, 2H). tR: 2.46 min, ESI m/z (C14H20N$^+$) calc: 202.4. found: 202.1.

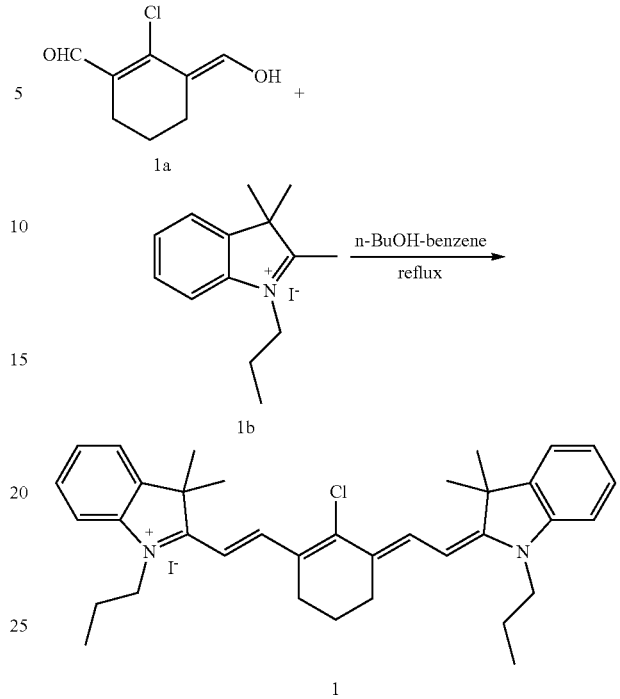

1a (500 mg, 2.9 mmol, 1 equiv) and 1b (1.91 g, 5.81 mmol, 2 equiv) were dissolved in n-butanol (BuOH)-benzene (7:3) under N$_2$ atmosphere, and refluxed at 160° C. for 10 hours with a Dean-Stark condenser. Afterwards, the solvent was evaporated, and the resulting green solid was washed with Et$_2$O and purified by flash chromatography (DCM-MeOH, 50:1) to obtain 1 as a green solid (1.8 g, 96%). $^1$H-NMR (300 MHz, CDCl$_3$) δ=1.06 (t, 6H, J=7.5 Hz), 1.31 (m, 4H), 1.64 (s, 12H), 1.95 (m, 2H), 2.73 (m, 4H), 4.15 (t, 4H, J=6.9 Hz), 6.23 (d, 2H, J=14.2 Hz), 7.15-7.72 (m, 8H), 8.19 (d, 2H, J=13.8 Hz). tR: 5.64 min, ESI m/z (C36H44ClN$_2^+$), calc: 539.4. found: 539.1.

Characterization of CyN-111, 165, 272 and 295

CyN-111 (95 mg, 85%): $^1$H-NMR (300 MHz, CDCl$_3$) δ=1.03 (t, 6H, J=7.5 Hz), 1.31 (m, 2H), 1.62 (s, 12H), 1.83 (m, 4H), 2.47 (t, 4H, J=6.3 Hz), 3.38 (t, 2H, J=5.7 Hz), 3.80 (t, 2H, J=7.2 Hz), 4.17 (t, 4H, J=6.2 Hz), 5.63 (d, 2H, J=12.9 Hz), 6.85-7.72 (m, 12H), 8.52 (d, 2H, J=3.9 Hz).

tR: 5.56 min, HRMS (C$_{43}$H$_{53}$N$_4^+$), calc: 625.4257. found: 625.4265.

CyN-165 (86 mg, 80%): $^1$H-NMR (300 MHz, CDCl$_3$): δ=1.05 (t, 6H, J=7.5 Hz), 1.24 (m, 2H), 1.32 (m, 2H), 1.68 (s, 12H), 1.85 (m, 4H), 2.16 (t, 2H, J=5.4 Hz), 2.47 (t, 4H, J=6.3 Hz), 3.44 (s, 3H), 3.71 (t, 2H, J=5.4 Hz), 3.95 (t, 4H, J=6.3 Hz), 5.61 (d, 2H, J=12.9 Hz), 6.50-7.72 (m, 8H), 7.64 (d, 2H, J=12.9 Hz), 7.92 (bs, 1H).

tR: 5.66 min, HRMS (C$_{40}$H$_{54}$N$_3$O$^+$), calc: 592.4255. found: 592.4261.

CyN-272 (93 mg, 83%): $^1$H-NMR (300 MHz, CDCl$_3$): δ=1.08 (t, 6H, J=7.5 Hz), 1.31 (m, 2H), 1.45 (m, 4H), 1.54 (m, 2H), 1.68 (s, 12H), 1.85 (m, 4H), 2.51 (t, 4H, J=6.3 Hz), 3.44 (t, 6H, J=7.7 Hz), 3.81 (t, 4H, J=6.9 Hz), 4.21 (m, 2H), 5.65 (d, 2H, J=12.9 Hz), 6.80-7.70 (m, 8H), 7.72 (d, 2H, J=12.9 Hz).

tR: 5.62 min, HRMS (C$_{43}$H$_{59}$N$_4^+$), calc: 631.4740. found: 631.4734.

CyN-295 (88 mg, 87%): $^1$H-NMR (300 MHz, CDCl$_3$): δ=1.05 (t, 6H, J=7.5 Hz), 1.56 (t, 3H, J=7.0 Hz), 1.68 (s, 12H), 1.85 (m, 4H), 1.83 (m, 2H), 2.47 (t, 4H, J=6.3 Hz), 3.79 (t, 4H, J=6.9 Hz), 3.96 (m, 2H), 5.62 (d, 2H, J=12.9 Hz), 6.80-7.28 (m, 8H), 7.72 (d, 2H, J=12.5 Hz).

tR: 5.66 min, HRMS ($C_{38}H_{50}N_3^+$), calc: 548.3999. found: 548.3999.

CyN-414 (82 mg, 70%): $^1$H-NMR (300 MHz, CDCl$_3$): δ=1.03 (t, 6H, J=7.5 Hz), 1.24 (d, 3H, J=6.6 Hz), 1.32 (m, 4H), 1.36 (t, 2H, J=5.4 Hz), 1.70 (s, 12H), 1.78-1.85 (m, 11H), 2.02-2.16 (m, 4H), 2.47 (t, 4H, J=5.4 Hz), 3.76 (t, 2H, J=6.0 Hz), 3.93 (t, 2H, J=6.0 Hz), 5.58 (d, 2H, J=14.1 Hz), 6.83 (d, 2H, J=14.1 Hz), 6.83-7.72 (m, 8H).

tR: 5.97 min, ESI-MS ($C_{45}H_{63}N_4^+$), calc: 659.5. found: 659.4.

General Procedure for the CyNA Library Synthesis

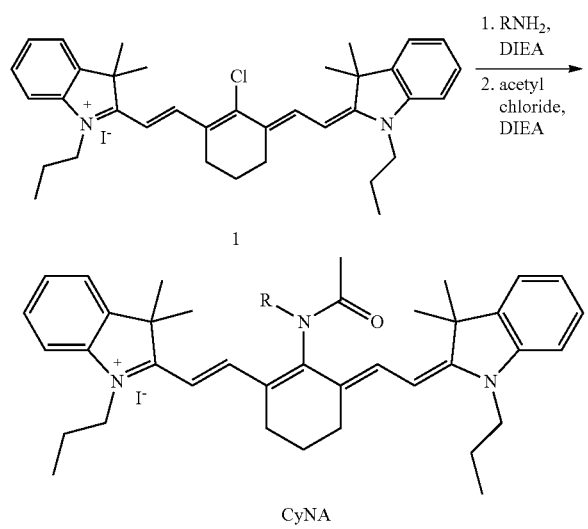

1 (20 mg, 30 μmol, 1 equiv) and a primary amine building block selected from FIGS. 4A-4C (120 μmol, 4 equiv) were dissolved in ACN, and DIEA (7.7 μL, 60 μmol, 2 equiv) was added. The reaction mixture was heated at 80° C. for 10-60 minutes, depending on the reactivity of the amine. The resulting blue mixtures were neutralized with 0.1 N HCl, and concentrated under vacuum. The blue mixtures were then dissolved in DCM under N$_2$ atmosphere, and treated with excess DIEA (96.2 μL, 750 μmol, 25 equiv) and acetyl chloride (11.7 μL, 150 μmol, 5 equiv) at 0° C. for 15 minutes. The final green products were washed with 0.1 N HCl to remove excess DIEA, concentrated under vacuum, and purified by a normal-phase silica short column using DCM-MeOH (ranging from 100:0 to 97:3) as the eluting solvent. The characterization of the whole library was performed by LCMS (Table 1), and selected compounds were also characterized by NMR and high-resolution mass spectrometry (HRMS).

Detailed Characterization of CyNA-111, 165, 272, 295 and 414

CyNA-111 (12 mg, 45%): $^1$H-NMR (300 MHz, CDCl$_3$): δ=1.05 (t, 6H, J=7.5 Hz), 1.29 (m, 2H), 1.63 (s, 6H), 1.65 (s, 6H), 1.72 (m, 4H), 1.94 (t, 4H), 2.05 (s, 3H), 3.09 (m, 2H), 3.63 (m, 2H), 4.18 (t, 4H, J=3.9 Hz), 6.07 (d, 0.3H, J=13.5 Hz), 6.28 (d, 1.7H, J=14.1 Hz), 7.02-7.72 (m, 12H), 8.43 (d, 0.4H, J=14.1 Hz), 8.68 (d, 1.6 H, J=3.3 Hz).

tR: 4.70 min, HRMS ($C_{45}H_{55}ON_4^+$), calc: 667.4370. found: 667.4350.

CyNA-165 (10 mg, 50%): $^1$H-NMR (300 MHz, CDCl$_3$): δ=1.05 (t, 6H, J=7.5 Hz), 1.76 (s, 12H), 1.87-1.92 (m, 8H), 2.58 (t, 4H, J=6.3 Hz), 3.28 (s, 3H), 3.32 (t, 2H, J=5.4 Hz), 3.45 (t, 2H, J=6.3 Hz), 3.92 (t, 4H, J=7.5 Hz), 4.16 (s, 3H), 6.02 (d, 2H, J=13.1 Hz), 6.90-7.30 (m, 8H), 7.35 (d, 2H, J=4.5 Hz).

tR: 6.1 min, HRMS ($C_{42}H_{56}N_3O_2^+$), calc: 634.4367. found: 634.4352.

CyNA-272 (9 mg, 42%): $^1$H-NMR (300 MHz, CDCl$_3$): δ=1.08 (t, 6H, J=7.5 Hz), 1.31 (m, 2H), 1.45 (m, 4H), 1.54 (m, 2H), 1.69 (s, 12H), 1.86 (m, 4H), 1.94 (s, 3H), 2.51 (t, 4H, J=6.3 Hz), 3.44 (t, 6H, J=7.7 Hz), 3.81 (t, 4H, J=6.9 Hz), 4.21 (m, 2H), 5.65 (d, 2H, J=12.9 Hz), 6.80-7.70 (m, 8H), 7.72 (d, 2H, J=12.9 Hz).

tR: 4.24 min, HRMS ($C_{45}H_{61}N_4O^+$), calc: 673.4840. found: 673.4845.

CyNA-295 (9 mg, 48%): $^1$H-NMR (300 MHz, CDCl$_3$): δ=1.05 (t, 6H, J=7.5 Hz), 1.56 (t, 3H, J=7.0 Hz), 1.68 (s, 12H), 1.83 (m, 2H), 1.85 (m, 4H), 1.94 (s, 3H), 2.59 (t, 4H, J=6.3 Hz), 3.79 (t, 4H, J=6.9 Hz), 3.96 (m, 2H), 6.04 (d, 2H, J=14.0 Hz), 6.80-7.28 (m, 8H), 8.14 (d, 2H, J=14.0 Hz).

tR: 4.87 min, HRMS ($C_{40}H_{52}N_3O^+$), calc: 590.4105. found: 590.4113.

CyNA-414 (9 mg, 41%): $^1$H-NMR (300 MHz, CDCl$_3$): δ=1.06 (t, 6H, J=7.5 Hz), 1.24 (d, 3H, J=6.6 Hz), 1.23 (m, 2H), 1.58 (s, 6H), 1.66 (s, 6H), 1.83-2.06 (m, 6H), 1.95 (s, 3H), 2.46-2.56 (m, 4H), 2.82 (t, 2H, J=5.4 Hz), 2.87 (t, 2H, J=5.4 Hz), 3.08 (t, 4H), 2.96-2.98 (m, 2H), 3.08-3.12 (m, 1H), 3.67 (t, 2H, J=6.0 Hz), 4.12 (t, 4H, J=7.2 Hz), 6.21 (d, 1H, J=14.1 Hz), 6.26 (d, 1H, J=14.1 Hz), 7.11 (d, 2H, J=7.5 Hz), 7.20 (d, 2H, J=6.9 Hz), 7.34 (m, 4H), 7.55 (d, 1H, J=14.1 Hz), 7.59 (d, 1H, J=14.1 Hz).

$^{13}$C-NMR (75.5 MHz, CDCl$_3$): 11.6, 11.7, 20.5, 20.6, 20.8, 20.9, 22.9, 23.7, 25.0, 28.1, 28.2, 28.3, 28.5, 28.6, 29.6, 30.8, 46.2, 46.2, 49.2, 49.3, 102.2, 110.7, 110.8, 122.3, 125.3, 125.4, 128.2, 128.4, 128.6, 140.9, 141.0, 142.2, 154.2, 170.4, 172.1.

tR: 4.32 min, HRMS ($C_{47}H_{65}N_4O^+$), calc: 701.5153. found: 701.5147.

The absorbance and fluorescence maximum wavelengths and extinction coefficients of CyN-111, 165, 272 and 295 were measured using 10-μM solutions of CyN-111, CyN-165, CyN-272 or CyN-295 in 10 mM HEPES buffer (pH 7.4) containing 1% DMSO. Quantum yields were measured in DMSO, using Cardiogreen as a standard (φ: 0.13, in DMSO). The results are reported in Table 3.

TABLE 3

Absorbance ($λ_{abs}$) and fluorescence ($λ_{em}$) maximum wavelengths, quantum yields, and extinction coefficients of CyN-111, CyN-165, CyN-272 and CyN-295.

| compound | $λ_{abs}$(nm) | $λ_{em}$(nm) | φ | ε(cm$^{-1}$M$^{-1}$) |
|---|---|---|---|---|
| CyN-111 | 640 | 760 | 0.42 | 0.538 · 10$^5$ |
| CyN-165 | 640 | 762 | 0.37 | 0.352 · 10$^5$ |
| CyN-272 | 635 | 765 | 0.41 | 0.516 · 10$^5$ |
| CyN-295 | 640 | 760 | 0.35 | 0.519 · 10$^5$ |

Characterization of CyN-111c $^1$H-NMR (300 MHz, CDCl$_3$) δ=0.98 (t, 3H, J=7.5 Hz), 1.65 (s, 6H), 1.69-1.77 (m, 2H), 3.63 (t, 3H, J=9.0 Hz), 5.43 (d, 1H, J=9.0 Hz), 6.82 (d, 1H, J=7.5 Hz), 7.04 (t, 1H, j=7.5 Hz), 7.22-7.28 (m, 2H), 9.98 (d, 1H, J=9.0 Hz).

Time-course Fluorescence Measurements of CyN-111, 165, 272 and 295, CyNA-111, 165, 272 and 295 and 1

10-μM solutions of CyN(A) or 1 in 10 mM HEPES buffer (pH 7.4) containing 1% DMSO were placed in a 96-well black plate, and fluorescence intensity measurements were recorded every 10 minutes for a total period of 10 hours (excitation-emission: 640-750 nm for CyN derivatives, and 790-820 nm for 1 and CyNA derivatives). Values were fitted to a non-linear regression one-phase exponential decay (GraphPad Prism 5.0). Detailed statistics for the one-phase decay analysis of the CyN compounds and 1 follow:

| | Goodness of Fit | | | | |
|---|---|---|---|---|---|
| | CyN-111 | CyN-165 | CyN-272 | CyN-295 | 1 |
| Degrees of Freedom | 57 | 57 | 57 | 57 | 57 |
| $R^2$ | 0.9967 | 0.9988 | 0.9971 | 0.9981 | 0.8433 |
| Absolute Sum of Squares | 0.008321 | 0.002994 | 0.007014 | 0.00426 | 0.04572 |
| Sy · x | 0.01208 | 0.007247 | 0.01109 | 0.008645 | 0.02832 |
| Number of points analyzed | 60 | 60 | 60 | 60 | 60 |

Detailed statistics for the one-phase decay analysis of the CyNA compounds follow:

| | Goodness of Fit | | | |
|---|---|---|---|---|
| | CyNA-111 | CyNA-165 | CyNA-272 | CyNA-295 |
| Degrees of Freedom | 57 | 57 | 57 | 57 |
| $R^2$ | 0.9736 | 0.9664 | 0.9259 | 0.9418 |
| Absolute Sum of Squares | 0.002442 | 0.006335 | 0.004751 | 0.009447 |
| Sy · x | 0.006546 | 0.01054 | 0.00913 | 0.01287 |
| Number of points analyzed | 60 | 60 | 60 | 60 |

Photodecomposition rate constants were determined by plotting $-\ln(F/F_0)$ vs time, and calculated using a pseudo-first order rate equation. See Licha, K., et al., *Photochem. Photobiol.* 2000, 72, 392-398.

Time-Course Fluorescence Measurements of the CyNA Library

Primary Screening:

10-μM CyNA solutions in 100 mM HEPES buffer (pH 7.4) containing 2% DMSO were placed in a 96-well black plate, and fluorescence intensity measurements were recorded every 10 minutes for a total period of 8 hours (excitation-emission: 790-820 nm). The results are given in Table 1. A subset of fourteen compounds selected according to their $F_{8h}/F_o$ quotients, quantum yields and maximum relative fluorescence units (RFU) values was further evaluated in a secondary screening Secondary Screening:

10-μM CyNA solutions in 10 mM HEPES buffer (pH 7.4) or PBS (pH 7.3) containing 1% DMSO were placed in a 96-well black plate, and irradiated for periods of 15 minutes up to 2 hours with a high-intensity UV lamp (100 W, 365 nm) at a 2-cm distance. Values are represented as means (n=2), and fitted to a non-linear regression one-phase exponential decay (GraphPad Prism 5.0). Results not shown.

Photostability Measurements of CyN-414 and ICG

10-μM solutions of CyN-414, CyNA-414 and ICG in PBS (pH 7.3) containing 1% DMSO were placed in a 96-well black plate, and irradiated for periods of 10 minutes up to 2 hours with a high-intensity UV lamp (100 W, 365 nm) at a 2-cm distance. Values are represented as means (n=6), and fitted to a non-linear regression one-phase exponential decay (GraphPad Prism 5.0). The results are shown in FIG. 6.

Rates of Photobleaching of CyNA-414 and CyN-414

10-μM solutions of CyNA-414 and CyN-414 in 10 mM HEPES buffer (pH 7.4) containing 1% DMSO were placed in a 96-well black plate, and fluorescence intensity measurements (n=3) were recorded every 10 minutes for a total period of 12 hours (excitation-emission: 640-750 nm for CyN-414, and 790-820 nm for CyNA-414) under a xenon flash lamp. Table 4 reports the values for the rates of photobleaching. Values were fitted to a non-linear regression one-phase exponential decay (GraphPad Prism 5.0).

TABLE 4

Rates of Photobleaching of CyNA-414 and CyN-414.

| compound | k (s$^{-1}$) | $k_{CyN}/k_{CyNA}$ |
|---|---|---|
| CyN-414 | $17.5 \cdot 10^{-6}$ | — |
| CyNA-414 | $2.5 \cdot 10^{-6}$ | 7 |

Example 2

A Photostable NIR Labeling Dye for In Vivo Imaging

Although CyNA-414 exhibited very good properties as a NIR dye, it lacked a reactive group that enabled its use in protein labeling. CyNA-414 was equipped for bioconjugation purposes by replacing the electron-withdrawing acetyl group with a glutaric acid moiety. The glutaric acid moiety enabled convenient functionalization of the CyNA core with a reactive succinidimyl ester group and preserved the electron-withdrawing effect of the original acetyl group, which was critical to retaining a good photostability profile. CyNE790 was prepared by a three-step sequence (vide infra). Notably, the hydrolysis of methyl ester 2 to afford the corresponding carboxylic acid 3 required a rigorous evaluation of the reaction conditions, since tricarbocyanine compounds are inherently labile under strongly acidic or basic conditions. Treatment of 2 with a solution of HCl in CHCl$_3$-tetrahydrofuran (THF)-H$_2$O (6:3:2) furnished 3, which was isolated after normal-phase chromatography. CyNE790 was readily prepared from 3 by derivatization with N-hydroxysuccinimide. The spectral characterization of CyNE790 demonstrated that the incorporation of the linker did not affect the maximum excitation and emission wavelengths, the fluorescence emission intensity, or the photostability of the original compound, CyNA-414.

Figure 7A:
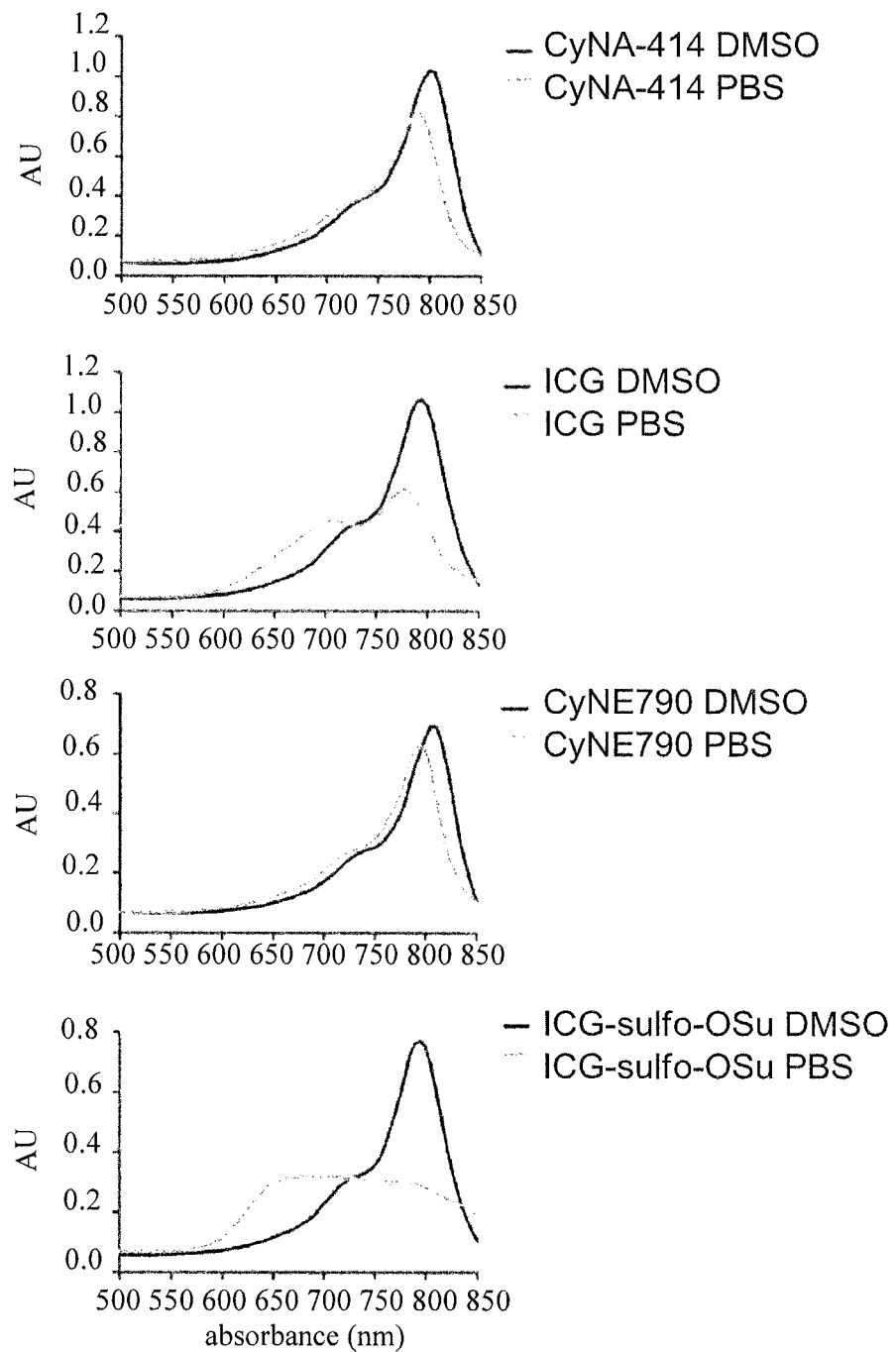
FIG. 7A is an absorbance spectrum of 10-μM solutions of CyNA-414, CyNE790, ICG and ICG-sulfo-OSu in DMSO and PBS.
Figure 7B:
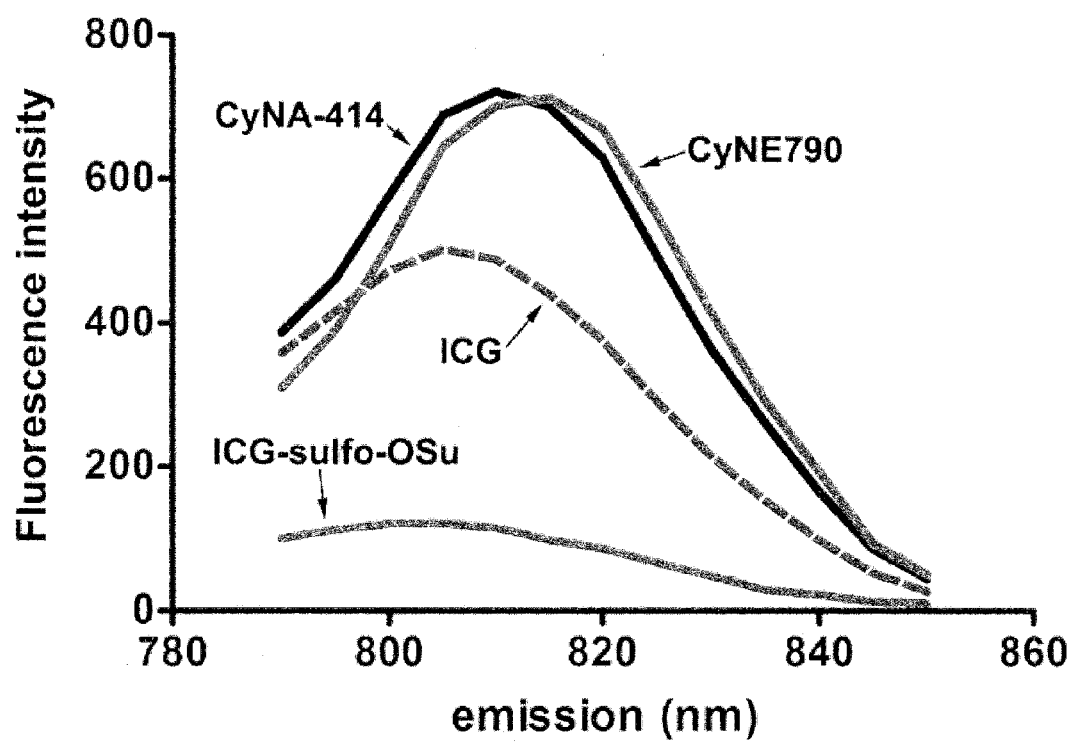
FIG. 7B is a fluorescence spectrum of CyNA-414, CyNE790, ICG and ICG-sulfo-OSu as 10-μM solutions in PBS containing 1% DMSO measured using an excitation wavelength of 760 nm.

After corroborating the spectral properties of CyNE790 as a fluorescent NIR dye, its applicability for protein conjugation was assessed by comparing CyNE790 to ICG-sulfo-OSu, the commercially available succinidimyl ester of ICG. FIG. 7A shows that ICG has a similar spectral profile to CyNE790 (absorption-emission: 790-810 nm). However, the application of ICG to molecular imaging has been limited because its fluorescence is drastically quenched after protein conjugation. Moreover, ICG derivatives have several disadvantages that hamper their use in bioimaging, including low quantum yield, poor photostability and the formation of aggregates in aqueous media. FIG. 7B shows that CyNE790 has superior fluorescent properties to both ICG and ICG-sulfo-OSu. Table 5 shows that CyNE790 also has a higher fluorescence quantum yield in aqueous media than ICGsulfo-OSu, suggesting that CyNE790 has significant advantages for biological applications, which often involve aqueous environments.

TABLE 5

Photophysical properties of CyNE790 and ICG-sulfo-OSu.

| Compound | Quantum Yield (DMSO)[a] | Quantum Yield (aqueous media)[b] | $\epsilon$ ($M^{-1} \cdot cm^{-1}$) (aqueous media)[b] |
|---|---|---|---|
| CyNE790 | 13% | 3.3% | 108,000 |
| ICG-sulfo-OSu | 12% | 0.4% | 42,000 |

[a]ICG was used as a standard in DMSO and in aqueous media.
[b]Dyes were dissolved in PBS buffer (pH 7.3) containing 0.1% DMSO.

Figure 8:
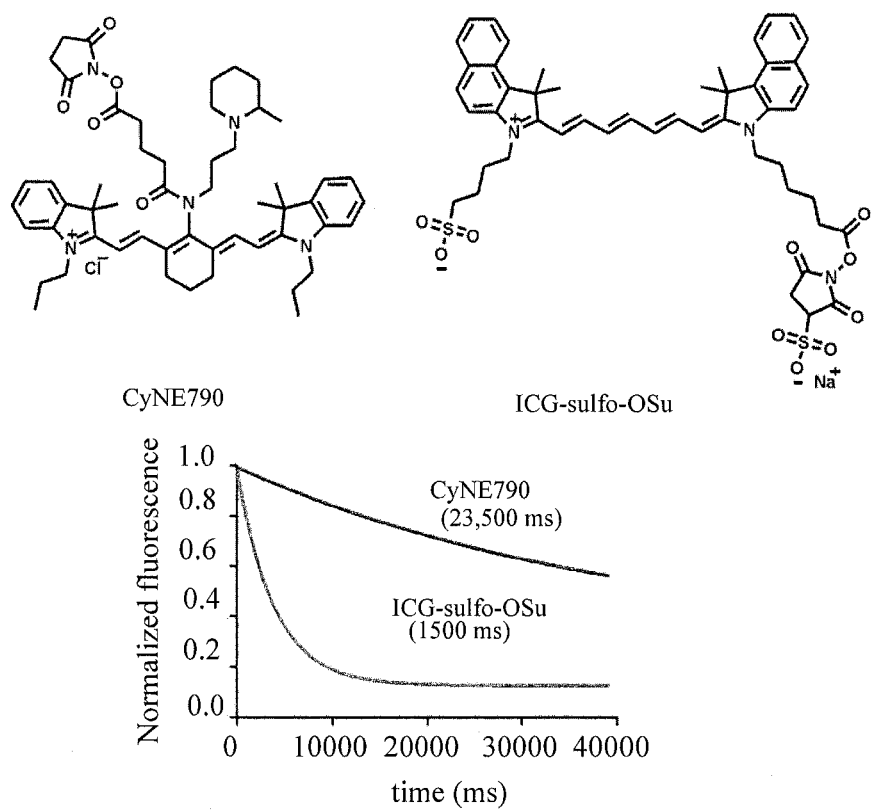
FIG. 8 is a graph of the normalized fluorescence of 10-μM solutions of CyNE790 and ICG-sulfo-OSu in PBS (pH 7.3) containing 1% DMSO as a function of time, and shows the chemical structures of CyNE790 and ICG-sulfo-OSu [values are represented as means (n=3) for sequential measurements taken every 500 ms; the time needed to bleach 35% of the maximum fluorescence intensity for each compound is indicated in parentheses in the figure].

The formation of aggregates in aqueous solution can be measured by comparing an absorbance spectrum of a compound in DMSO to an absorbance spectrum of the same compound in an aqueous solution. FIG. 7A shows the absorbance maximum values of ICG-sulfo-OSu shifted from 780 nm in DMSO to 695 nm in PBS, indicating the formation of aggregates. In contrast, the spectral profile of CyNE790 is substantially similar in DMSO and PBS, indicating little to no formation of aggregates. Furthermore, a detailed evaluation of the photobleaching of ICG-sulfo-OSu and CyNE790 in buffer revealed that the photostability of CyNE790 was 15-fold greater than the photostability of ICG-sulfo-OSu (FIG. 8).

Figure 9:
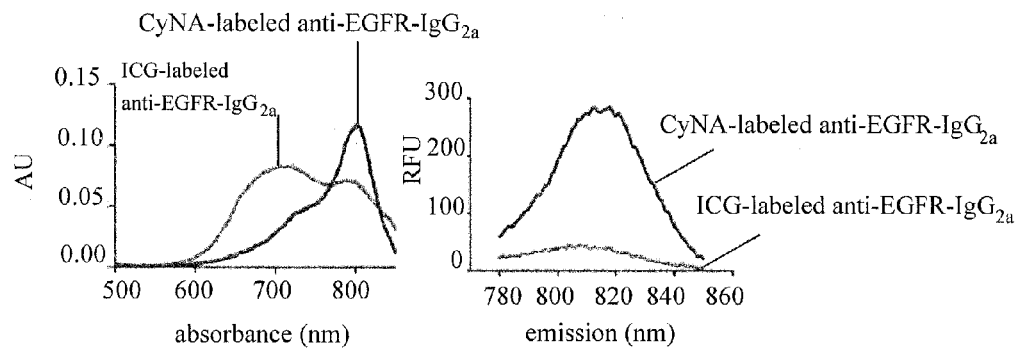
FIG. 9 is an absorbance spectrum (left) and a fluorescence spectrum (right) of CyNE790-labeled EGFR-IgG$_{2a}$ and ICG-labeled EGFR-IgG$_{2a}$ antibodies (emission spectrum was measured using an excitation wavelength of 750 nm).
Figure 10:
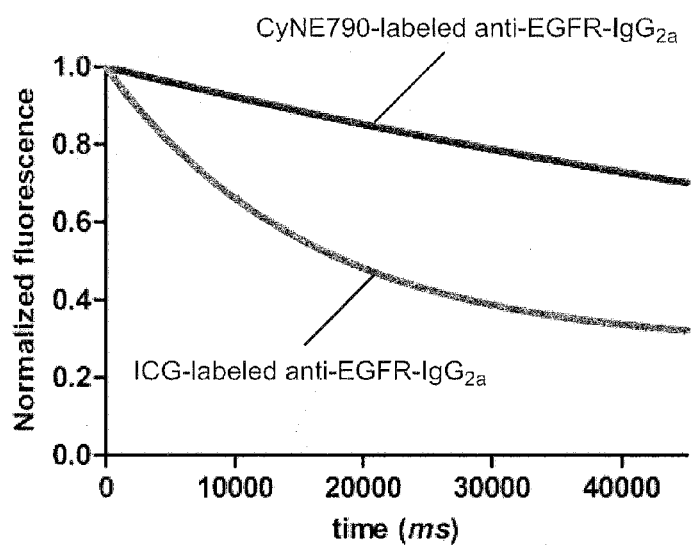
FIG. 10 is a graph of the normalized fluorescence of CyNE790-labeled IgG$_{2a}$ and ICG-labeled IgG$_{2a}$ as a function of time.
Figure 11:
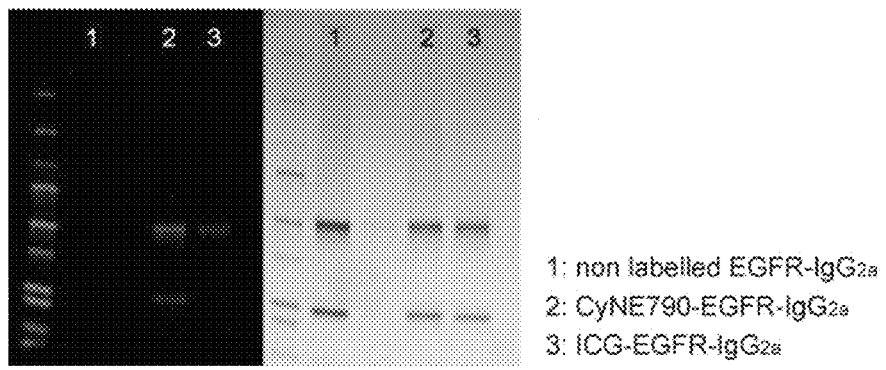
FIG. 11 is a fluorescence image of a gel containing CyNE790- and ICG-labeled EGFR-IgG$_{2a}$ following SDS-PAGE (left) and an image of a gel containing CyNE790- and ICG-labeled EGFR-IgG$_{2a}$ stained with Coomassie Blue following SDS-PAGE (middle).

To compare CyNE790 and ICG-sulfo-OSu for in vivo imaging studies, each reactive ester was conjugated to a monoclonal anti-epidermal growth factor receptor (EGFR) antibody. FIG. 9 shows the absorbance and fluorescence spectra of CyNE790-labeled EGFR-IgG$_{2a}$ and ICG-labeled EGFR-IgG$_{2a}$. FIG. 10 shows the normalized fluorescence intensity of CyNE790-labeled EGFR-IgG$_{2a}$ and ICG-labeled EGFR-IgG$_{2a}$ as a function of time. CyNE790 maintains its superior fluorescence intensity and photostability after protein conjugation.

Figure 13A:
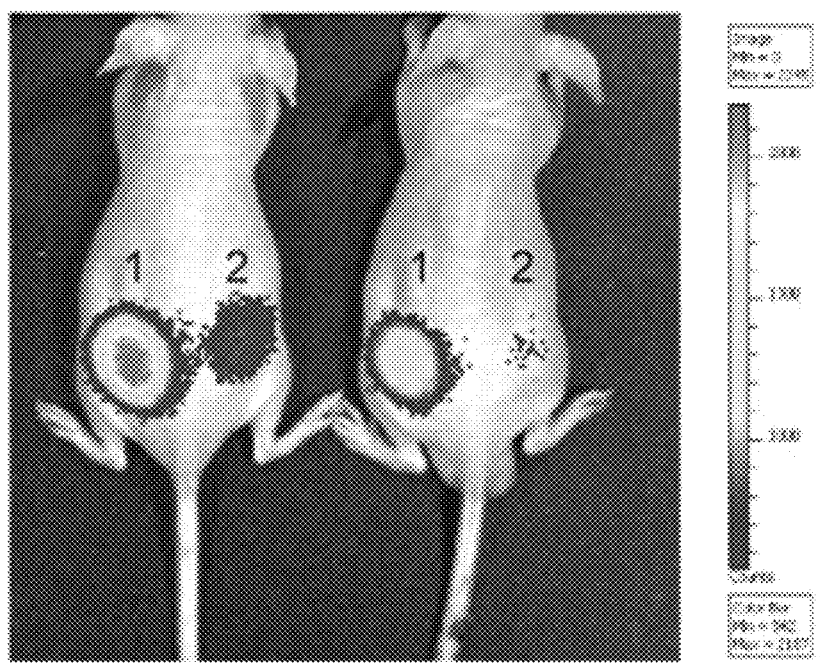
FIG. 13A is a fluorescence image of mice after injection with CyNE790-labeled EGFR-IgG$_{2a}$ (left mouse) or with ICG-labeled EGFR-IgG$_{2a}$ (right mouse) [protein amount per site: 0.85 μg at site 1 (left flank), 0.15 μg at site 2 (right flank)].

The better fluorescence properties of the CyNE790-labeled antibody were further demonstrated by examining the NIR emission of both the CyNE790-labeled and ICG-labeled antibodies in mice. FIG. 13A is a fluorescence image of mice after injection with CyNE790-labeled EGFR-IgG$_2$, or with ICG-labeled EGFR-IgG$_{2a}$. The CyNE790-labeled antibody displayed a stronger fluorescence signal than the same amount of ICG-labeled antibody, enabling in vivo imaging with a significantly lower detection limit.

Figure 12A:
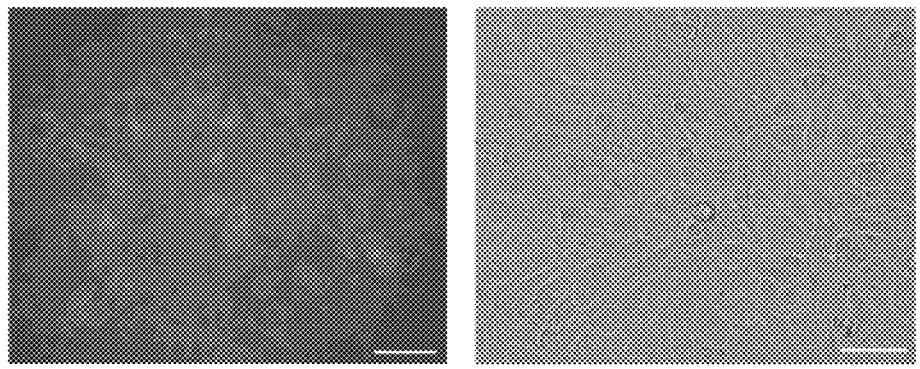
FIG. 12A is a NIR-fluorescence image (left) or a bright-field image (right) of SCC-15 cells after incubation with CyNE790-anti-EGFR (scale bar=80 μm).
Figure 12B:
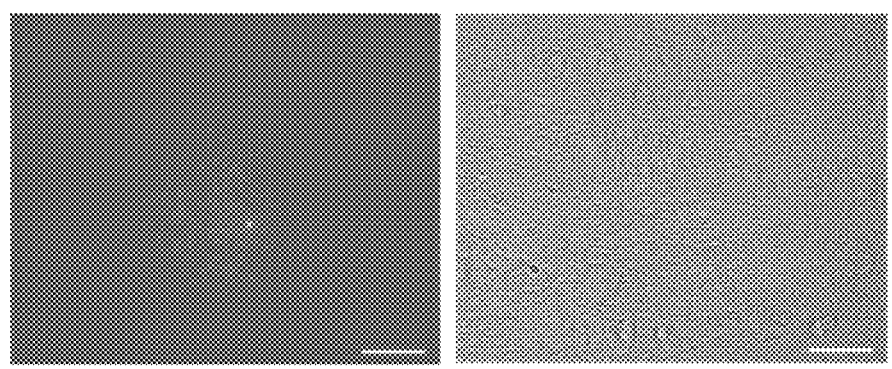
FIG. 12B is a NIR-fluorescence image (left) or a bright-field image (right) of MCF-7 cells after incubation with CyNE790-anti-EGFR (scale bar=80 μm).
Figure 13B:
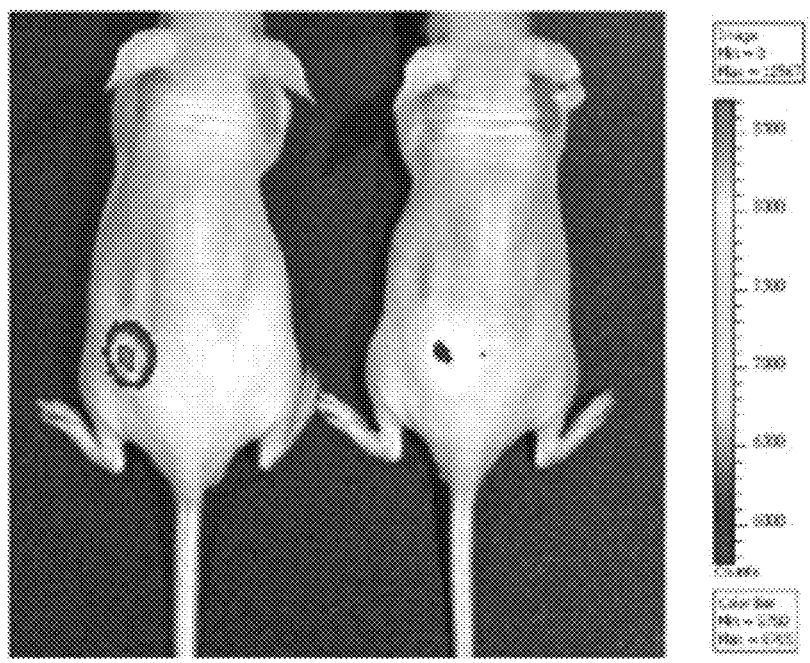
FIG. 13B is a fluorescence image of mice after injection with CyNE790-EGFR-IgG$_{2a}$-treated SCC-15 cells (left flank, left mouse) or with CyNE790-EGFR-IgG$_{2a}$-treated MCF-7 cells (left flank, right mouse).
Figure 14A:
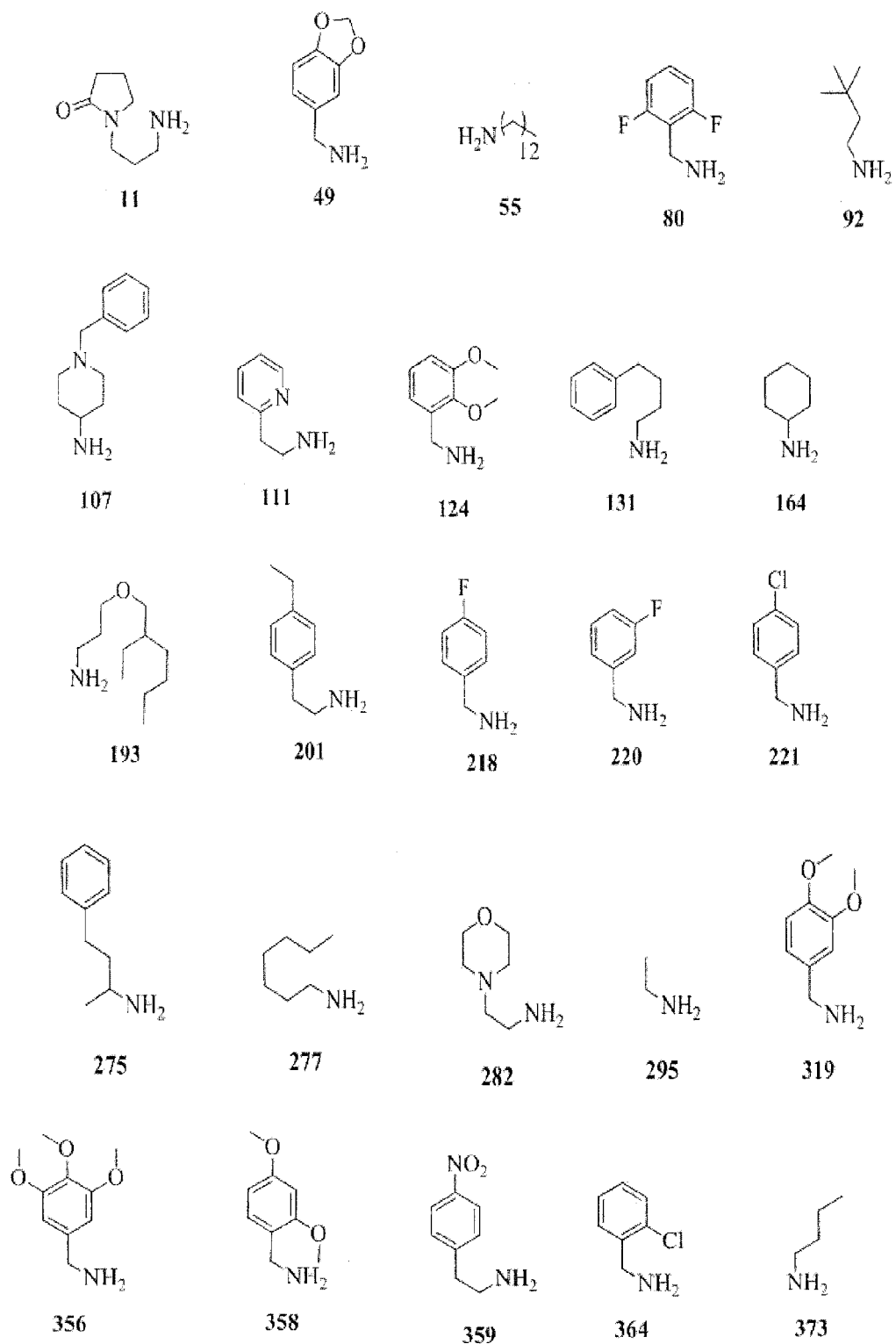
FIGS. 14A-14D show the chemical structures of the amine building blocks used to construct the CyNAMLA library.
Figure 14B:
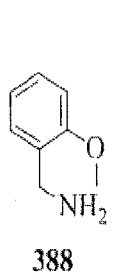
Figure 14B:
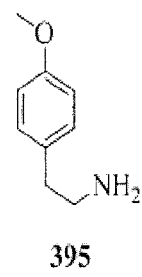
Figure 14B:
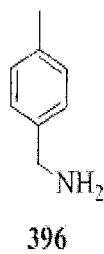
Figure 14B:
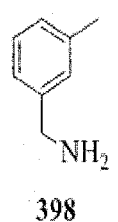
Figure 14B:
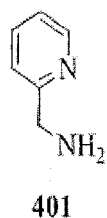
Figure 14B:
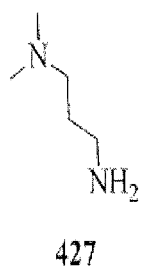
Figure 14B:
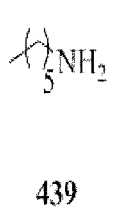
Figure 14B:
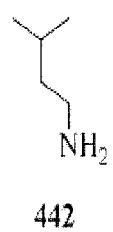
Figure 14B:
Figure 14B:
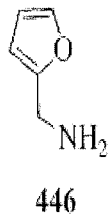
Figure 14B:
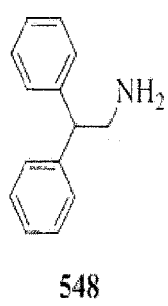
Figure 14B:
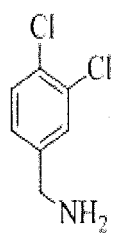
Figure 14B:
Figure 14B:
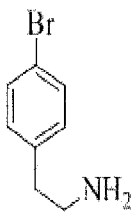
Figure 14B:
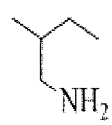
Figure 14B:
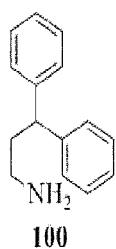
Figure 14B:
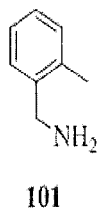
Figure 14B:
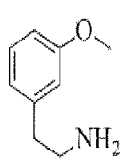
Figure 14B:
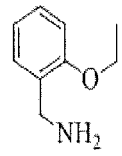
Figure 14B:
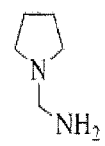
Figure 14C:
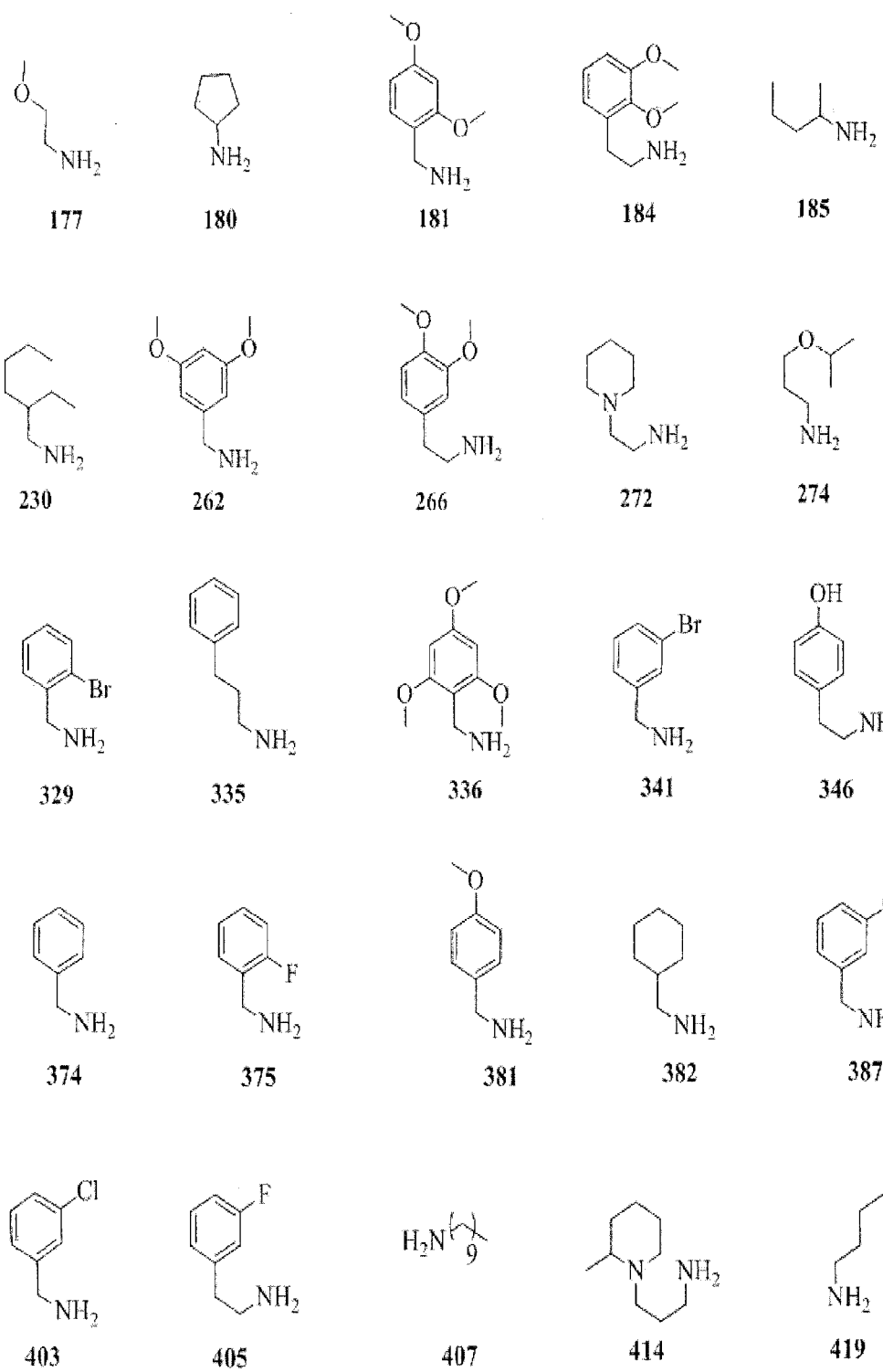
Figure 14D:
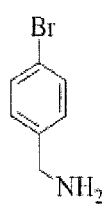
Figure 14D:
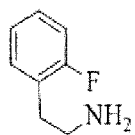
Figure 14D:
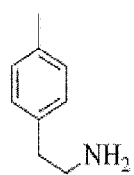
Figure 14D:
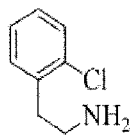
Figure 14D:
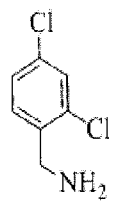
Figure 14D:
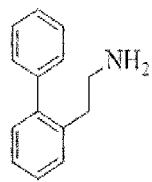
Figure 14D:
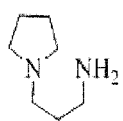
Figure 14D:
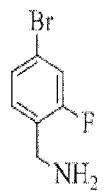
Figure 14D:
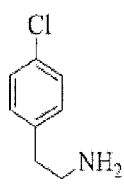
Figure 14D:
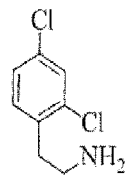

The applicability of CyNE790 to the specific detection of a target was demonstrated by detecting EGFR-expressing cells with the CyNE790-labeled anti-EGFR. SCC-15 and MCF-7 are human cancer cell lines with respectively high and low expression levels of EGFR, a known target protein for tumor diagnosis and anticancer therapy. FIGS. 12A and 12B are images of SCC-15 and MCF-7 cells obtained after incubation with CyNE790-labeled anti-EGFR. Brighter staining was observed in SCC-15 cells, which corresponds to the higher expression level of EGFR in SCC-15 cells. Furthermore, the injection of CyNE790-anti-EGFR-treated SCC-15 and MCF-7 cells into mice allowed the visualization of CyNE790-labeled cells in vivo. FIG. 13B shows that the mouse that received SCC-15 cells has a higher intensity signal than the mouse that received MCF-7 cells. This correlates well with the relative expression levels of EGFR in the two cell lines.

In conclusion, CyNE790 is a highly fluorescent and photostable NIR protein labeling dye. CyNE790 incorporates a glutaric acid linker that enables protein bioconjugation and preserves the excellent photostability and NIR fluorescence intensity of the amine acetylated tricarbocyanine scaffold. Upon protein conjugation, the fluorescent properties of CyNE790 were maintained, and proved to be superior to the NIR standard ICG-sulfo-OSu for in vivo NIR imaging.

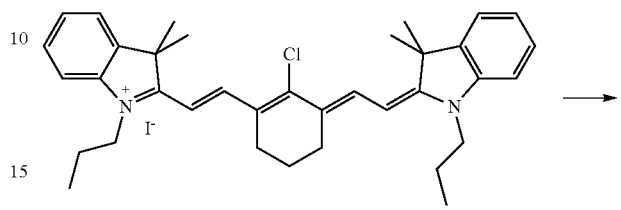

1

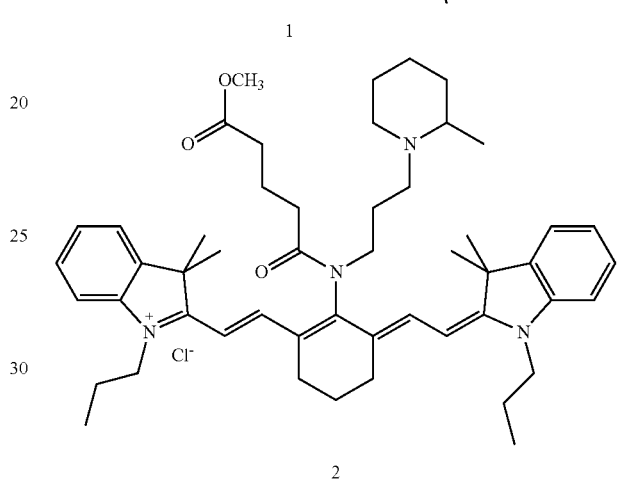

2

1 (300 mg, 0.45 mmol, 1 equiv) and 1-(3-aminopropyl)-2-pipecoline (170 mg, 0.9 mmol, 2 equiv) were dissolved in ACN (2 mL), and DIEA (87 µL, 0.67 mmol, 1.5 equiv) was added. The reaction mixture was heated at 80° C. for 40 minutes, and the resulting blue mixture was neutralized with 0.1 N HCl and concentrated under vacuum. The blue mixture was dissolved in DCM under $N_2$ atmosphere, and treated with excess DIEA (700 µL, 5.39 mmol, 12 equiv) and methyl 4-(chloroformyl)butyrate (110 µL, 0.67 mmol, 1.5 equiv) at 0° C. for 15 minutes. The resulting green product 2 was washed with 0.1 N HCl and brine, concentrated under vacuum, and used without further purification.

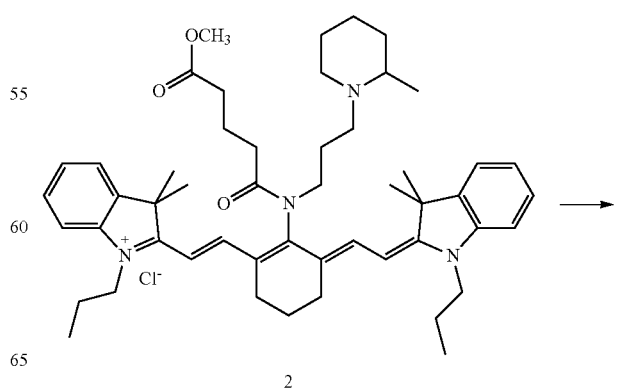

2

-continued

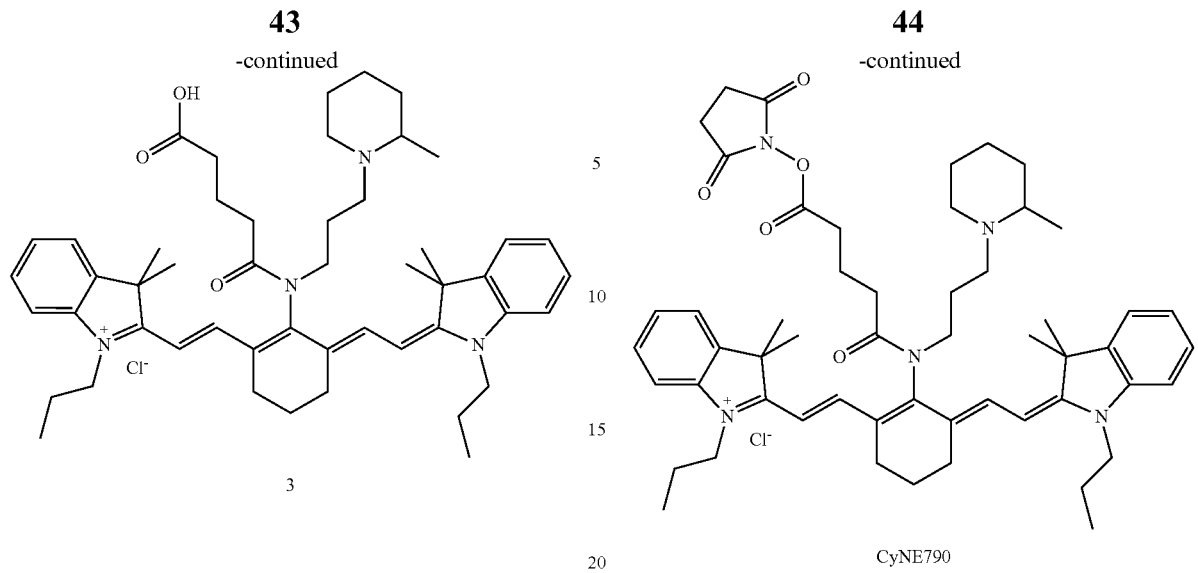

3

2 (360 mg, 0.41 mmol) was dissolved in 40 mL of $CHCl_3$, and a mixture of $THF:H_2O:HCl_{conc}$ (3:2:1, 40 mL) was slowly added with continuous stirring at 0° C. After 5 minutes, the reaction mixture was brought to reflux and was refluxed at 80° C. for 12 hours. After complete hydrolysis of the methyl ester, $CHCl_3$ was added to the reaction mixture, the organic layer was collected, washed with $H_2O$ and purified by normal-phase chromatography using DCM-MeOH (from 100:0 to 88:12) as the eluting solvent. 3 was obtained as a green solid (70 mg, yield 20%).

Characterization data for 3 (70 mg, 20% from 1): $^1$H-NMR (300 MHz, $CDCl_3$): 1.06 (t, 6H, J=7.5 Hz), 1.24 (d, 3H, J=6.6 Hz), 1.39 (m, 2H), 1.61 (s, 6H), 1.62 (s, 6H), 1.79-1.95 (m, 6H), 2.22 (t, 2H, J=7.8 Hz), 2.33 (t, 2H, J=6.6 Hz), 2.52-2.56 (m, 4H), 2.82 (t, 2H, J=5.4 Hz), 2.87 (t, 2H, J=5.4 Hz), 2.96-2.98 (m, 2H), 3.09-3.12 (m, 1H), 3.36 (t, 4H), 3.53 (t, 21-1, J=6.6 Hz), 3.67 (t, 2H, J=6.6 Hz), 4.06 (t, 2H, 4.2 Hz), 4.15 (t, 2H, J=4.8 Hz), 6.15 (d, 1H, J=14.1 Hz), 6.20 (d, 1H, J=14.1 Hz), 7.07-7.38 (m, 8H), 7.51 (d, 1H, J=14.1 Hz), 7.60 (d, 1H, J=14.1 Hz). $^{13}$C-NMR (75 MHz, $CDCl_3$): 11.6, 12.2, 19.5, 20.4, 20.6, 20.7, 22.2, 22.9, 24.8, 28.1, 28.2, 28.3, 31.3, 32.3, 41.9, 43.9, 48.3, 49.1, 49.3, 50.2, 51.8, 53.7, 60.4, 101.5, 101.9, 102.4, 106.2, 110.6, 110.8, 114.9, 118.8, 122.3, 125.5, 125.6, 127.7, 128.1, 128.6, 140.6, 140.9, 141.4, 142.1, 142.2, 144.6, 153.9, 160.9, 161.4, 171.7, 172.5, 173.6, 174.3.

tR: 4.13 min, ESI (HRMS) m/z ($C_{50}H_{69}N_4O_3^+$), calc: 773.5364. found: 773.5351.

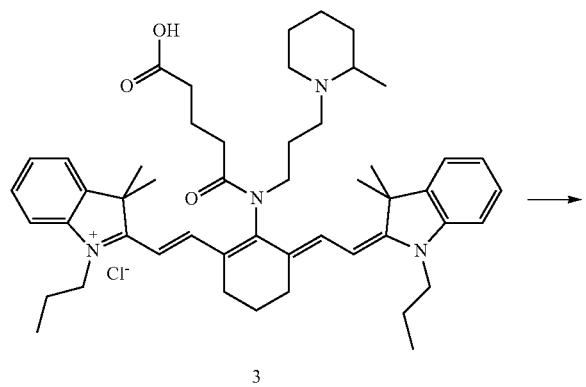

3

→

-continued

CyNE790

N,N'-dicyclohexylcarbodiimide (11 mg, 56 µmol) and 3 (30 mg, 37 µmol) were dissolved in anhydrous THF (2 mL), stirred for 10 minutes at room temperature, and mixed with N-hydroxysuccinimide (7 mg, 59 µmol). The reaction mixture was stirred at room temperature for 12 hours, washed with $Et_2O$, concentrated under reduced pressure, and purified by normal-phase chromatography using DCM-MeOH (from 100:0 to 94:6) as the eluting solvent. CyNE790 was isolated as a green solid (21 mg, yield 65%).

Characterization data for CyNE790 (31 mg, 92%): $^1$H-NMR (300 MHz, $CDCl_3$): 1.06 (t, 6H, J=7.5 Hz), 1.22 (d, 3H, J=6.6 Hz), 1.39 (m, 2H), 1.61 (s, 6H), 1.62 (s, 6H), 1.79-1.95 (m, 6H), 2.22 (t, 2H, J=7.8 Hz), 2.33 (t, 2H, J=6.6 Hz), 2.52-2.56 (m, 4H), 2.64 (s, 2H), 2.68 (s, 2H), 2.82 (t, 2H, J=5.4 Hz), 2.87 (t, 2H, j=5.4 Hz), 2.96-2.98 (m, 2H), 3.09-3.12 (m, 1H), 3.36 (m, 4H), 3.53 (t, 2H, J=6.6 Hz), 3.67 (t, 2H, J=6.6 Hz), 4.06 (t, 2H, 4.2 Hz), 4.15 (t, 2H, J=4.8 Hz), 6.15 (d, 1H, J=14.1 Hz), 6.20 (d, 1H, J=14.1 Hz), 7.07-738 (m, 8H), 7.51 (d, 1H, J=14.1 Hz), 7.60 (d, 1H, J=14.1 Hz). $^{13}$C-NMR (75 MHz, $CDCl_3$): 11.6, 12.3, 20.1, 20.5, 20.8, 22.9, 24.8, 25.4, 25.5, 25.7, 28.1, 28.2, 28.3, 28.4, 29.6, 30.2, 31.6, 32.4, 33.9, 46.1, 46.2, 48.2, 49.1, 49.2, 49.3, 101.8, 102.2, 110.6, 110.8, 110.9, 122.3, 122.4, 125.3, 125.4, 125.6, 128.0, 128.3, 128.5, 128.7, 140.7, 140.9, 141.0, 141.1, 142.1, 142.2, 153.3, 153.9, 167.9, 168.9, 172.0, 172.2, 172.3, 172.7, 173.6.

tR: 4.20 min, ESI (HRMS) m/z ($C_{54}H_{72}N_5O_5^+$), calc: 870.5528. found: 870.5534.

Synthesis and Characterization of CyNE790-Anti-EFGR-$IgG_{2a}$ and ICG-Anti-EFGR-$IgG_{2a}$ 100 µg of anti-EGFR-$IgG_{2a}$ were washed with PBS using a Microcon 3K filter (Millipore), and re-suspended in 100 µL of $Na_2CO_3$—$NaHCO_3$ buffer (pH 9.2). 20 equiv of CyNE790 or ICG-sulfo-OSu (typically 1.0-1.2 µL of a 10 mM solution in DMSO) were added and the whole mixture was shaken in the dark for 2 hours. The excess dye was removed by washing with PBS (3×500 µL) using a Microcon 3K filter (Millipore) (3 rounds at 14,000 rpm at 4° C. for 60 min).

Both antibodies were prepared with a similar dye/protein (D/P) ratio. D/P ratios were determined using reported procedures:

$$D/P = (A_{790}/\epsilon_{790})/\{(A_{280}-\Theta \times A_{790})/170,000\}$$

$\epsilon_{790}$ is the extinction coefficient of the dye in PBS (790 nm) and $\Theta$ is the ratio $\epsilon_{280}/\epsilon_{790}$ for each dye. See Southwick, P. L., et al., *Cytometry* 1990, 11, 418-430.

0.25-μg protein/4 solutions in PBS (pH 7.3) were fixed in a glass coverslide, and irradiated with a diode laser (95 mW, 740 nm, time frame: 500 ms, no delay). Emission was recorded with a NIR-enhanced CCD camera (Andor Technology) adapted to an Eclipse Ti-U microscope (40× magnification, filter cube 750/800), and images were processed using the software NIS-Elements 3.10. The resulting values are represented as means (n=3), and fitted to a non-linear regression one-phase exponential decay (GraphPad Prism 5.0). The results are shows in FIG. 10.

Cell Imaging Data of CyNE790-Anti-EGFR in SCC-15 and MCF-7 Cells

SCC-15 and MCF-7 cell lines were grown using RPMI media supplemented with 10% fetal bovine serum (FBS), 2 mM L-glutamine, and antibiotics (100 U/mL penicillin and 100 μg/mL streptomycin) in a humidified atmosphere at 37° C. with 5% $CO_2$. Both cell lines were cultured in 96-well plates at 85-90% confluence and incubated with CyNE790-anti-EGFR for 1 hour at room temperature (1:50 dilution of a 1 μg/μL antibody solution in PBS). After incubation, cells were washed with media and images were taken (10× magnification) using an Eclipse Ti-U Nikon microscope (filter cube: 750/800) attached to Ti:sappire oscillator that operated in continuous wave mode (750 nm, 120 mW), and a NIR-enhanced CCD camera (Andor Technology). The results are shown in FIGS. 12A and 12B.

In Vivo Imaging Procedures for CyNE790- and ICG-Labeled Anti-EGFR

Balb/c nude mice obtained from the Biological Resource Centre (Biomedical Sciences Institutes) were anesthetized by intraperitoneal injection of a mixture of ketamine (150 mg/kg)/xylazine (10 mg/kg) at the age of 8 weeks. CyNE790-labeled and ICG-labeled anti-EGFR antibodies (0.15 μg or 0.85 μg in PBS for both antibodies) were injected subcutaneously in the right and left rear flanks of the mice in a volume of 150 μL for each side. The animals were placed in an IVIS Spectrum imaging system (Caliper Life Sciences) immediately after antibody injection, and the fluorescence image was acquired using the 745 nm excitation and 820 nm emission filters. The results are shown in FIG. 13A.

In Vivo Detection of SCC-15 and MCF-7 Cells Using CyNE790-Anti-EGFR

SCC-15 and MCF-7 cell lines were each cultured in one 10-cm dish. At 50% confluency, the cells were incubated with 15 μg CyNE790-labelled anti-EGFR-$IgG_{2a}$ for 1 hour at room temperature. After incubation, cells were washed with media and PBS, scraped and resuspended in 150 μL PBS. CyNE790-anti-EGFR-$IgG_{2a}$-treated SCC-15 and MCF-7 cells were injected subcutaneously in the left rear flank of two separate mice (injection volume: 150 μL). Fifteen minutes after the injection, the animals were placed in an IVIS Spectrum imaging system (Caliper Life Sciences), and the fluorescence images were acquired using a 745-nm excitation filter and a 820-nm emission filter. The results are shown in FIG. 13B.

Example 3

Ultrasensitive NIR Raman Reporters for SERS-Based In Vivo Cancer Imaging

The synthesis and screening of an 80-member tricarbocyanine library led to the identification of a NIR SERS reporter, CyNAMLA-381, with 12-fold higher sensitivity than the standard 3,3'-diethylthiatricarbocyanine (DTTC).

A major bottleneck in SERS probe discovery is the development of highly sensitive Raman reporters. Most of the commonly used Raman signature molecules are active in the UV-visible range (e.g., crystal violet, malachite green isothiocyanate, rhodamine-6G, nile blue, 2-napthalenethiol, DRITC and DXRITC), and thus have a restricted potential for in vivo imaging. The adequacy of the NIR region for in vivo studies has increased interest in NIR SERS-active molecules. Although DTTC has been regarded as a standard in NIR SERS studies, it shows only a moderate Raman intensity. Since little is known about the correlation between the cyanine scaffold and its Raman intensity, a library of structurally diverse tricarbocyanines was designed to discover novel NIR SERS-active compounds that surpassed the sensitivity of DTTC.

The tricarbocyanine core is an accessible NIR structure whose central chlorine atom can be replaced with different nucleophiles. In order to prepare compounds that could be chemisorbed on gold nanoparticles (AuNPs), tricarbocyanine 21 was prepared and coupled to a disulfide-containing, lipoic acid spacer to afford the CyNAMLA scaffold.

The amine group of 21 was protected using di-tert-butyl dicarbonate then derivatized with 80 different primary amines (for structures, see FIGS. 14A-14D). After acetylation of the newly-introduced amine, the compounds were treated with a solution of TFA-DCM (1:9) to remove the tert-butylcarbamate protecting group. The deprotected amine was then coupled to lipoic acid to yield CyNAMLA derivatives with an average purity of 90% (for HPLC-determined purities, see Table 6). CyNAMLA compounds proved to be remarkably NIR-active with absorbance maximum wavelengths around 800 nm (Table 6).

TABLE 6

Characterization data of the CyNAMLA library.

| Plate code | Compound code | $M^+$ (calc.) | $M^+$ (exp.)[a] | tR | purity (%)[b] | λabs (max) | Raman intensity[c] |
|---|---|---|---|---|---|---|---|
| A2 | CyNAMLA-11 | 890.5 | 890.4 | 5.98 | 91 | 804 | 2374 |
| A3 | CyNAMLA-49 | 899.5 | 899.4 | 6.45 | 93 | 806 | 2271 |
| A4 | CyNAMLA-55 | 947.7 | 947.4 | 6.84 | 94 | 805 | 1125 |
| A5 | CyNAMLA-80 | 891.5 | 891.5 | 6.48 | 96 | 804 | 32082 |
| A6 | CyNAMLA-92 | 849.5 | 849.4 | 6.76 | 95 | 803 | 23452 |
| A7 | CyNAMLA-100 | 959.5 | 959.4 | 6.83 | 89 | 804 | 2312 |
| A8 | CyNAMLA-101 | 869.5 | 869.4 | 6.65 | 97 | 803 | 2102 |
| A9 | CyNAMLA-102 | 899.5 | 899.4 | 6.71 | 91 | 804 | 1602 |
| A10 | CyNAMLA-103 | 899.5 | 899.4 | 6.72 | 92 | 806 | 6424 |
| A11 | CyNAMLA-105 | 862.6 | 862.4 | 6.97 | 94 | 804 | 3878 |
| B2 | CyNAMLA-107 | 938.6 | 938.4 | 5.28 | 85 | 805 | 2397 |
| B3 | CyNAMLA-111 | 870.5 | 869.4 | 6.65 | 97 | 805 | 4021 |
| B4 | CyNAMLA-124 | 915.5 | 915.5 | 6.50 | 91 | 804 | 2201 |

TABLE 6-continued

Characterization data of the CyNAMLA library.

| Plate code | Compound code | M+ (calc.) | M+ (exp.)[a] | tR | purity (%)[b] | λabs (max) | Raman intensity[c] |
|---|---|---|---|---|---|---|---|
| B5 | CyNAMLA-131 | 897.5 | 897.5 | 6.30 | 71 | 806 | 4419 |
| B6 | CyNAMLA-164 | 832.5 | 847.6 | 6.40 | 74 | 803 | 4777 |
| B7 | CyNAMLA-177 | 916.1 | 823.3 | 6.53 | 97 | 802 | 9396 |
| B8 | CyNAMLA-180 | 833.5 | 833.4 | 6.52 | 91 | 804 | 8236 |
| B9 | CyNAMLA-181 | 915.6 | 915.5 | 6.53 | 80 | 804 | 2109 |
| B10 | CyNAMLA-184 | 929.6 | 929.4 | 6.60 | 70 | 803 | 24133 |
| B11 | CyNAMLA-185 | 835.5 | 835.4 | 6.80 | 71 | 805 | 4603 |
| C2 | CyNAMLA-193 | 935.7 | 935.5 | 7.14 | 88 | 803 | 1610 |
| C3 | CyNAMLA-201 | 897.5 | 897.5 | 6.70 | 72 | 804 | 6915 |
| C4 | CyNAMLA-218 | 873.5 | 873.3 | 6.55 | 95 | 804 | 1922 |
| C5 | CyNAMLA-220 | 889.4 | 873.3 | 6.59 | 97 | 805 | 6604 |
| C6 | CyNAMLA-221 | 890.5 | 889.3 | 6.64 | 96 | 804 | 26102 |
| C7 | CyNAMLA-230 | 877.6 | 877.5 | 7.02 | 94 | 804 | 4341 |
| C8 | CyNAMLA-262 | 915.5 | 915.5 | 6.45 | 95 | 805 | 27810 |
| C9 | CyNAMLA-266 | 929.5 | 929.5 | 6.50 | 75 | 806 | 3013 |
| C10 | CyNAMLA-272 | 876.5 | 876.5 | 5.08 | 93 | 805 | 1986 |
| C11 | CyNAMLA-274 | 865.5 | 865.5 | 6.38 | 96 | 806 | 6417 |
| D2 | CyNAMLA-275 | 897.5 | 897.5 | 6.97 | 80 | 804 | 1408 |
| D3 | CyNAMLA-277 | 863.5 | 863.4 | 6.97 | 94 | 804 | 2046 |
| D4 | CyNAMLA-282 | 878.5 | 878.5 | 5.36 | 90 | 805 | 1296 |
| D5 | CyNAMLA-295 | 793.5 | 793.5 | 6.29 | 96 | 804 | 1888 |
| D6 | CyNAMLA-319 | 915.5 | 915.5 | 6.28 | 94 | 805 | 2850 |
| D7 | CyNAMLA-329 | 935.5 | 933.5 | 6.70 | 75 | 804 | 4790 |
| D8 | CyNAMLA-335 | 883.5 | 883.5 | 6.67 | 89 | 805 | 8158 |
| D9 | CyNAMLA-336 | 945.5 | 945.5 | 6.46 | 88 | 805 | 2548 |
| D10 | CyNAMLA-341 | 933.4 | 933.4 | 6.34 | 70 | 804 | 1071 |
| D11 | CyNAMLA-346 | 927.5[d] | 927.5 | 6.43 | 87 | 805 | 2940 |
| E2 | CyNAMLA-356 | 945.5 | 945.5 | 6.24 | 97 | 806 | 2333 |
| E3 | CyNAMLA-358 | 915.5 | 915.5 | 6.44 | 98 | 804 | 1121 |
| E4 | CyNAMLA-359 | 914.5 | 914.5 | 6.48 | 97 | 805 | 2068 |
| E5 | CyNAMLA-364 | 889.4 | 889.4 | 6.58 | 96 | 804 | 3561 |
| E6 | CyNAMLA-373 | 821.5 | 821.5 | 6.57 | 94 | 804 | 2487 |
| E7 | CyNAMLA-374 | 855.5 | 855.5 | 6.59 | 97 | 803 | 9636 |
| E8 | CyNAMLA-375 | 873.5 | 873.5 | 6.52 | 97 | 804 | 1976 |
| E9 | CyNAMLA-381 | 885.5 | 885.5 | 6.50 | 98 | 804 | 38210 |
| E10 | CyNAMLA-382 | 861.5 | 861.5 | 6.85 | 99 | 804 | 7947 |
| E11 | CyNAMLA-387 | 885.5 | 885.5 | 6.50 | 97 | 804 | 3910 |
| F2 | CyNAMLA-388 | 885.5 | 885.5 | 6.57 | 96 | 805 | 1620 |
| F3 | CyNAMLA-395 | 899.5 | 899.5 | 6.58 | 96 | 805 | 1876 |
| F4 | CyNAMLA-396 | 869.5 | 869.5 | 6.65 | 93 | 806 | 6521 |
| F5 | CyNAMLA-398 | 869.6 | 869.6 | 6.65 | 94 | 805 | 2629 |
| F6 | CyNAMLA-401 | 856.5 | 856.5 | 5.97 | 91 | 804 | 2920 |
| F7 | CyNAMLA-403 | 889.4 | 889.4 | 6.58 | 98 | 804 | 3417 |
| F8 | CyNAMLA-405 | 887.4 | 887.4 | 6.67 | 92 | 805 | 12149 |
| F9 | CyNAMLA-407 | 905.4 | 905.4 | 7.53 | 94 | 806 | 3000 |
| F10 | CyNAMLA-414 | 904.6 | 904.6 | 6.62 | 88 | 806 | 5267 |
| F11 | CyNAMLA-419 | 835.5 | 835.5 | 6.54 | 83 | 804 | 9354 |
| G2 | CyNAMLA-427 | 850.4 | 850.4 | 6.71 | 80 | 805 | 1735 |
| G3 | CyNAMLA-439 | 849.6 | 849.6 | 6.42 | 81 | 805 | 3589 |
| G4 | CyNAMLA-442 | 835.5 | 835.5 | 6.32 | 75 | 803 | 1989 |
| G5 | CyNAMLA-443 | 833.6 | 807.5 | 6.75 | 71 | 806 | 1833 |
| G6 | CyNAMLA-446 | 845.5 | 845.5 | 6.38 | 80 | 804 | 8301 |
| G7 | CyNAMLA-452 | 933.4 | 933.4 | 6.62 | 71 | 805 | 24271 |
| G8 | CyNAMLA-477 | 888.0 | 887.9 | 6.64 | 97 | 804 | 9679 |
| G9 | CyNAMLA-478 | 883.5 | 883.4 | 6.74 | 92 | 805 | 35116 |
| G10 | CyNAMLA-480 | 903.5 | 903.5 | 6.62 | 89 | 805 | 10253 |
| G11 | CyNAMLA-531 | 923.4 | 923.2 | 6.75 | 88 | 805 | 5272 |
| H2 | CyNAMLA-548 | 945.5 | 945.4 | 6.72 | 70 | 803 | 10165 |
| H3 | CyNAMLA-565 | 923.4 | 923.3 | 6.86 | 92 | 805 | 14019 |
| H4 | CyNAMLA-567 | 919.7 | 919.5 | 6.84 | 90 | 802 | 9879 |
| H5 | CyNAMLA-572 | 947.5 | 947.4 | 6.63 | 94 | 804 | 2718 |
| H6 | CyNAMLA-574 | 835.5 | 835.5 | 6.82 | 93 | 804 | 1763 |
| H7 | CyNAMLA-599 | 945.6 | 945.5 | 6.45 | 85 | 804 | 11616 |
| H8 | CyNAMLA-611 | 876.6 | 876.5 | 6.54 | 81 | 804 | 18833 |
| H9 | CyNAMLA-621 | 951.4 | 951.3 | 6.73 | 75 | 804 | 2050 |
| H10 | CyNAMLA-677 | 903.5 | 903.3 | 6.43 | 83 | 805 | 2455 |
| H11 | CyNAMLA-686 | 937.5 | 937.4 | 6.78 | 72 | 806 | 8146 |

[a] ESI-MS m/z corresponding to [M + H+] values.
[b] Purities were determined by integration of the UV absorbance signal at 365 nm.
[c] SERS spectra were obtained from excitation at 785 nm with a laser power of 60 mW.
[d] The main product corresponded to the double acetylated derivative.

Figure 15:
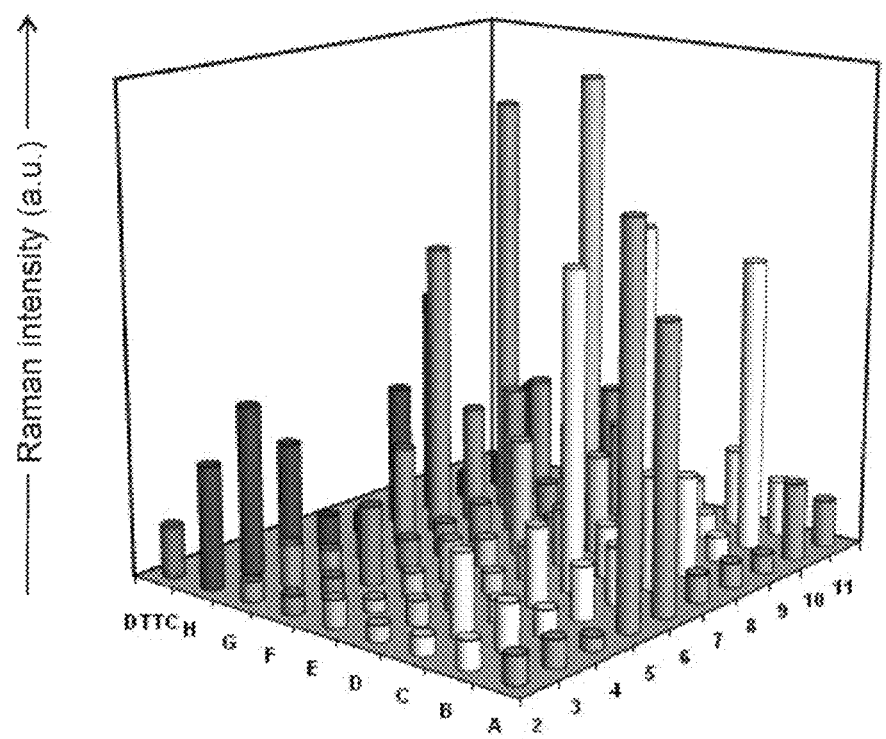
FIG. 15 is a graph of the comparative surface-enhanced Raman spectroscopy (SERS) intensities of members of the CyNAMLA library measured with an excitation wavelength of 785 nm and a laser power of 60 mW in a compact Raman scanner.

The CyNAMLA compounds were adsorbed onto AuNPs having a diameter of approximately 60 nm, and the SERS properties of the resulting CyNAMLA-functionalized AuNPs were evaluated using a compact Raman scanner. Among metal nanoparticles, AuNPs are particularly suitable for in vivo applications due to their low toxicity, adaptability to bioconjugation, and reproducible signal intensity and quantification. FIG. 15 shows the results of this primary screen, which revealed that the SERS intensities of CyNAMLA compounds varied significantly across the library. This variance suggested that the SERS intensities of the CyNAMLA-functionalized AuNPs was correlated with amine structure. Six derivatives containing mostly aromatic amines (CyNAMLA-80, 92, 221, 262, 381 and 478, represented in FIG. 15 as A5, A6, C6, C8, E9 and G9, respectively) exhibited SERS intensities that exceeded the signal of DTTC.

Figure 16:
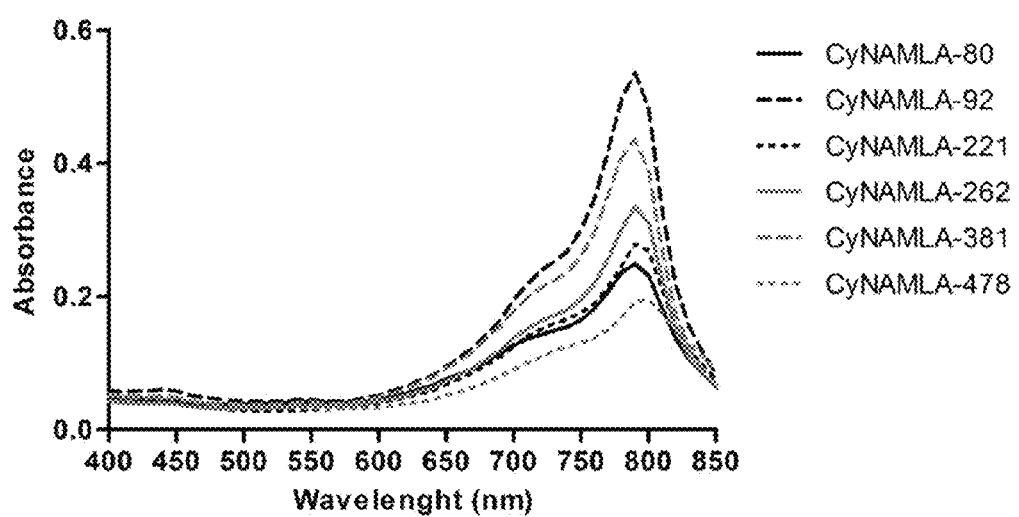
FIG. 16 is an absorbance spectrum of 10-μM solutions of six CyNAMLA derivatives in PBS (20 mM, pH 7.4), and shows the absorbance as a function of wavelength (nm).

FIG. 16 is an absorbance spectrum of 10-μM solutions of the six most-promising CyNAMLA derivatives in PBS (20 mM, pH 7.4), and shows the absorbance as a function of wavelength. The absorption maxima of all six CyNAMLA compounds were around 780 nm, which matches well with the NIR laser beam (785 nm) used for the SERS measurements. This is notable because SERS intensities are enhanced when the absorption maxima of the SERS-active molecule match the excitation wavelength of the laser source.

Figure 17:
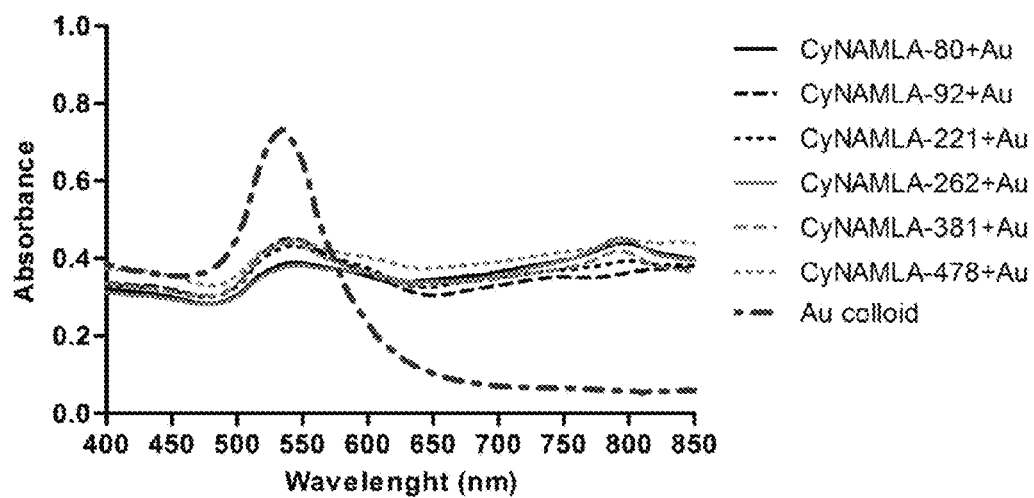
FIG. 17 is a surface plasmon absorption spectrum of gold colloids derivatized with CyNAMLA, and shows the absorbance as a function of wavelength (nm).

FIG. 17 is a surface plasmon absorption spectrum of gold colloids derivatized with the same six CyNAMLA compounds, and shows the absorbance as a function of wavelength. The absorption band of the CyNAMLA-functionalized AuNPs occurring at approximately 540 nm did not have a significant shoulder, indicating that little or no aggregation of the AuNPs had occurred as a result of functionalization of the CyNAMLA compounds.

The encapsulation of SERS-active nanoparticles is a crucial step because it can prevent their aggregation and the desorption of Raman signature molecules from the NPs, and it can be used to introduce functional groups on their surface for bioconjugation. The six selected CyNAMLA-AuNPs of FIGS. 16 and 17 were modified with BSA and glutaraldehyde so that amine-containing molecules (e.g., antibodies) could be attached to the resulting cross-linked organic layer on the surface.

Figure 18:
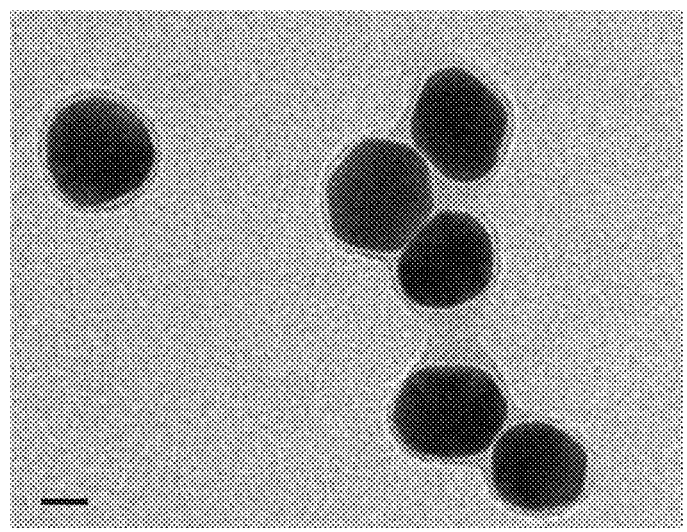
FIG. 18 is a transmission electron microscopy (TEM) image of BSA-encapsulated CyNAMLA-381 nanotags.

FIG. 18 is a transmission electron microscopy (TEM) image of BSA-encapsulated CyNAMLA-381 nanotags and confirms that the AuNPs increased in size to approximately 65-70 nm in diameter after BSA encapsulation. An image of a gel taken after SDS-PAGE of free scFv-anti-HER2 antibody and scFv-anti-HER2-conjugated, BSA-encapsulated CyNAMLA-381 SERS nanotags showed that the antibody-AuNP conjugate ran slightly more slowly than the free antibody, suggesting the antibody-AuNP conjugate was larger than the unlabeled scFv. Taken together, these experiments verify the success of the encapsulation and functionalization of the AuNPs.

Figure 19:
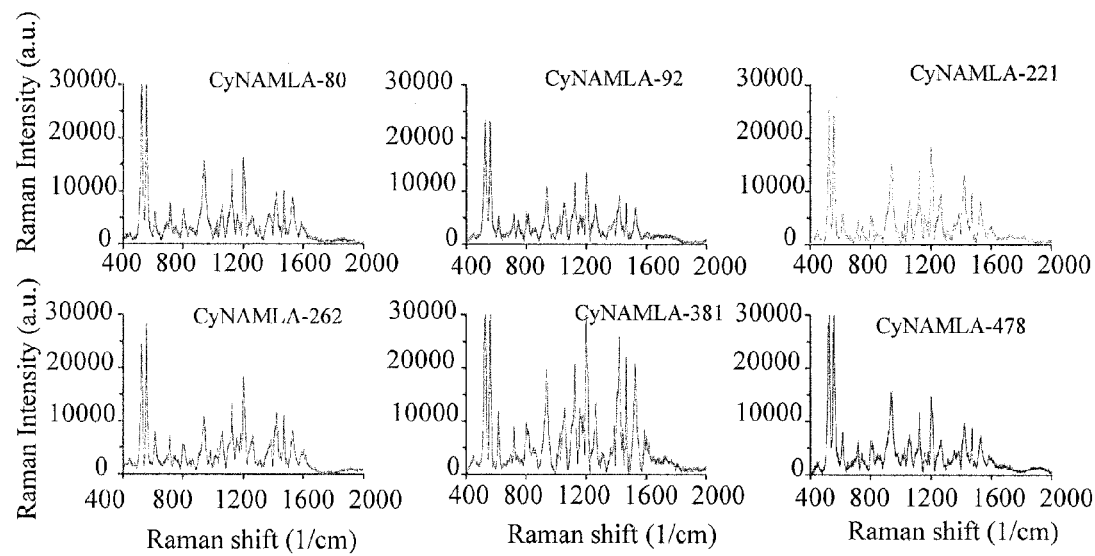
FIG. 19 is a SERS spectra of BSA-encapsulated nanotags functionalized with CyNAMLA-80, CyNAMLA-92, CyNAMLA-221, CyNAMLA-262, CyNAMLA-381 and CyNAMLA-478.
Figure 20:
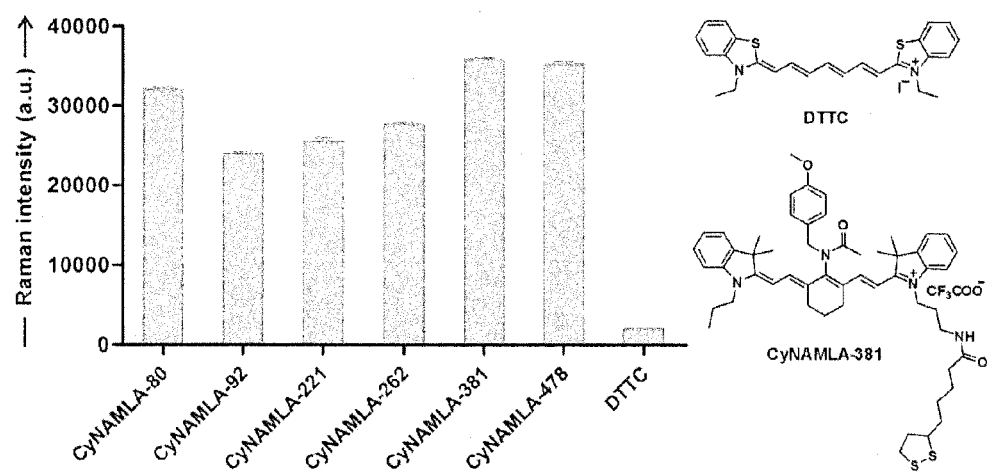
FIG. 20 is a graph of the SERS intensities of selected BSA-encapsulated CyNAMLA-gold nanoparticles measured in a Renishaw Raman microscope ($\lambda_{excitation}$=785 nm), and shows the chemical structures of DTTC and CyNAMLA-381.

FIG. 19 is a SERS spectra of BSA-encapsulated nanotags functionalized with CyNAMLA-80, CyNAMLA-92, CyNAMLA-221, CyNAMLA-262, CyNAMLA-381 and CyNAMLA-478 and FIG. 20 shows the relative intensities of the signals depicted in FIG. 19. CyNAMLA-381 exhibited the most intense signal, which was about 12-fold higher than the signal exhibited by DTTC.

Figure 21A:
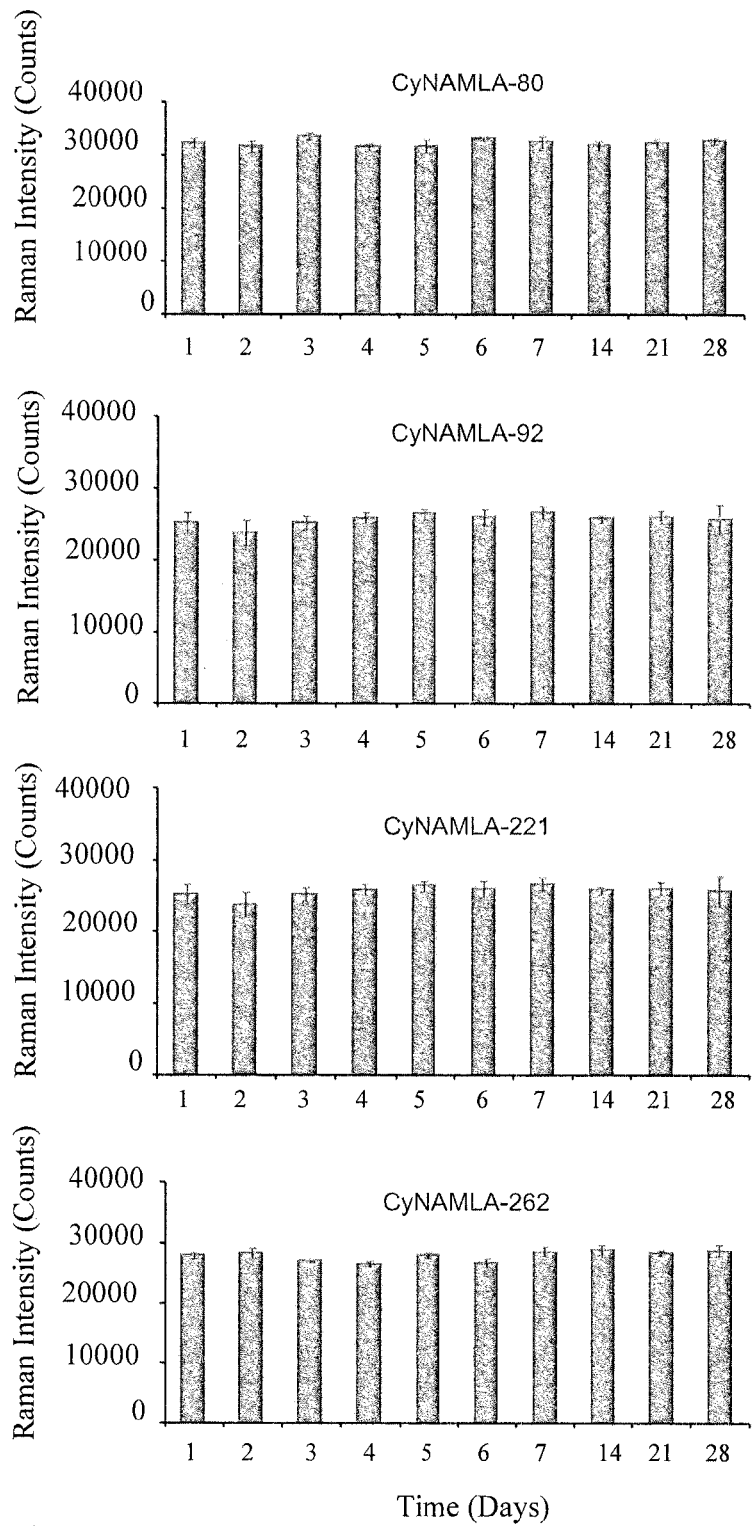
FIG. 21A is a graph of the SERS intensities of CyNAMLA-80, CyNAMLA-92, CyNAMLA-221 and CyNAMLA-262 nanotags as a function of time (days).
Figure 21B:
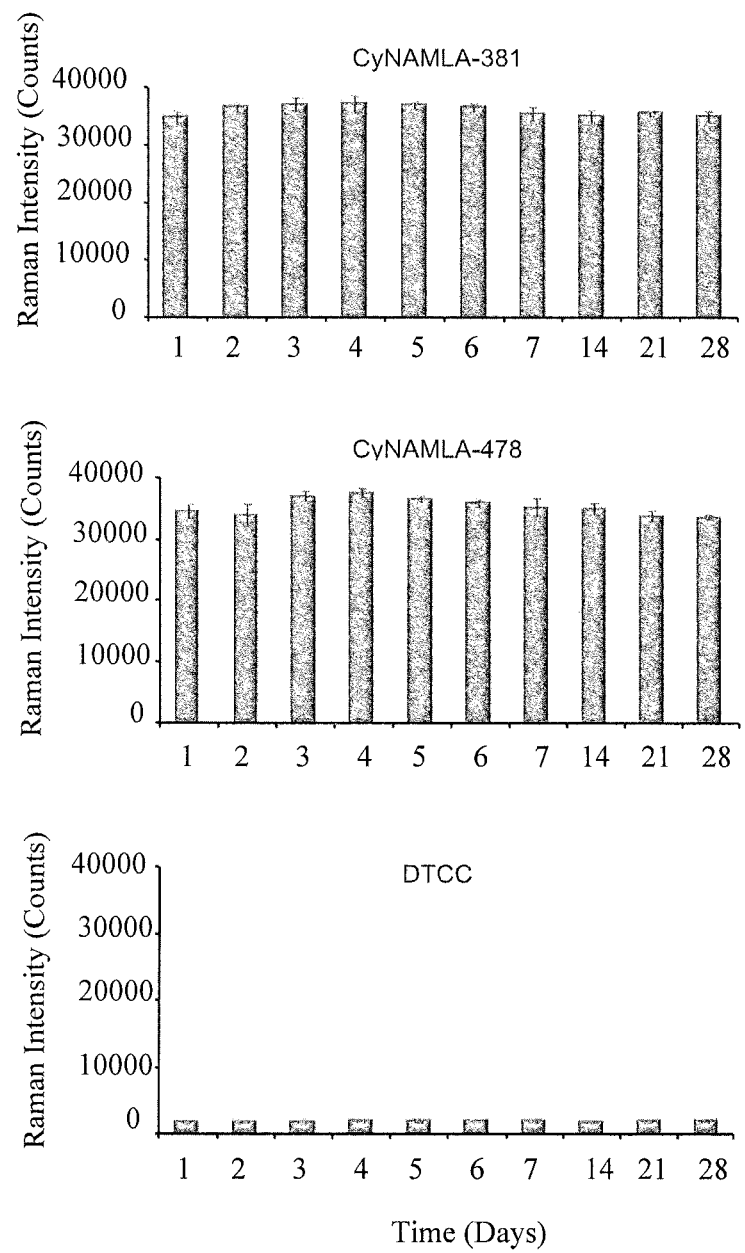
FIG. 21B is a graph of the SERS intensities of CyNAMLA-381, CyNAMLA-478 and DTTC nanotags as a function of time (days).

The stability of the SERS intensities of the BSA-encapsulated CyNAMLA-AuNPs over a time period of 1 month was also monitored (FIGS. 21A and 21B). The nanotags did not show any significant aggregation under ambient conditions and exhibited consistent SERS intensities over time with a very low relative standard deviation (2 to 3%).

The HER2 signaling pathway plays an important role in cell proliferation, and is upregulated in most breast cancers. To prepare SERS nanotags that could selectively detect cancer cells expressing HER2 receptors, CyNAMLA-381-AuNPs were conjugated to two HER2-recognition motifs: a full-length anti-HER2 monoclonal antibody (170 kDa) and a truncated antibody, scFv anti-HER2 (26 kDa).

Figure 22:
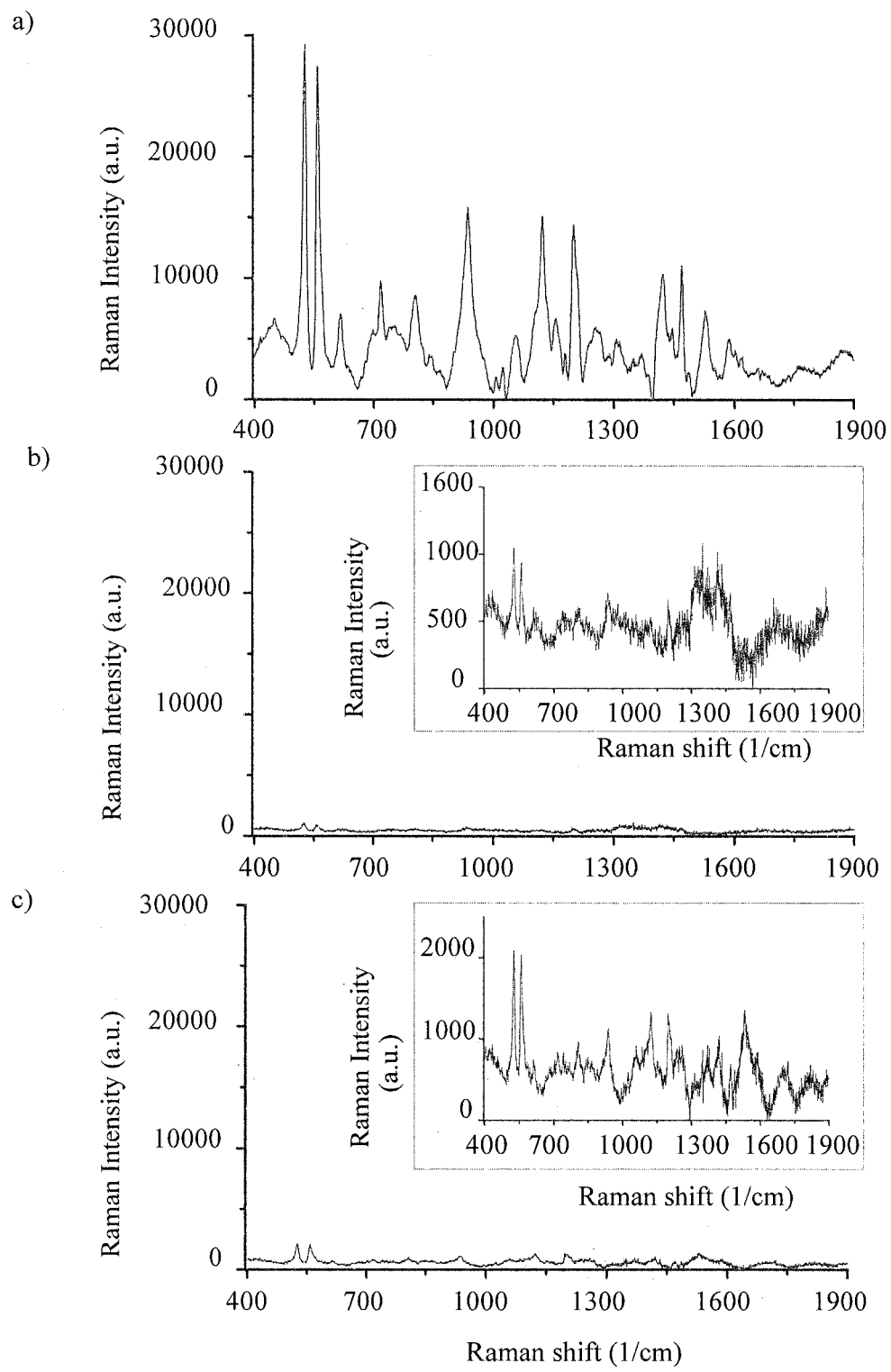
FIG. 22 is a SERS signal of scFv anti-HER2-conjugated SERS nanotags upon incubation with a) HER-2-positive SKBR-3 cells (top spectrum); b) HER2-negative MDA-MB231 cells (middle spectrum); and c) SKBR-3 cells and free scFv anti-HER2, using an excitation wavelength of 785 nm and a laser power of 60 mW (insets contain zoom spectra).

The in vitro specificity of the antibody-functionalized CyNAMLA-381-AuNPs in SKBR-3 (HER2-positive) and MDA-MB231 (HER2-negative) cancer cells was examined. Upon incubation of SKBR-3 cells with antibody-conjugated CyNAMLA-381-AuNPs, strong SERS signals were observed, while negligible signals were detected after incubating the same NPs with MDA-MB231 cells (FIG. 22). The target specificity of CyNAMLA-381-AuNPs in SKBR-3 cells was confirmed using competition assays between antibody-conjugated nanotags and free scFv anti-HER2. A 10- to 15-fold decrease of the SERS signals in the presence of the competing anti-HER2 antibody was observed (FIG. 22). Interestingly, the signal intensities obtained with scFv-conjugated nanotags were 1.5 times stronger than those obtained with full-length anti-HER2. This data suggests that biosensors employing truncated antibodies, such as scFv, have lower detection limits and comparable specificities to their full-length counterparts. Furthermore, the smaller size of scFv can significantly reduce the interstitial tumor pressure that impedes intratumoral distribution when using larger recognition motifs.

Figure 23A:
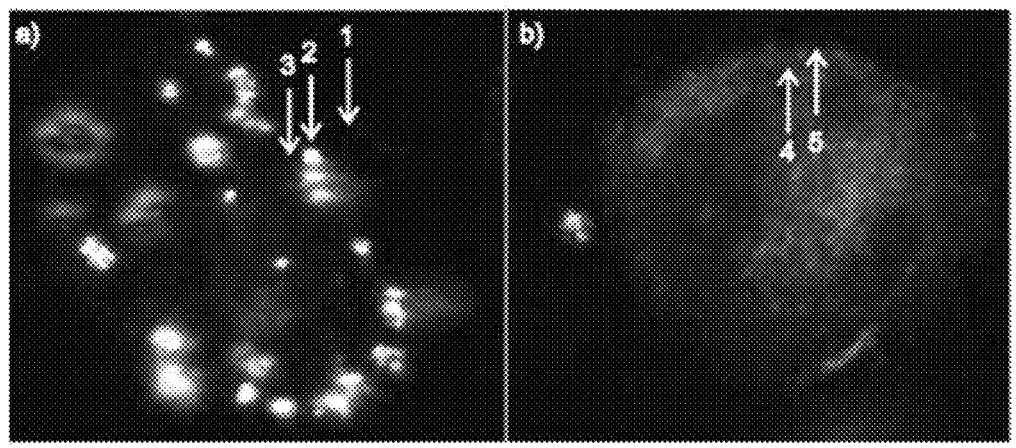
FIG. 23A is a dark-field reflective microscopy image of SKBR-3 cells (left) and of MDA-MB231 cells (right) after treatment with scFv anti-HER2-conjugated SERS nanotags.

The recognition properties of antibody-functionalized CyNAMLA-381-AuNPs was analyzed by reflective mode dark-field microscopy (FIG. 23A). The reflective mode dark-field images of SKBR-3 cells that were incubated with scFv-conjugated CyNAMLA-381-SERS nanotags displayed a number of bright spots on the cell surface due to the recognition of HER2, while the same experimental conditions in HER-2 negative cells (MDA-MB231) showed a negligible scattering. The corresponding SERS spectra (FIG. 23B) showed intense SERS signals from the particles located on the cell surface of the HER2-positive cells (points 2 and 3 in FIG. 23A), and no SERS signals in other regions of the SKBR-3 cells (point 1 in FIG. 23A) or in MDA-MB231 cells (points 4 and 5 in FIG. 23A).

Figure 24A:
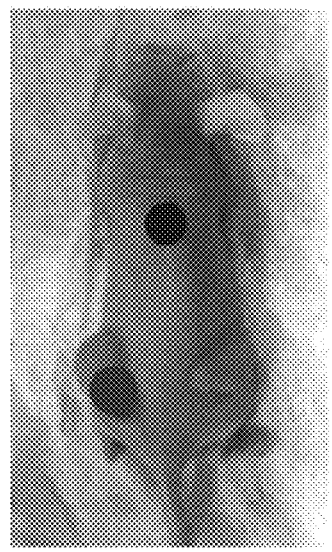
FIG. 24A is an image of a mouse bearing a xenograft generated from SKBR-3 cells (left flank, marked with a dot) and injected with scFv anti-HER2-conjugated CyNAMLA-381 nanotags (center of back, marked with a dot, indicates a non-tumorigenic area).
Figure 24B:
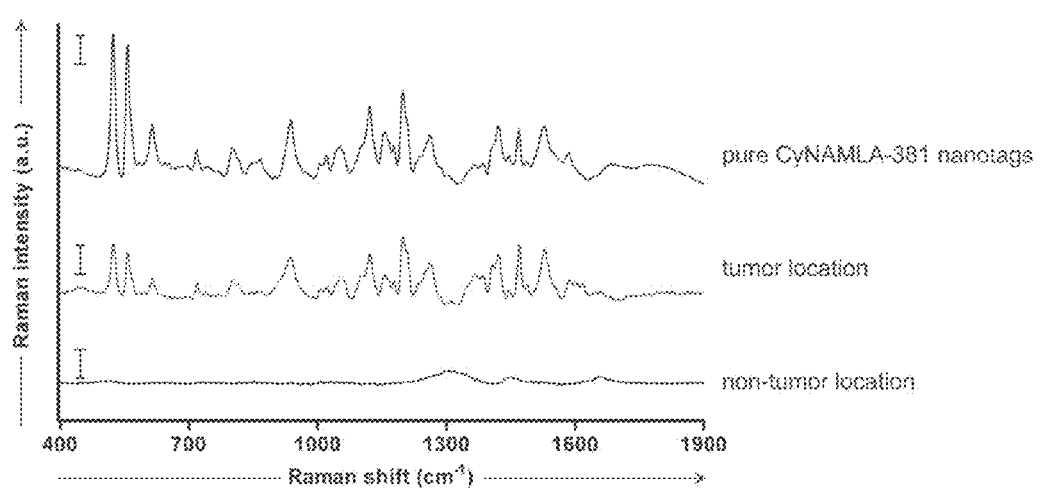
FIG. 24B is a SERS spectrum of pure nanotags (top signal), of the tumor location marked in FIG. 24A (middle signal) and of the non-tumorigenic area marked in FIG. 24A (bottom signal) (scale bar=5,000 cps).
Figure 25A:
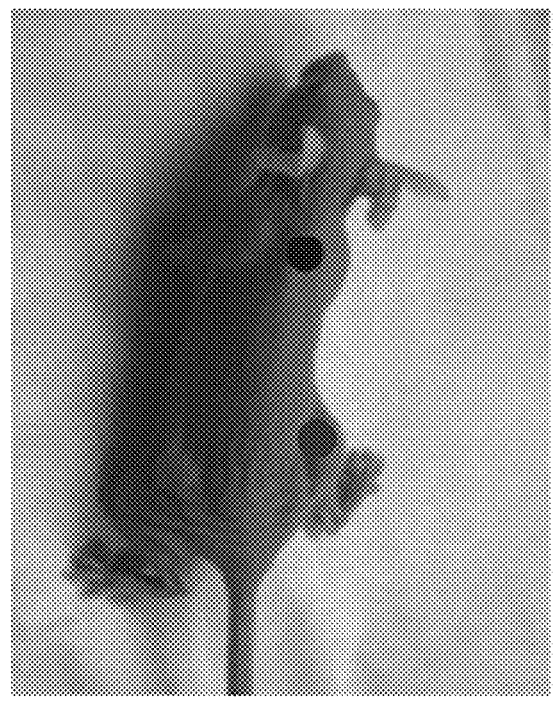
FIG. 25A is an image of a mouse bearing a xenograft generated from HER2-negative tumors (right flank, marked with a dot) and injected with scFv-conjugated CyNAMLA-381 nanotags (center of back, marked with a dot, indicates a non-tumorigenic area.
Figure 25B:
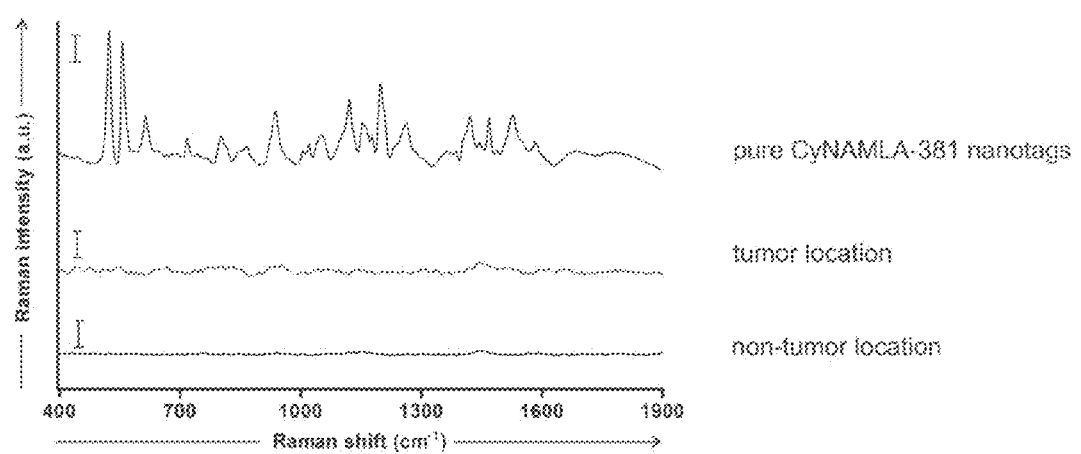
FIG. 25B is a SERS spectrum of pure nanotags (top signal), of the tumor location marked with a dot in FIG. 25A (middle signal) and of the non-tumorigenic location marked with a dot in FIG. 25A (bottom signal) (scale bar=5,000 cps).

Finally, in order to validate the optical detection by scFv-conjugated CyNAMLA-381-AuNPs in vivo, nude mice bearing xenografts generated from SKBR-3 cells were injected with the functionalized nanoparticles. Five hours after tail vein injection, the SERS spectra of the tumor site was measured using a NIR laser beam. Whereas the signal of the tumor site perfectly resembled the SERS spectra of the pure nanotag, no SERS signal was detected from other anatomical locations (e.g., liver, heart) (FIGS. 24A and 24B). Furthermore, no significant SERS signal was detected after injecting the nanotags in xenograft models prepared with HER2-negative cancer cells (FIGS. 25A and 25B). These results indicate that the scFv-conjugated CyNAMLA-381-AuNPs were able to specifically detect HER2-positive tumors in vivo.

In summary, a lipoic acid-containing NIR-active tricarbocyanine library was prepared, and the SERS properties of the CyNAMLA derivatives were screened after chemisorption onto AuNPs. CyNAMLA compounds exhibited strong SERS intensities, and CyNAMLA-381 was identified as a highly sensitive NIR SERS reporter molecule with excellent signal stability and 12-fold higher fluorescence intensity than DTTC. Ultrasensitive SERS probes for in vivo cancer imaging were also prepared by conjugating CyNAMLA-381-AuNPs to scFv anti-HER2 antibodies. These nanotags displayed very good SERS intensity and selectivity towards HER2-positive cancer cells under both Raman and dark-field microscopes. Furthermore, the antibody-functionalized CyNAMLA-381-AuNPs were used in vivo to detect HER2 in HER2-positive and negative xenograft models. The low detection limit, high sensitivity and tumor specificity of scFv-conjugated CyNAMLA-381-AuNPs proves their excellent potential as non-invasive diagnostic tools.

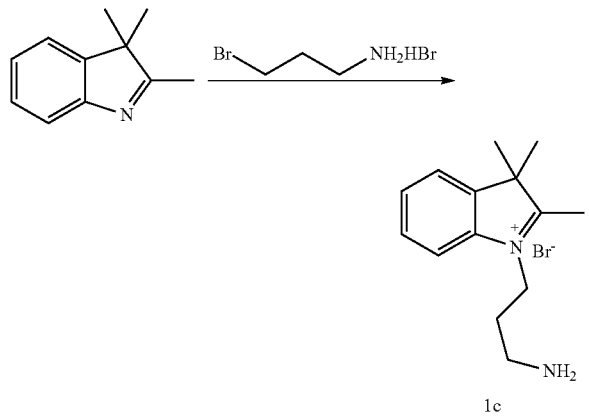

3-Bromopropylamine hydrobromide (2.7 g, 12.5 mmol, 1 equiv) was added to a sealed tube containing 2,3,3-trimethyl-3H-indole (2.0 mL, 12.5 mmol, 1 equiv) under $N_2$ atmosphere, and was gently heated at 110° C. in an oil bath. The mixture was kept at 120° C. for 10 hours with stirring. After the reaction was completed, the mixture was cooled to room temperature to form a solid cake that was washed with $Et_2O$ and a chloroform-$Et_2O$ (1:1) solution. The resulting solid was then dried under high vacuum to obtain 1c as a white solid (4.3 g, yield 85%).

$^1$H-NMR (300 MHz, DMSO-d6): 1.55 (s, 6H), 2.16-2.21 (m, 2H), 2.50 (s, 3H), 3.05-3.07 (m, 2H), 4.60 (t, 2H, J=7.5 Hz), 7.61-8.08 (m, 4H). tR: 2.10 min, ESI-MS m/z ($C_{14}H_{22}BrN_2^+$) calc: 217.2. found: 217.1.

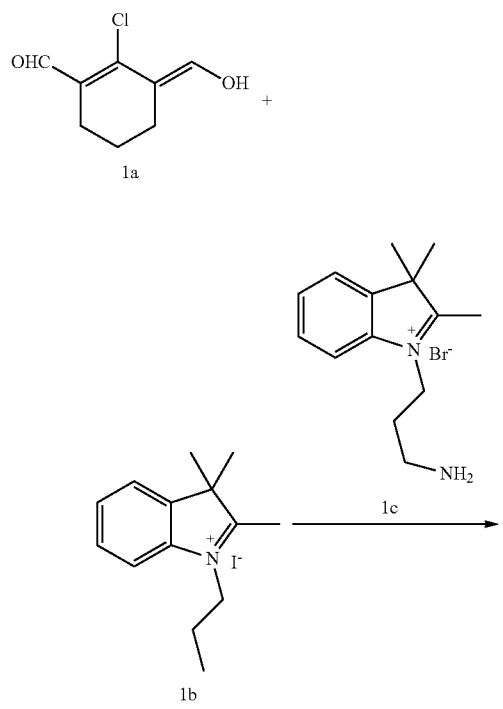

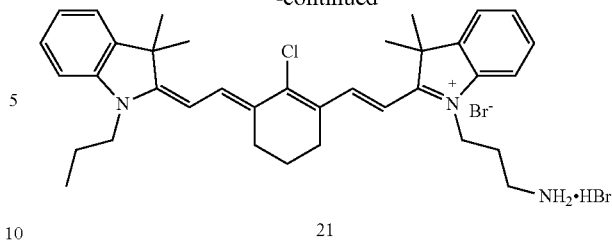

Under $N_2$ atmosphere, 1a (1.0 g, 6 mmol, 1 equiv) and 1b (2.3 g, 6 mmol, 1 equiv) were dissolved in 50 mL of butanol-benzene (7:3) and refluxed for 2 hours at 110° C. The mixture was then allowed to cool to room temperature and 1c (2.0 g, 6 mmol, 1 equiv) was added as a solution in butanol-benzene (7:3). The reaction mixture was then refluxed for 12 hours at 120° C. in a Dean-Stark condenser. The solvent was evaporated and the resulting green solid mixture was washed with $Et_2O$ and purified by normal phase chromatography (elution with DCM-MeOH, 95:5) to obtain 21 as a green solid (3.0 g, yield 78%).

$^1$H-NMR (500 MHz, $CDCl_3$): 1.02 (t, 3H, J=7.5 Hz), 1.67 (s, 6H), 1.69 (s, 6H), 1.82-1.86 (m, 2H), 1.97 (t, 2H, J=6.6 Hz), 2.37 (t, 2H, J=7.2 Hz), 2.55 (m, 2H), 2.99 (t, 2H, J=7.2 Hz), 3.57 (t, 2H, J=6.6 Hz), 3.92 (t, 2H, J=6.6 Hz), 4.76 (t, 2H, J=6.6 Hz), 5.92 (d, 1H, J=13.5 Hz), 6.62 (d, 1H, J=14.4 Hz), 7.00-7.72 (m, 8H), 7.33 (d, 1H, J=13.5 Hz), 7.41 (d, 1H, J=14.4 Hz).

tR: 5.37 min, ESI (HRMS) m/z ($C_{36}H_{46}BrClN_3^+$) calc: 554.3297. found: 554.3316.

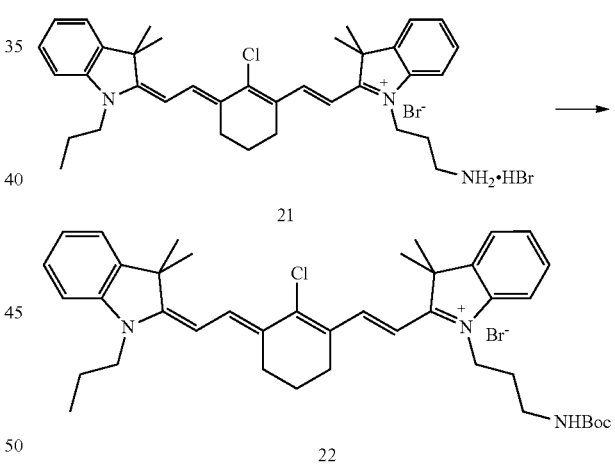

21 (2.5 g, 4.5 mmol, 1 equiv) was dissolved in $CHCl_3$, and DIEA (2.9 g, 22.5 mmol, 5 equiv) and di-tert-butyl dicarbonate (1.5 g, 6.8 mmol, 1.5 equiv) were added. The resulting reaction mixture was refluxed for 4 hours. The mixture was washed with $H_2O$ (2×100 mL) and dilute HCl, and the combined organic layers were evaporated and purified by normal-phase chromatography (elution with DCM-MeOH, 95:5) to obtain 22 as a green solid (3.0 g, 91%).

$^1$H-NMR (300 MHz, $CDCl_3$): 1.06 (t, 3H, J=7.2 Hz), 1.43 (s, 9H), 1.70 (s, 12H), 1.86-1.90 (m, 2H), 1.97 (t, 2H, J=6.6 Hz), 2.66 (t, 2H, J=7.2 Hz), 2.81 (t, 2H, J=6.5 Hz), (2.76 (t, 2H, J=7.2 Hz), 3.38 (t, 2H, J=6.6 Hz), 4.00 (t, 2H, J=6.5 Hz), 4.42 (t, 2H, J=7.0 Hz), 6.01 (d, 1H, J=13.5 Hz), 6.46 (d, 1H, J=14.1 Hz), 6.46-7.35 (m, 8H), 8.23 (d, 1H, J=13.0 Hz), 8.39 (d, 1H, J=15.0 Hz).

tR: 6.51 min, ESI (HRMS) m/z ($C_{41}H_{53}ClN_3O_2^+$) calc: 654.3302. found: 654.3846.

Synthesis of Lipoic Acid Nitrophenol Resin

Aminomethyl nitrophenol polystyrene resin was prepared according to reported procedures. See J. W. Lee, Y. Q. Louie, D. P. Walsh and Y. T. Chang, *J. Comb. Chem.* 2003, 5, 330-335. The nitrophenol resin (2 g, 2.9 mmol, 1 equiv) was swollen in 10 mL of DMF, and lipoic acid (2 g, 10 mmol, 3.3 equiv), N,N-diisopropylcarbodiimide (1.2 mL, 12 mmol, 4 equiv) and a catalytic amount of DMAP (20 mg) were added to the resin, which was continuously shaken for 24 hours at room temperature. Subsequently, the resin was washed with DCM (10×25 mL) and dried under vacuum until use.

General Procedure for the Synthesis of the CyNAMLA Library

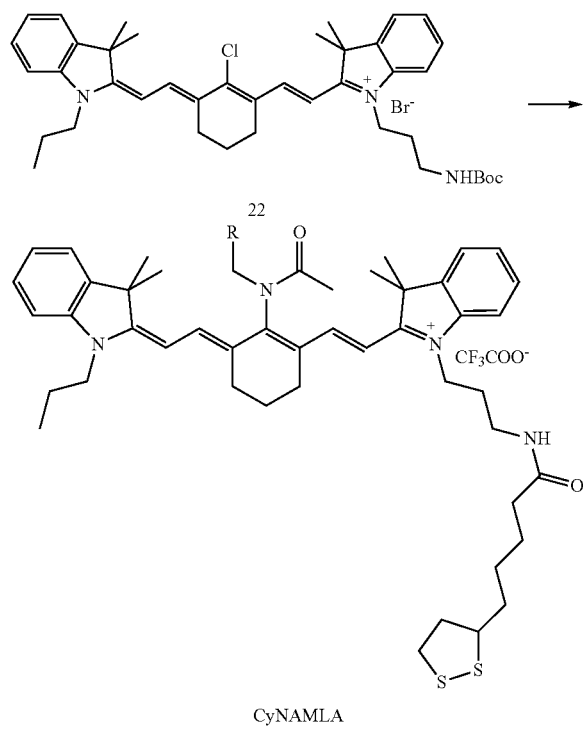

CyNAMLA 22 (60 mg, 92 µmol, 1 equiv) and a primary amine building block from FIGS. 14A-14D (368 µmol, 4 equiv) were dissolved in ACN, and DIEA (26.8 µL, 184 µmol, 2 equiv) was added. The reaction mixture was heated at 80° C. for 0.5-3 hours, depending on the reactivity of the amine. The resulting blue mixtures were neutralized with 0.1 N HCl, and dried under vacuum. The blue mixture was then dissolved in DCM and treated with DIEA (268 µL, 1.84 mmol, 20 equiv) and acetyl chloride (460 µmol, 5 equiv) at 0° C. for 10 minutes. The final green mixture was washed with 0.1 N HCl to remove excess DIEA, concentrated under vacuum, and purified by normal-phase chromatography (DCM-MeOH ranging from 100:0 to 95:5). Subsequently, the compounds were treated with TFA-DCM (1:9) at room temperature overnight, washed with an aqueous solution of $NaHCO_3$ and dried under vacuum. A 1-µmol aliquot of all 80 compounds was dissolved in 1 mL DCM:ACN (2:1) and treated with lipoic acid nitrophenol resin (30 mg, 10 µmol, 10 equiv) overnight at room temperature. The resulting mixtures were purified with short, silica-based columns to furnish 80 CyNAMLA compounds, which were characterized by HPLC-MS (see Table 6).

CyNAMLA-80, 92, 221, 262, 381 and 478 were further characterized by $^1$H-NMR and HRMS.

CyNAMLA-80 (12 mg, yield 10%). $^1$H-NMR (500 MHz, $CDCl_3$): 1.07 (t, 3H, J=7.0 Hz), 1.25 (s, 6H), 1.56 (s, 6H), 1.71-1.75 (m, 4H), 1.83-1.92 (m, 2H), 1.94 (s, 3H), 2.05-2.08 (m, 2H), 2.44-2.49 (m, 3H), 2.61-2.64 (m, 4H), 3.08-3.11 (m, 4H), 3.15 (t, 2H, J=6.5 Hz), 3.45 (t, 2H, J=5.0 Hz), 3.57-3.61 (m, 2H), 3.85 (t, 2H, J=7.2 Hz), 4.51 (s, 2H), 4.59 (t, 2H, J=6.2 Hz), 5.26 (d, 1H, J=13 Hz), 5.83 (d, 1H, J=13.5 Hz), 6.54 (d, 1H, J=7.5 Hz), 6.67 (d, 1H, J=7.0 Hz), 7.13-7.98 (m, 11H).

tR: 6.48 min, ESI (HRMS) m/z ($C_{53}H_{65}F_2N_4O_2S_2^+$), calc: 891.4512. found: 891.4525.

CyNAMLA-221 (15 mg, yield 11%). $^1$H-NMR (500 MHz, $CDCl_3$): 1.06 (t, 3H, J=7.0 Hz), 1.44 (s, 6H), 1.51 (s, 6H), 1.68-1.71 (m, 4H), 1.83-1.87 (m, 2H), 1.90 (s, 3H), 2.05-2.08 (m, 2H), 2.42-2.49 (m, 3H), 2.66-2.71 (m, 4H), 3.08-3.13 (m, 4H), 3.16 (t, 2H, J=5.0 Hz), 3.45 (t, 2H, J=5.0 Hz), 3.59-3.61 (m, 2H), 3.85 (t, 2H, J=7.5 Hz), 4.51 (t, 2H, J=6.2 Hz), 4.56 (s, 2H), 4.91 (d, 11-1, J=14.0 Hz), 5.85 (d, 11-1, J=13.0 Hz), 6.62 (d, 111, J=7.5 Hz), 6.94 (d, 1H, J=7.0 Hz), 7.13-7.71 (m, 12H).

tR: 6.64 min, ESI (HRMS) m/z ($C_{53}H_{66}ClN_4O_2S_2^+$), calc: 889.4310. found: 889.4334.

CyNAMLA-262 (14 mg, yield 11%). $^1$H-NMR (500 MHz, $CDCl_3$): 1.06 (t, 3H, J=7.0 Hz), 1.25 (s, 6H), 1.58 (s, 6H), 1.68-1.74 (m, 4H), 1.84-1.88 (m, 2H), 1.92 (s, 3H), 1.99-2.04 (m, 2H), 2.39-2.47 (m, 3H), 2.56-2.59 (m, 4H), 3.07-3.12 (m, 4H), 3.38 (t, 2H, J=6.5 Hz), 3.47 (t, 2H, J=5.0 Hz), 3.56-3.59 (m, 2H), 3.66 (s, 3H), 3.72 (s, 3H), 3.85 (t, 2H, J=7.2 Hz), 4.36 (s, 2H), 4.55 (t, 2H, J=6.2 Hz), 5.86 (d, 1H, J=13.0 Hz), 5.97 (d, 1H, J=13.5 Hz), 6.44 (d, 1H, J=7.5 Hz), 6.58 (d, 1H, J=7.0 Hz), 7.14-8.03 (m, 11H).

tR: 6.45 min, ESI (HRMS) m/z ($C_{55}H_{71}N_4O_4S_2^+$), calc: 915.4911. found: 891.4901.

CyNAMLA-381 (20 mg, yield 15%). $^1$H-NMR (500 MHz, $CDCl_3$): 1.05 (t, 3H, J=7.5 Hz), 1.53 (s, 6H), 1.59 (s, 6H), 1.67-1.74 (m, 4H), 1.83-1.87 (m, 2H), 1.88 (s, 3H), 2.02-2.08 (m, 2H), 2.39-2.46 (m, 3H), 2.69-2.71 (m, 4H), 3.06-3.11 (m, 4H), 3.12 (t, 2H, J=5.0 Hz), 3.46 (t, 2H, J=5.0 Hz), 3.64 (s, 3H), 3.59-3.61 (m, 2H), 3.84 (t, 2H, J=7.5 Hz), 4.59 (t, 2H, J=6.2 Hz), 4.35 (s, 2H), 5.01 (d, 1H, J=14.0 Hz), 5.87 (d, 1H, J=14.5 Hz), 6.69 (d, 1H, J=9.0 Hz), 6.78 (d, 1H, J=9.0 Hz), 7.13-8.01 (m, 12H).

tR: 6.50 min, ESI (HRMS) m/z ($C_{54}H_{69}N_4O_3S_2^+$), calc: 885.4806. found: 885.4796.

CyNAMLA-478 (18 mg, yield 13%). $^1$H-NMR (500 MHz, $CDCl_3$): 1.07 (t, 3H, J=7.5 Hz), 1.59 (s, 6H), 1.65 (s, 6H), 1.70-1.76 (m, 4H), 1.86-1.89 (m, 2H), 1.95 (s, 3H), 2.1-2.13 (m, 2H), 2.24 (s, 3H), 2.42-2.45 (m, 3H), 2.50-2.54 (m, 4H), 2.70 (t, 2H, J=7.5 Hz), 3.08-3.11 (m, 4H), 3.11 (t, 2H, J=6.5 Hz), 3.46 (t, 2H, J=6.5 Hz), 3.57-3.59 (m, 2H), 3.89 (t, 2H, J=7.5 Hz), 4.42 (t, 2H, J=7.5 Hz), 4.57 (t, 2H, J=6.5 Hz), 5.89 (d, 1H, J=13.5 Hz), 5.94 (d, 1H, J=13.5 Hz), 6.42 (d, 1H, J=14.0 Hz), 6.66 (d, 1H, J=15.0 Hz), 7.13-8.01 (m, 12H).

tR: 6.74 min, ESI (HRMS) m/z ($C_{55}H_{71}N_4O_2S_2^+$), calc: 883.5013. found: 883.5028.

SERS Measurements of CyNAMLA-Gold Colloid Mixtures

20-µM solutions of CyNAMLA compounds in deionized water were mixed with Au colloid ($2.6 \times 10^{10}$ particles/mL) in a 1:9 ratio (v/v). 20 µL of the CyNAMLA-Au colloid mixtures were placed on a clean glass slide with a cover slip and measured under the Raman microscope. The results are plotted as average intensities of five independent experiments, and are shown in FIG. 19.

BSA Encapsulation

20-µM solutions of CyNAMLA compounds in deionized water were mixed with Au colloid ($2.6 \times 10^{10}$ particles/mL) in a 1:9 ratio (v/v). After 10 minutes, the colloidal mixtures were treated with 0.5% BSA mixed with 25% glutaraldehyde (15:1) and incubated at room temperature for 4 hours followed by centrifugation (8000 rpm, 5 min). In order to remove the excess aldehyde groups, pellets were re-suspended in 10 mM glycine with 10 mM sodium citrate at room temperature for 30 minutes. The BSA-encapsulated AuNPs were washed three times by centrifugation, resuspended in 1 mM sodium citrate, and stored at 4° C.

Evaluation of the SERS Signal Stabilities of CyNAMLA- and DTTC-Functionalized AuNPs The SERS signals of BSA-encapsulated nanotags derivatized with CyNAMLA-80, CyNAMLA-92, CyNAMLA-221, CyNAMLA-262, CyNAMLA-381, CyNAMLA-478 or DTTC were measured for one month. SERS spectra were obtained upon excitation with a 785 nm laser (60 mW power). The SERS intensities of the highest Raman peak (i.e., 523 $cm^{-1}$ for CyNAMLA compounds and 495 $cm^1$ for DTTC) were plotted as means±standard deviation of five independent measurements taken from the same sample on the indicated day. The results are shown in FIGS. 21A and 21B.

Antibody Conjugation and Cellular SERS Studies

The carboxylic acid groups of BSA were activated with N-(3-(dimethylamino)-propyl)-N'-ethylcarbodiimide (EDC) (125 nmol) and N-hydroxysuccinimide (NHS) (125 nmol). After 30 minutes, excess EDC and NHS was removed by three rounds of centrifugation (8000 rpm, 10 min), and the BSA-encapsulated AuNPs were re-suspended in PBS using Amicon Ultra 3K centrifuge filters (Millipore). The activated particles were then treated with a mouse monoclonal anti-HER2 or scFv anti-HER2 at 25° C. for 2 hours and then overnight at 4° C. Non-specific binding chemicals and antibodies were removed by centrifugation (8000 rpm, 10 min) and the final nanotags were re-suspended in PBS and stored at 4° C.

Human cancer cell lines (MDA-MB231 and SKBR-3) were grown in RPMI 1640 medium supplemented with 10% (v/v) fetal bovine serum (FBS) and antibiotics (100 U/ml penicillin and 100 µg/ml streptomycin) at 37° C. in a humidified atmosphere with 5% $CO_2$, then were incubated with scFv-conjugated AuNPs (in the presence or absence of pre-incubated free scFv) for 1 hour at 37° C., washed three times with cold PBS, gently scraped and resuspended in PBS to a cell density of $1 \times 10^6$ cells/mL. SERS measurements of the resulting cell suspensions were taken. The results are shown in FIG. 22.

Dark-Field Microscopy Procedures

Figure 23B:
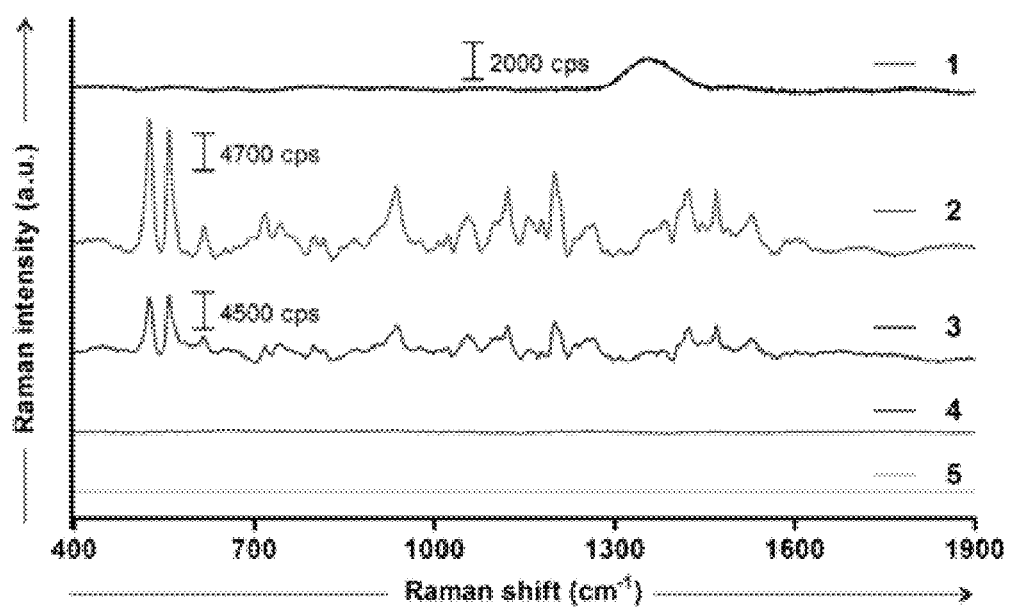
FIG. 23B is a Raman spectrum of the SERS signals from points 1-5 in FIG. 23A.

Approximately 50,000 cells (SKBR-3 or MDA-MB231) were plated in an 8-well chamber slide (Lab-Tek II, Nunc, USA) and incubated overnight at 37° C., 5% $CO_2$. After 24 hours, the medium was removed and scFv-conjugated SERS nanotags (450 pM) in serum-free medium was added to the cells. The cells were incubated for 1 hour at 37° C., and fixed with 4% paraformaldehyde for 15 minutes. The cells were then rinsed twice with PBS, and subsequently mounted with Vectasheild fluorescent mounting medium. Cells were visualized using an enhanced dark field (EDF) illumination system (CytoViva) attached to a Nikon Eclipse 80i microscope. The system consisted of a CytoViva 150 dark-field condenser that was in place of the original condenser of the microscope and attached via a fiber optic light guide to a Solarc 24 W metal halide light source. Images were taken under a 60× oil objective lens with an iris. A drop of the NP-treated cell suspension was added to poly-L-lysine-coated microscope slides, and samples were viewed as wet mounts, using type A immersion oil. The results are shown in FIGS. 23A and 23B.

In Vivo SERS Imaging Procedures

Balb/c nude mice obtained from the Biological Resource Centre, Biomedical Sciences Institutes were anesthetized by intraperitoneal injection of a mixture of ketamine (150 mg/kg) and xylazine (10 mg/kg) at the age of 4-6 weeks. SKBR-3 or MDA-MB231 cells were injected subcutaneously into the rear flank of the mouse ($5 \times 10^6$ cells per site in a volume of 150 µL). When the tumors grew to a size around 0.2 cm in diameter, scFv-conjugated SERS nanotags (500 pM, 150 µL) were injected into the tail vein of the mice. After 5 hours, the mice were anesthetized by intraperitoneal injection of a solution of ketamine and xylazine. SERS measurements of tumor and non-tumor sites from the same mouse were carried out using a Renishaw Raman microscope with laser excitation of 785 nm and laser power of 60 mW. The results are shown in FIGS. 24A and 24B.

Example 4

Identification and Development of In Vivo Imaging Probes for Activated Macrophages in an Animal Model of Inflammation Macrophages are present in virtually all tissues. In peripheral tissues, they are the first line of defense against injury and infection. Following activation, macrophages initiate the recruitment of effector molecules and other immune cells to kill pathogens and restore tissue integrity. In clinical diagnosis of inflammation, leukocytes are isolated from a patient's blood, and the macrophage cells are labelled, then re-injected into the patient. However, this method still cannot identify the site of inflammation in the body. Therefore, there is a need for an in vivo imaging probe that can enable the non-invasive examination of activated macrophages on a live animal.

In order to identify CyNA probes that could selectively stain mouse macrophage Raw 264.7 cell line (a mouse leukemic monocyte macrophage cell line), a library of CyNA compounds was assayed in a high-throughput cell imaging-based screen. The cell images were recorded using an automated imaging microscope system, IMAGEXPRESS MICRO™, and the fluorescent images were analyzed by cellular fluorescence intensity using METAXPRESS® image processing software. CyNA-374 selectively stained mouse macrophages, but not mouse splenocytes.

To validate the selectivity of CyNA-374, primary mouse peritoneal cavity cells were prepared. The identity of the mouse peritoneal cells was confirmed with CD11b macrophage antibody and flow cytometry. Next, the mouse peritoneal cells, Raw 264.7 cells and splenocytes were seeded in parallel. The following day, the cells were incubated with 1 µM CyNA-374 for 1 hour, then analyzed immediately using fluorescence microscopy. CyNA-374 stained both the Raw 264.7 cells and the mouse peritoneal cells by fluorescence spectroscopy, indicating that CyNA-374 was selective for macrophages.

To determine if CyNA-374 could stain activated macrophages, Raw 264.7 cells were activated to M1 macrophages. Raw 264.7 cells were plated at $5 \times 10^6$ cells/well and allowed to adhere. In some experiments, the cells were then starved for 12 hours, meaning that cells were washed with phosphate-buffered saline (PBS) and incubated in DMEM supplemented with 1% penicillin/streptomycin for 12 hours, but without 10% FBS. After 12 hours, the cells were exposed to 60 ng/mL LPS and, at the 24-hour time point, the supernatant from the cells stimulated by LPS was collected for measurement of $NO_2$ using the Griess reaction. The unstimulated Raw 264.7 cells produced approximately 8.5 µmol/L $NO_2$, while the stimulated Raw 264.7 (or M1) cells produced approximately 45 μmol/L $NO_2$. The M1 cells were seeded in parallel with the unactivated Raw 264.7 cells and the splenocytes. The cells were incubated with 1 μM CyNA-374 for 1 hour, then analyzed using fluorescence microscopy. CyNA-374 stained both the unactivated Raw 264.7 cells and the M1 cells.

Figure 26:
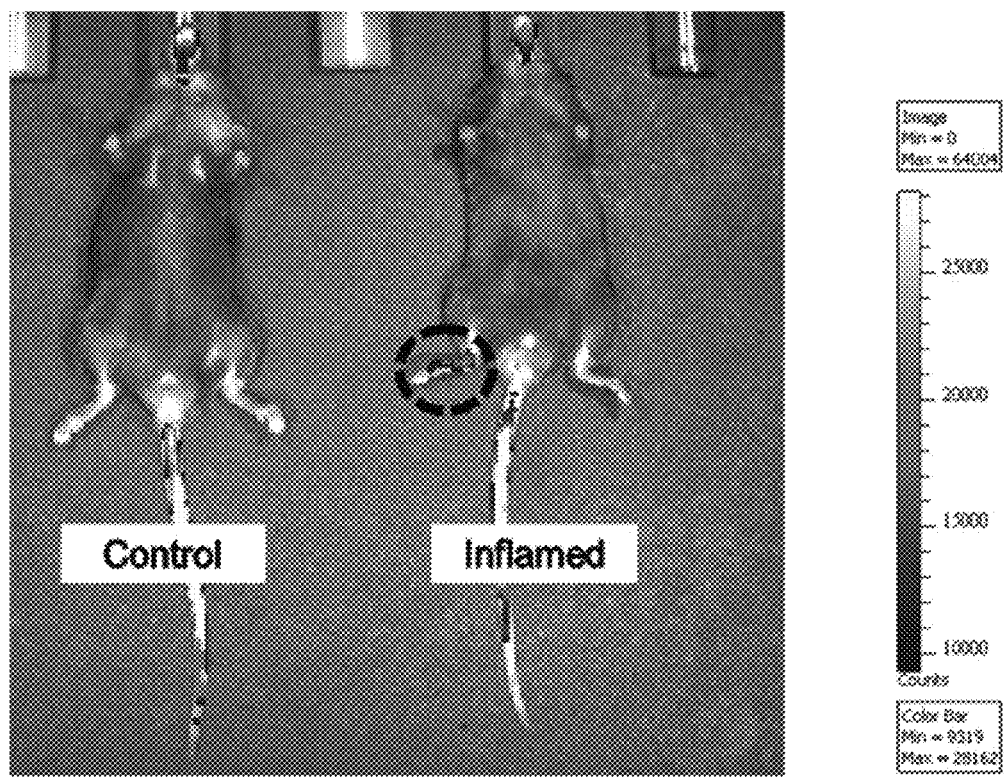
FIG. 26 is a fluorescence image of mice after injection with CyNA-374 (left mouse), or with LPS and CyNA-374 (right mouse).

CyNA-374 was used to image live, inflamed animals. 6-8-Week old C57BL6/J mice were injected with 100 μL of 1 mg/mL LPS on each right paw. After two days, 250 μL of 100 μM CyNA-374 (mixed with 1% PEG and 0.1% TWEEN-20) was injected via tail vein into a mouse that had been treated with LPS and a mouse that had not received LPS. After 30 minutes, the mice were imaged using an IVIS Imaging System. FIG. 26 is a fluorescence image of mice after injection with CyNA-374 (left mouse), or with LPS and CyNA-374 (right mouse).

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

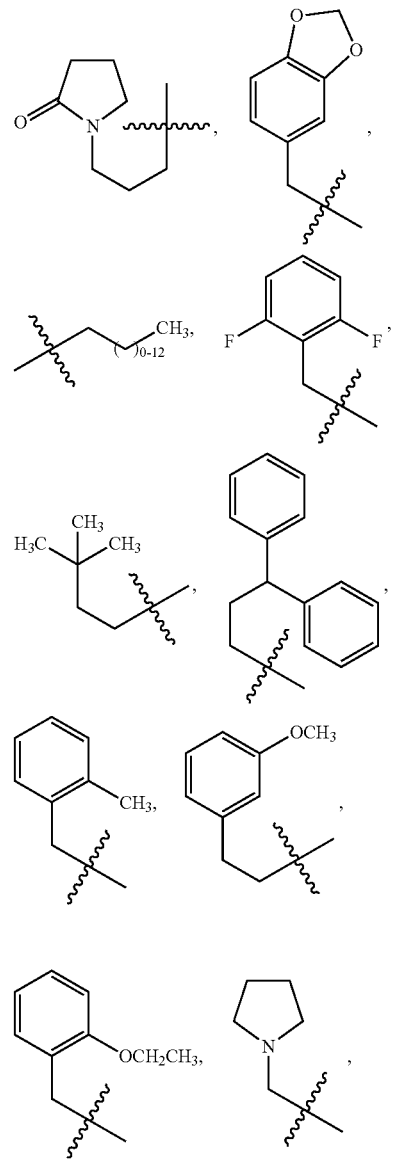

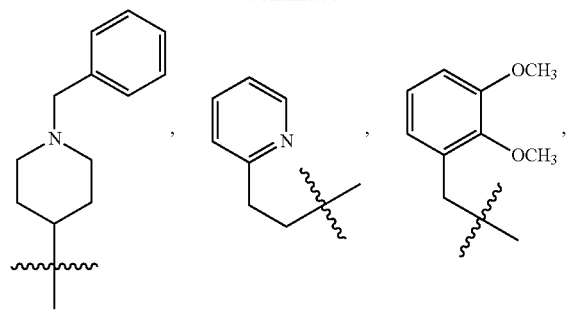
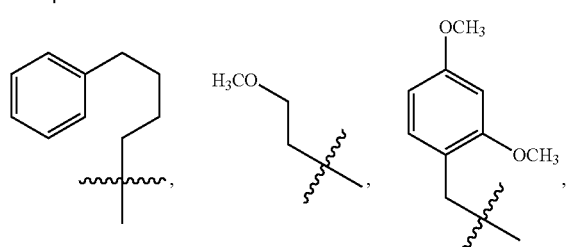
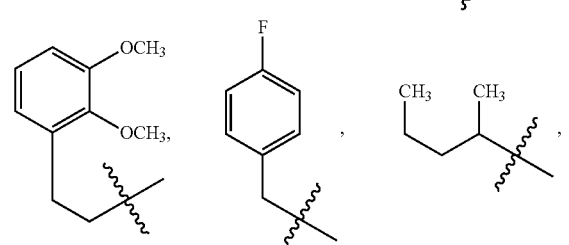
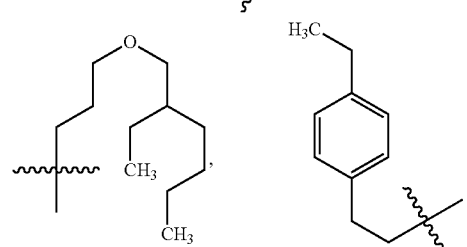
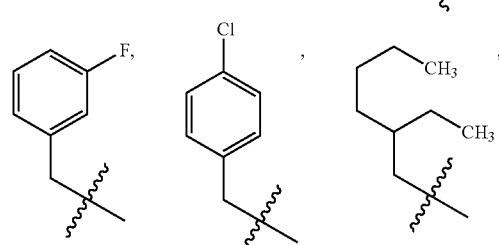
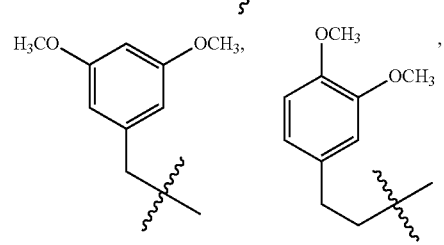
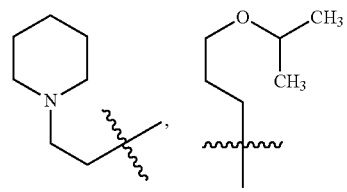
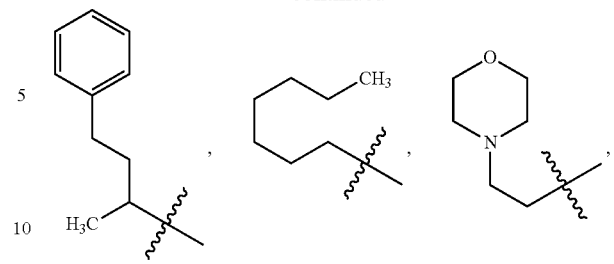
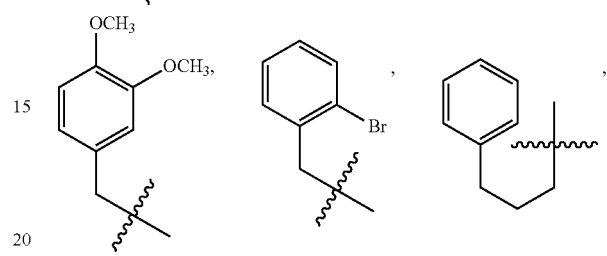
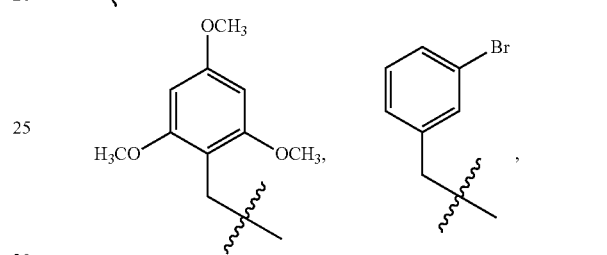
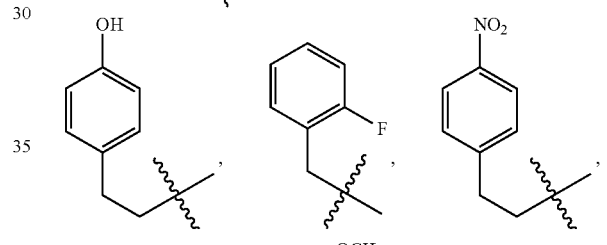
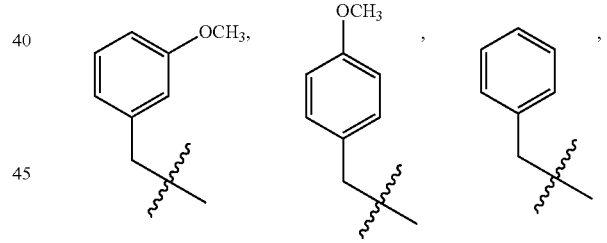
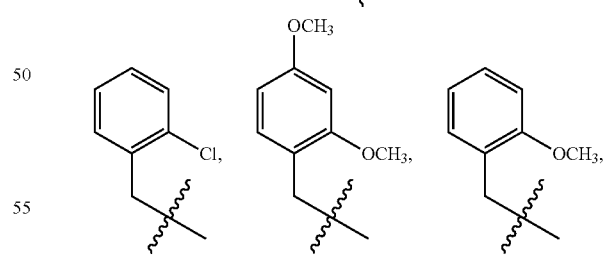
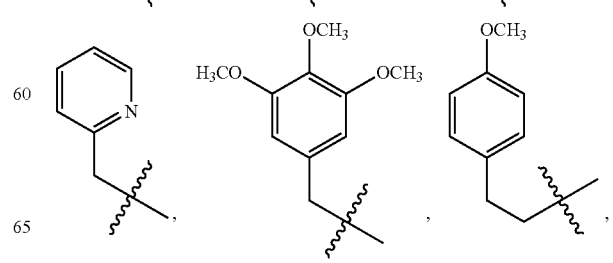

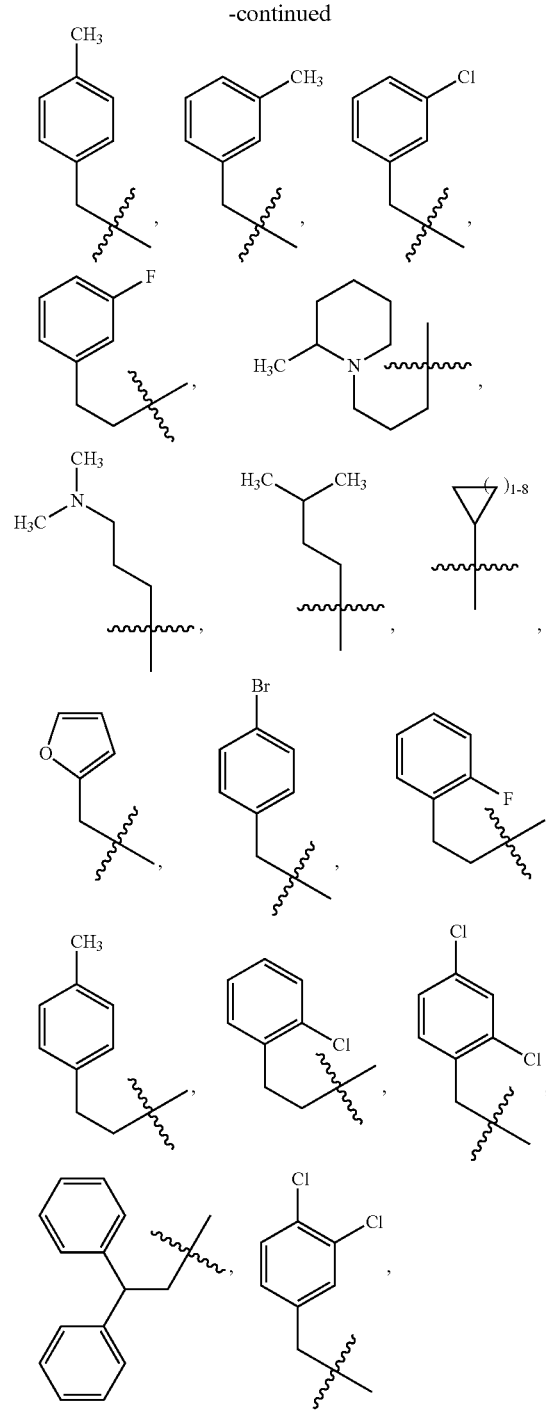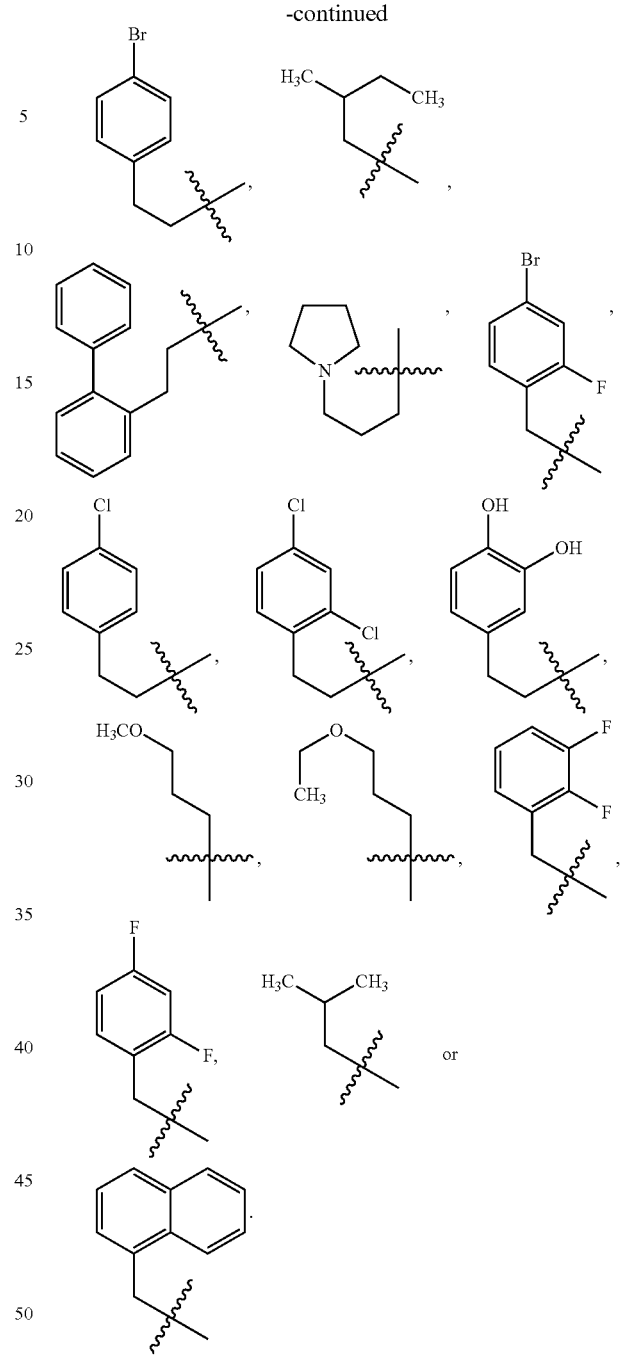

What is claimed is:

1. A compound represented by the following structural formula:

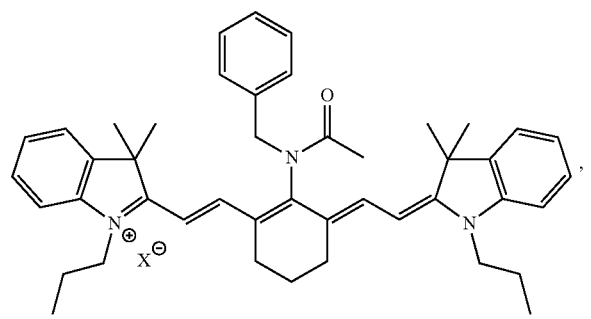

wherein X is iodo.

2. A method of detecting activated macrophage cells in an animal, comprising:
 a) administering to the animal the compound of claim 1 in an amount sufficient to stain the activated macrophage cells; and
 b) visualizing the stained activated macrophage cells with fluorescence microscopy, wherein the presence of a fluorescent signal indicates the presence of stained activated macrophage cells, thereby detecting activated macrophage cells in the animal.

3. The method of claim 2, wherein the animal is a live animal.

4. A method of detecting an inflamed tissue in an animal, comprising:
 a) administering to the animal the compound of claim 1 in an amount sufficient to stain activated macrophage cells present at the inflamed tissue; and
 b) visualizing the stained cells present at the inflamed tissue with fluorescence microscopy, wherein the presence of a fluorescent signal is indicative of the presence of an inflamed tissue targeted by the stained activated macrophage cells.

5. The method of claim 4, wherein the animal is a live animal.

6. A compound represented by the following structural formula:

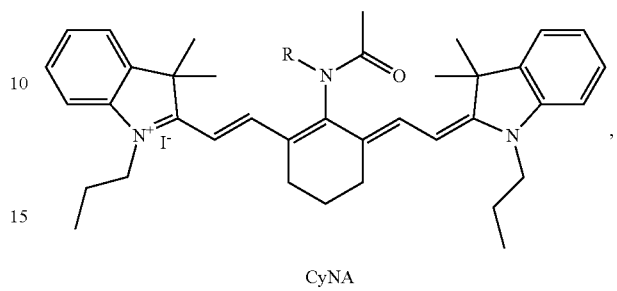

wherein R is